(12) United States Patent
Wang et al.

(10) Patent No.: US 8,486,933 B2
(45) Date of Patent: Jul. 16, 2013

(54) PYRIMIDINE INHIBITORS OF KINASE ACTIVITY

(75) Inventors: Gary T. Wang, Libertyville, IL (US); Robert A. Mantei, Franklin, WI (US); Scott A. Erickson, Zion, IL (US); Steve D. Fidanze, Grayslake, IL (US); George S. Sheppard, Wilmette, IL (US); Jieyi Wang, Lake Bluff, IL (US); Randy L. Bell, Lindenhurst, IL (US)

(73) Assignee: AbbVie Inc., North Chicago, IL (US)

( * ) Notice: Subject to any disclaimer, the term of this patent is extended or adjusted under 35 U.S.C. 154(b) by 384 days.

(21) Appl. No.: 12/787,735

(22) Filed: May 26, 2010

(65) Prior Publication Data
US 2010/0305112 A1  Dec. 2, 2010

Related U.S. Application Data

(60) Provisional application No. 61/181,545, filed on May 27, 2009.

(51) Int. Cl.
| | |
|---|---|
| *A61K 31/541* | (2006.01) |
| *A61K 31/496* | (2006.01) |
| *A61K 31/506* | (2006.01) |
| *A61K 31/5377* | (2006.01) |
| *C07D 403/14* | (2006.01) |
| *C07D 413/14* | (2006.01) |
| *C07D 417/14* | (2006.01) |

(52) U.S. Cl.
USPC .............. 514/228.2; 514/252.19; 514/252.18; 514/256; 514/234.5; 544/295; 544/333; 544/122; 544/62

(58) Field of Classification Search
USPC .................... 514/228.2, 252.19, 252.18, 256, 514/234.5; 544/295, 333, 122, 62
See application file for complete search history.

(56) References Cited

FOREIGN PATENT DOCUMENTS

| WO | WO03030909 A1 | 4/2003 |
|---|---|---|
| WO | WO03074515 A1 | 9/2003 |
| WO | WO2006129100 A1 | 12/2006 |
| WO | WO2008073687 A2 | 6/2008 |

OTHER PUBLICATIONS

Adams T. E., et al., "Structure and function of the type 1 insulin-like growth factor receptor", Cellular and Molecular Life Sciences, 2000, vol. 57 (7), pp. 1050-1093.
Alexia C., et al., "An evaluation of the role of insulin-like growth factors (IGF) and of type-I IGF receptor signalling in hepatocarcinogenesis and in the resistance of hepatocarcinoma cells against drug-induced apoptosis", Biochem Pharmacol, 2004, vol. 68 (6), pp. 1003-1015.
Arteaga C.L., et al., "Growth Inhibition of Human Breast Cancer Cells in Vitro with an Antibody Against the Type I Somatomedin Receptor," Cancer Research, 1989, vol. 49 (22), pp. 6237-6241.
Bateman J. M., et al., "Insulin/IGF Signalling in Neurogenesis," Cellular and Molecular Life Sciences, 2006, vol. 63 (15), pp. 1701-1705.
Benito M., et al., "IGF-I: A Mitogen also Involved in Differentiation Processes in Mammalian Cells," The International Journal of Biochemistry & Cell Biology, 1996, vol. 28 (5), pp. 499-510.
Berge S. M., et al., "Pharmaceutical Salts", J Pharmaceutical Sciences, 1977, vol. 66 (1), pp. 1-19.
Bergmann U., et al., "Insulin-like growth factor I overexpression in human pancreatic cancer: evidence for autocrine and paracrine roles", Cancer Research , 1995, vol. 55 (10), pp. 2007-2011.
Bohula E. A., et al., "Targeting the type 1 insulin-like growth factor receptor as anti-cancer treatment", Anti-cancer Drugs., 2003, vol. 14 (9), pp. 669-682.
Brady G., et al., "Serum levels of insulin-like growth factors (IGFs) and their binding proteins (IGFBPs), -1, -2, -3, in oral cancer", International Journal of Oral and Maxillofacal Surgery, 2007, vol. 36 (3), pp. 259-262.
Brown Guy C., "Control of respiration and ATP synthesis in mammalian mitochondria and cells", Biochemical, 1992, vol. 284, pp. 1-13.
Bruning Jens C., et al., "A Muscle-Specific Insulin Receptor Knockout Exhibits Features of the Metabolic Syndrome of NIDDM without Altering Glucose Tolerance", Molecular Cell, 1998, vol. 2 (5), pp. 559-569.
Burfeind P., et al., "Antisense RNA to the type I insulin-like growth factor receptor suppresses tumor growth and prevents invasion by rat prostate cancer cells in vivo", The Proceedings of the National Academy of Sciences of the United States of America, 1996, vol. 93 (14), pp. 7263-7268.

(Continued)

*Primary Examiner* — Kristin Bianchi
(74) *Attorney, Agent, or Firm* — Glen J. Gesicki

(57) ABSTRACT

Described herein are compounds of formula (I) or pharmaceutical acceptable salts or solvates thereof,

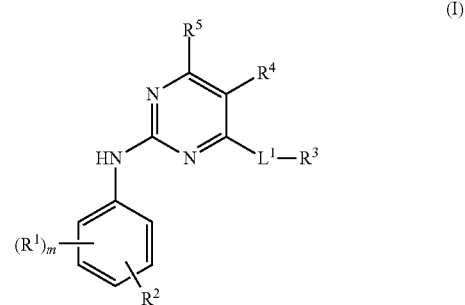

wherein $L^1$, $R^1$, $R^2$, $R^3$, $R^4$, $R^5$, and m are defined in the description. Methods of making said compounds, and compositions containing said compounds which are useful for inhibiting kinases such as IGF-1R are also disclosed.

22 Claims, No Drawings

OTHER PUBLICATIONS

Coppola D., et al., "A Functional Insulin-Like Growth Factor I Receptor is Required for the Mitogenic and Transforming Activities of the Epidermal Growth Factor Receptor," Molecular and Cellular Biology, 1994, vol. 14 (7), pp. 4588-4595.

Cross L.C., et al., "IUPAC Commission on Nomenclature of Organic Chemistry: Rules for the Nomenclature of Organic Chemistry, Section E: Stereochemistry," Pure and Applied Chemistry, 1976, vol. 45, pp. 11-30.

Dandekar Ajai A., et al., "Comparison of the Signaling Abilities of the Cytoplasmic Domains of the Insulin Receptor and the Insulin Receptor-Related Receptor in 3T3-L1 Adipocytes", Endocrinology, 1998, vol. 139 (8), pp. 3578-3584.

Deangelis T., et al., "Insulin-Like Growth Factor I Receptor is Required for the Mitogenic and Transforming Activities of the Platelet-Derived Growth Factor Receptor," Journal of Cellular Physiology, 1995, vol. 164 (1), pp. 214-221.

Del Valle L., et al., "Insulin-like growth factor I receptor activity in human medulloblastomas", Clinical Cancer Research, 2002, vol. 8 (6), pp. 1822-1830.

Djavan B., et al., "Insulin-like growth factors and prostate cancer", World Journal of Urology, 2001, vol. 19 (4), pp. 225-233.

Durai R., et al., "The role of the insulin-like growth factor system in colorectal cancer: review of current knowledge", International Journal Colorectal Diseases., 2005, vol. 20 (3), pp. 203-220.

Greene T., et al., "Protective Groups in Organic Synthesis," 1999, Third Edition, Table of Contents.

Guo Y S., et al., "Characterization of insulinlike growth factor I receptors in human colon cancer", Gastroenterology, 1992, vol. 102 (4), pp. 1101-1108.

Harrington E. A., et al., "C-Myc-Induced Apoptosis in Fibroblasts is Inhibited by Specific Cytokines," The EMBO Journal, 1994, vol. 13 (14), pp. 3286-3295.

Jiang Y., et al., "A high expression level of insulin-like growth factor I receptor is associated with increased expression of transcription factor Sp1 and regional lymph node metastasis of human gastric cancer", 2004, vol. 21 (8), pp. 755-764.

Jiang Y., et al., "Induction of Tumor Suppression and Glandular Differentiation of A549 Lung Carcinoma Cells by Dominant-Negative IGF-I Receptor," Oncogene, 1999, vol. 18, pp. 6071-6077.

Kaleko M., et al., "Overexpression of the Human Insulinlike Growth Factor I Receptor Promotes Ligand-Dependent Neoplastic Transformation," Molecular and Cellular Biology, 1990, vol. 10 (2), pp. 464-473.

Kellerer M., et al., "Insulin- and insulin-like growth-factor-I receptor tyrosine-kinase activities in human renal carcinoma", 1995, vol. 62 (5), pp. 501-507.

Kurmasheva R.T., et al., "IGF-I Mediated Survival Pathways in Normal and Malignant Cells," Biochimica et Biophysica Acta, 2006, vol. 1766, pp. 1-22.

Leroith D., et al., "The Insulin-Like Growth Factor System and Cancer," Cancer Letters, 2003, vol. 195, pp. 127-137.

Li, et al., "Two New Monoclonal Antibodies against the ? Subunit of the Human Insulin-Like Growth Factor-I Receptor," Biochemical and Biophysical Research Communications, 1993, vol. 196 (1), pp. 92-98.

Li Wanqing, et al., "Role of the Activation Loop Tyrosines in Regulation of the Insulin-like Growth Factor I Receptor-tyrosine Kinase", The Journal of Biological Chemistry, 2006, vol. 281 (33), pp. 23785-23791.

Mathis G.,, "HTRF(R) Technology", J Biomol Screen, 1999, 4 (6), 309-314.

Morrione A., et al., "Failure of the Bovine Papillomavirus to Transform Mouse Embryo Fibroblasts with a Targeted Disruption of the Insulin-Like Growth Factor I Receptor Genes," Journal of Virology, 1995, vol. 69 (9), pp. 5300-5303.

Neuvians T P., et al., "Differential expression of IGF components and insulin receptor isoforms in human seminoma versus normal testicular tissue", 2005, vol. 7 (5), pp. 446-456.

O'Brien M F., et al., "Insulin-like growth factor I and prostate cancel", Urology, 2001, vol. 58 (1), pp. 1-7.

Pollak M N., et al., "Insulin and insulin-like growth factor signalling in neoplasia", 2008, vol. 8 (12), pp. 915-928.

Pollak Michael N., et al., "Insulin-Like Growth Factors and Neoplasia", Nature Reviews Cancer, 2004, vol. 4, pp. 505-518.

Poste, et al., "Chapter 4: Lipid Vesicles as Carriers for Introducing Biologically Active Materials into Cells" in: Methods in Cell Biology, Prescott D.M., ed., Academic Press, 1976, vol. 14, pp. 33-71.

Qi H., et al., "Expression of type 1 insulin-like growth factor receptor in marrow nucleated cells in malignant hematological disorders: correlation with apoptosis," 2006, vol. 85 (2), pp. 95-101.

Samani A.A., et al., "The Role of the IGF System in Cancer Growth and Metastasis: Overview and Recent Insights," Endocrine Reviews, 2007, vol. 28 (1), pp. 20-47.

Sarma P.K.S., et al., "Progress in the Development of Small Molecule Inhibitors of Insulin-Like Growth Factor-1 Receptor Kinase," Expert Opinion on Therapeutic Patents, 2007, vol. 17 (1), pp. 25-35.

Sciacca Laura, et al., "In IGF-I receptor-deficient leiomyosarcoma cells autocrine IGF-II induces cell invasion and protection from apoptosis via the insulin receptor isoform A", Oncogene, 2002, vol. 21, pp. 8240-8250.

Scotlandi K., et al., "Blockage of Insulin-like Growth Factor-I Receptor Inhibits the Growth of Ewing's Sarcoma in Athymic Mice," Cancer Research, 1998, vol. 58, pp. 4127-4131.

Sell C., et al., "Effect of a Null Mutation of the Insulin-Like Growth Factor I Receptor Gene on Growth and Transformation of Mouse Embryo Fibroblasts," Molecular and Cellular Biology, 1994, vol. 14 (6), pp. 3604-3612.

Sell C., et al., "Simian Virus 40 Large Tumor Antigen is Unable to Transform Mouse Embryonic Fibroblasts Lacking Type 1 Insulin-Like Growth Factor Receptor," Proceedings of the National Academy of Sciences, 1993, vol. 90, pp. 11217-11221.

Sohda M., et al., "The role of insulin-like growth factor 1 and insulin-like growth factor binding protein 3 in human esophageal cancer", Anticancer Res. , 2004, vol. 24 (5A), pp. 3029-3034.

Surmacz E., et al., "Function of the IGF-I Receptor in Breast Cancer," Journal of Mammary Gland Biology and Neoplasia, 2000, vol. 5 (1), pp. 95-105.

Trent J C., et al., "Early effects of imatinib mesylate on the expression of insulin-like growth factor binding protein-3 and positron emission tomography in patients with gastrointestinal stromal tumor", Cancer, 2006, vol. 107 (8), pp. 1898-1908.

Trojan J., et al., "Loss of tumorigenicity of rat glioblastoma directed by episome-based antisense cDNA transcription of insulin-like growth factor I", Proc Natl Acad Sci, 1992, vol. 89 (11), pp. 4874-4878.

Van Nimwegen M. J. et al., "Focal Adhesion Kinase: A Potential Target in Cancer Therapy," Biochemical Pharmacology, 2007, vol. 73, pp. 597-609.

Vella V., et al., "A novel autocrine loop involving IGF-II and the insulin receptor isoform-A stimulates growth of thyroid cancer", J Clin Endocrinol Metab., 2002, vol. 87 (1), pp. 245-254.

Vella V., et al., "The IGF system in thyroid cancer: new concepts", Mol Pathol., 2001, vol. 54 (3), pp. 121-124.

Walenkamp M.J.E., et al., "Genetic Disorders in the Growth Hormone—Insulin-Like Growth Factor-I Axis," Hormone Research, 2006, vol. 66, pp. 221-230.

Wu X., et al., "Serum levels of insulin growth factor (IGF-I) and IGF-binding protein predict risk of second primary tumors in patients with head and neck cancer", Clinical Cancer Research, 2004, vol. 10 (12), pp. 3988-3995.

Yeh A H., et al., "Human melanoma cells expressing V600E B-RAF are susceptible to IGF1R targeting by small interfering RNAs", Oncogene, 2006, vol. 25 (50), pp. 6574-6581.

Zhao H., et al., "Plasma levels of insulin-like growth factor-1 and binding protein-3, and their association with bladder cancer risk", The Journal of urology, 2003, vol. 169 (2), pp. 714-717.

Zumkeller W., et al., "Insulin-like growth factor system in neuroblastoma tumorigenesis and apoptosis: potential diagnostic and therapeutic perspectives", Horm Metab Res. , 1999, vol. 31 (2-3), pp. 138-141.

Zumkeller W., et al., "The IGF/IGFBP system in CNS malignancy", Mol Pathol. , 2001, vol. 54 (4), pp. 227-229.

Zumkeller W., et al., "The insulin-like growth factor system in hematopoietic cells", Leuk Lymphoma. , 2002, vol. 43 (3), pp. 487-491.

PYRIMIDINE INHIBITORS OF KINASE ACTIVITY

This application claims priority to U.S. Provisional Patent Application Ser. No. 61/181,545, which was filed on May 27, 2009 and is incorporated herein by reference.

TECHNICAL FIELD

Provided herein are compounds that inhibit protein kinases such as IGF-1R, compositions containing the compounds, and methods of treating diseases using the compounds and the compositions thereof.

BACKGROUND

Receptor tyrosine kinases (RTKs) have been implicated in cellular signaling pathways that control various cellular functions, including cell division, growth, metabolism, differentiation and survival, through reversible phosphorylation of the hydroxyl groups of tyrosine residues in proteins. Extracellular signals are transduced via activation of the cell surface receptors, with amplification and propagation using a complex choreography of cascades of protein phosphorylation and protein dephosphorylation events to avoid uncontrolled signaling. These signaling pathways are highly regulated, often by complex and intermeshed kinase pathways where each kinase may itself be regulated by one or more other kinases and protein phosphatases. The biological importance of these finely tuned systems is such that a variety of cell proliferative disorders have been linked to defects in one or more of the various cell signaling pathways mediated by tyrosine or serine/threonine kinases.

Receptor tyrosine kinases (RTKs) catalyze phosphorylation of certain tyrosyl amino acid residues in various proteins, including themselves, which govern cell growth, proliferation and differentiation. Insulin-like growth factor-1 receptor (IGF-1R) is a transmembrane tyrosine kinase ubiquitous among fetal and post-natal cell types. The IGF signaling axis is made up of multiple ligands (IGF-1, IGF-2 and Insulin), at least six high affinity ligand binding proteins and proteases, multiple receptors (IGF-1R & IGF-2R, IR and IRR), and many other down stream signaling proteins (Pollak, M N et al., Nature Reviews Cancer (2004) 4(7):505-518). The structure and function of the IGF-1R has been reviewed by Adams et al., Cell. Mol. Life Sci. (2000) 57:1050-1093 and Benito, M et al., Int J Biochem Cell Biol (1996) 28(5):499-510. The receptor is activated by the ligands IGF-1 and IGF-2, which are mitogenic proteins that signal through the IGF-1R and IR in an endocrine, paracrine or autocrine manner. Activation of the IGF-1 receptor tyrosine kinase elicits cellular responses which include cellular proliferation and protection of cells from apoptosis. (Id.) Over expression of IGF-1R leads to malignant transformation of cultured cells, while down regulation can reverse the transformed phenotype of tumor cells and potentially render them susceptible to apoptosis. (Id.) There are two splice variants of the IR gene, the IR-β isoform which regulates glucose uptake and is expressed in liver, muscle and adipose tissue, and the exon 11 variant human insulin receptor isoform A (IR-A) binds IGF-2 with high affinity and promotes proliferation and protection from apoptosis (Sciacca L. Oncogene (2002) 21(54):8240-8250). IR-A is predominantly expressed in fetal tissue and malignancies and at this receptor, IGF-2 is more potent than insulin in stimulating cancer cell migration. (Sciacca, Oncogene (2002) supra). Insulin receptor-related receptor tyrosine kinase (IRR) has 79% homology with the kinase domain of IR and is expressed only in a few limited cell types (Dandekar, A A et al., Endocrinology (1998) 139(8):3578-3584).

IGF-1R is a hetero-tetrameric, transmembrane, cell surface receptor tyrosine kinase. (Benito, Int J Biochem Cell Biol (1996)) An IGF-1 binding domain is part of the extracellular alpha-chain of IGF-1R, whereas the intracellular beta-chain contains the tyrosine kinase domain. Three tyrosine residues represent autophosphorylation sites, specifically $Tyr^{1131}$, $Tyr^{1135}$, and $Tyr^{1136}$, within the activation loop of the IGF-1R beta catalytic domain (Li, W et al., J. Biol. Chem. (2006) 281(33):23785-23791). Phosphorylation of all three is required for full receptor activation, and precedes phosphorylation of juxtamembrane tyrosines and carboxy terminus serines. The insulin receptor has three similar autophosphorylation sites on the activation loop and juxtamembrane region. Activation and autophoshorylation results in the recruitment of multiple docking proteins and the generation of intracellular signaling (Benito, Int J Biochem Cell Biol (1996)). Once activated, IGF-1R and IR can phosphorylate or interact directly with a number of intracellular protein substrates, including IRS-1, IRS-2, Grb2, Grb10, Grb14, Shc, SOC, 14.3.3, FAK, or indirectly with other proteins like PI3K and MAPK (Benito, M et al. Int J Biochem Cell Biol (1996) 28(5):499-510) (Brown, G C et al., Biochem. J (1992) 284: 1-13; Bruning, J C et al., Mol. Cell (1998) 2(5):559-569). Focal adhesion kinase (FAK) is of particular interest because of its role as a regulator of cell survival, proliferation, migration and invasion. FAK is activated by growth factor receptors such as IGF-1R, by binding through its N-terminal domain and autophosphorylation at $Tyr^{397}$. Activated or over expressed FAK is common in a wide variety of cancers, and may play a role in human carcinogenesis (van Nimwegen, M J et al., Biochem. Pharmacol. (2007) 73(5):597-609).

In addition to its role in cancers, the IGF receptor plays important and diverse roles in growth and development (Benito, M et al. Int J Biochem Cell Biol (1996) 28(5):499-510). IGF-1R has been implicated in several metabolic, and immunological diseases (Walenkamp, M J et al., Horm. Res. (2006) 66(5):221-230; Kurmasheva, R. T et al., Biochim. Biophys. Acta—Rev on Cancer (2006) 1766(1):1-22; Bateman, J M et al., Cell. Mol. Life Sci. (2006) 63(15):1701-1705, LeRoith, D, et al., Can. Lett. (2003) 195:127-137 and Samani A, et al., Endocrine Reviews 28(1):20-47.)

The role of the IGF/IGF-1R signaling system in cancer has been thoroughly examined over the last 15 years. In particular, the implication of IGF-1R in human cancer stems from its roles in stimulating mitogenesis, mobility and metastasis and in protecting against apoptosis. (Kurmasheva, Biochim. Biophys. Acta (2006).) Interest has grown with the understanding that in addition to its antiapoptotic and mitogenic roles, IGF/IGF-1R signaling seems to be necessary for the establishment and continuation of a transformed phenotype. It has been well established that constitutive activation or over expression, often results in non-adherent cell growth, even under serum depleted conditions in vitro, and is associated with the formation of tumors in nude mice. (Kaleko M et al, Mol Cell Biol. (1990) 10(2): 464-473). Perhaps even more importantly, it has been firmly established that cells, in which the gene encoding for IGF-1R has been deactivated, are totally resistant to transformation by agents which are normally capable of immortalizing normal cells, such as over expression of PDGFR or EGFR, the T antigen of the SV40 virus, the E5 protein of bovine papilloma virus, and activated ras. (DeAngelis T et al., Cell. Physiol. (1995) 1640:214-221; Coppola D et al., Mol. Cell. Biol. (1994) 14(7):4588-4595; Morrione A J, Virol. 1995 695300-5303; Sell C et al., Mol. Cell. Biol. (1994) 14(6):3604-3612; Sell C et al., Proc. Natl. Acad. Sci.

USA (1993) 90(23):11217-11221). Thus, IGF-1R has been identified as the major survival factor that protects from oncogene induced cell death (Harrington et al., EMBO J. (1994) 13( ):3286-3295). IGF-1R is expressed in a large number and variety of tumors and the IGFs amplify the tumor growth through their interaction with the receptor. Evidence supporting the role of IGF-1R in carcinogenesis can be found in studies using monoclonal antibodies directed towards the receptor which inhibit the proliferation of numerous cell lines in culture and in vivo (Arteaga C et al., Cancer Res. (1989) 49(22):6237-6241; Li et al., Biochem. Biophys. Res. Com. (1993) 196(1):92-98; Scotlandi K et al., Cancer Res. (1998) 58(18):4127-4131). Dominant negative IGF-1R is capable of inhibiting tumor proliferation (Jiang et al., Oncogene (1999) 18(44):6071-6077). The IGF signaling axis is implicated in various tumor types including:

breast cancer (Surmacz, J. Mammary Gland Bio. Neoplasia (2000) 5(1):95-105, LeRoith, Can. Lett. (2003) and Artega, Cancer Res. (1989)), sarcoma including soft-tissue sarcoma (e.g., cartilage sarcoma, connective tissue (chondrosarcoma) and fibrous matrix (fibrosarcoma)) and hard bony sarcomas (e.g., Ewing's sarcoma, osteosarcoma and giant cell tumor of bone) (Scotlandi, Cancer Res. (1998), lung cancer, including non-small cell and small cell lung carcinomas and mesotheliomas (Jiang, Y et al., Oncogene (1999) 18:6071-6077 and LeRoith, Can. Lett. (2003), prostate cancer (Djavan et al., World J Urol. (2001) 19(4): 225-233; O'Brien et al., Urology (2001) 58(1):1-7 and LeRoith, Can. Lett. (2003)), colorectal cancer (Guo et al., Gastroenterology, 1992, 102, 1101-1108; Durai, R et al., Int. J Colorectal Dis. (2005) 20(3):203-220 and LeRoith, Can. Lett. (2003)), renal cancer (Kellerer M. et al., Int. J. Cancer (1995) 62(5): 501-507), pancreatic cancer (Bergmann, U et al., Cancer Res. (1995) 55(10):2007-2011), hematologic cancers, including lymphoblastic T cell leukemia, chronic myelogenous leukemia, chronic lymphocytic leukemia, hairy-cell leukemia, acute lymphoblastic leukemia, acute myelogenous leukemia, chronic neutrophilic leukemia, acute lymphoblastic T cell leukemia, plasmacytoma, immunoblastic large cell leukemia, mantle cell leukemia, multiple myeloma, megakaryoblastic leukemia, acute megakaryocytic leukemia, promyelocytic leukemia, erythroleukemia, malignant lymphoma, Hodgkins lymphoma, non-Hodgkins lymphoma, lymphoblastic T cell lymphoma, Burkitt's lymphoma, follicular lymphoma, myelodysplastic syndromes, (Zumkeller W et al., Leuk. Lymph (2002) 43(3):487-491; and Qi, Ann Hematol. (2006) 85:95-101.), neuroblastomas (Zumkeller, W et al., Horm. Metab. Res. 1999, 31, 138-141), primary CNS tumors including: astrocytomas (also known as "gliomas") including glioblastoma multiforme; meningiomas and medulloblastomas (Zumkeller, W et al., Mol. Pathol. (2001) 54(4):227-229, Del Valle L, et al., Clin. Cancer Res. (2002) 8:1822-1830 and Trojan et al., Proc. Natl. Acad. Sci. USA (1992) 89:4874-4878.), secondary CNS tumors, i.e., metastases in the central nervous system (e.g., the brain), of a tumor originating outside of the central nervous system (Burfeind P, et al, PNAS (1996) 93:7263-7268), head and neck cancer (Wu X., et al, Clin. Cancer Res. (2004) 10:3988-95), thyroid cancer (Vella V et al., J. Clin. Endocrinol. Metab. (2002) 87:245-254; Vella V et al., Mol. Pathol. (2001) 54(3):121-124), hepatocarcinoma (Alexia, C et al., Biochem. Pharmacol. (2004) 68:1003-1015), ovarian cancer, vulval cancer, cervical cancer, endometrial cancer, testicular cancer (Neuvians T P, et al, Neoplasia (2005) 7:446-56), bladder cancer (Zhao H., et al, J. Urology (2003) 169:714-717), esophageal cancer (Sohda M, et al, Anticancer Research. (2004) 24:3029-3034), gastric cancer (Jiang, Y, et al, Clinical & Experimental Metastasis (2004) 21:755-64), buccal cancer, cancer of the mouth, (Brady G et al., Int. J. of Oral & Maxillofacial Surg. (2007) 36:259-62).

GIST (gastrointestinal stromal tumor) (Trent J C, et al, Cancer. (2006) 107:1898-908), and skin cancer including melanoma (Yeh A H, et al, Oncogene. (2006) 25:6574-81).

Thus, in virtually all types of human cancers there is a strong association between dysregulation of IGF signaling and carcinogenesis (Bohula E A et al., Anticancer Drugs (2003) 14(9):669-682). Inhibition of IGF-1R and/or IR expression or function has been shown to block tumor growth and metastasis and also enhance sensitivity to other antineoplastic therapies, including cytotoxic drugs and radiation. (Bohula, Anticancer Drugs (2003).

The identification of effective small compounds which specifically inhibit signal transduction and cellular proliferation by modulating the activity of tyrosine kinases to regulate and modulate abnormal or inappropriate cell proliferation, differentiation, or metabolism is therefore desirable. In particular, the identification of methods and compounds that specifically inhibit the function of a tyrosine kinase which is essential for angiogenic processes or the formation of vascular hyperpermeability leading to edema, ascites, effusions, exudates, and macromolecular extravasation and matrix deposition as well as associated disorders would be beneficial.

SUMMARY

One embodiment pertains to compounds having formula (I)

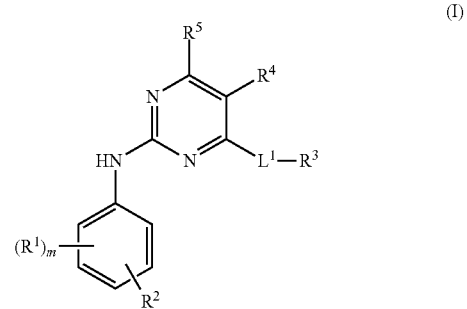

or pharmaceutically acceptable salts, solvates, prodrugs, salts of prodrugs or combinations thereof, wherein m is 0, 1, 2, 3, or 4;

$L^1$ is NH or O;

each occurrence of $R^1$, when present, is independently alkyl, alkenyl, alkynyl, halogen, haloalkyl, CN, $NO_2$, $-OR^{Z1}$, $-OC(O)R^{Z2}$, $-SR^{Z1}$, $-S(O)R^{Z2}$, $-S(O)_2R^{Z2}$, $-S(O)_2N(R^{Z3})(R^{Z4})$, $-N(R^{Z3})(R^{Z4})$, $-N(R^{Z3})C(O)R^{Z2}$, $-N(R^{Z3})C(O)OR^{Z2}$, $-N(R^{Z3})S(O)_2R^{Z2}$, $-N(R^{Z3})C(O)N(R^{Z3})(R^{Z4})$, $-N(R^{Z3})S(O)_2N(R^{Z3})(R^{Z4})$, $-C(O)R^{Z1}$, $-C(O)OR^{Z1}$, $-C(O)N(R^{Z3})(R^{Z4})$, $-(C_{1-6}$ alkylenyl$)-OR^{Z1}$, $-(C_{1-6}$ alkylenyl$)-OC(O)R^{Z2}$, $-(C_{1-6}$ alkylenyl$)-SR^{Z1}$, $-(C_{1-6}$ alkylenyl$)-S(O)R^{Z2}$, $-(C_{1-6}$ alkylenyl$)-S(O)_2R^{Z2}$, $-(C_{1-6}$ alkylenyl$)-S(O)_2N(R^{Z3})(R^{Z4})$, $-(C_{1-6}$ alkylenyl$)-N(R^{Z3})(R^{Z4})$, $-(C_{1-6}$ alkylenyl$)-N(R^{Z3})C(O)R^{Z2}$, $-(C_{1-6}$ alkylenyl$)-N(R^{Z3})C(O)OR^{Z2}$, $-(C_{1-6}$ alkylenyl$)-N(R^{Z3})S(O)_2R^{Z2}$, $-(C_{1-6}$ alkylenyl$)-N(R^{Z3})C(O)N(R^{Z3})(R^{Z4})$, $-(C_{1-6}$ alkylenyl$)-N(R^{Z3})S(O)_2N(R^{Z3})(R^{Z4})$, $-(C_{1-6}$ alkylenyl$)-C(O)R^{Z1}$, $-(C_{1-6}$ alkylenyl$)-C(O)OR^{Z1}$, or $-(C_{1-6}$ alkylenyl$)-C(O)N(R^{Z3})(R^{Z4})$;

$R^2$ is a heterocycle optionally substituted with 1, 2, 3, or 4 substituents independently selected from the group consisting of alkyl, alkenyl, alkynyl, halogen, haloalkyl, oxo, CN, $NO_2$, $G^2$, $-OR^6$, $-OC(O)R^7$, $-SR^6$, $-S(O)R^7$, $-S(O)_2R^7$, $-S(O)_2N(R^8)(R^9)$, $-N(R^8)(R^9)$, $-N(R^8)C(O)R^7$, $-N(R^8)C(O)OR^7$, $-N(R^8)S(O)_2R^7$, $-N(R^8)C(O)N(R^8)(R^9)$, $-N(R^8)C(O)-(C_{1-6}$ alkylenyl$)-N(R^8)(R^9)$, $-N(R^8)S(O)_2N(R^8)(R^9)$, $-C(O)R^6$, $-C(O)OR^6$, $-C(O)N(R^8)(R^9)$, $-(C_{1-6}$ alkylenyl$)-G^3$, $-(C_{1-6}$ alkylenyl$)-OR^6$, $-(C_{1-6}$ alkylenyl$)-OC(O)R^7$, $-(C_{1-6}$ alkylenyl$)-SR^6$, $-(C_{1-6}$ alkylenyl$)-S(O)R^7$, $-(C_{1-6}$ alkylenyl$)-S(O)_2R^7$, $-(C_{1-6}$ alkylenyl$)-S(O)_2N(R^8)(R^9)$, $-(C_{1-6}$ alkylenyl$)-N(R^8)(R^9)$, $-(C_{1-6}$ alkylenyl$)-N(R^8)C(O)R^7$, $-(C_{1-6}$ alkylenyl$)-N(R^8)C(O)OR^7$, $-(C_{1-6}$ alkylenyl$)-N(R^8)S(O)_2R^7$, $-(C_{1-6}$ alkylenyl$)-N(R^8)C(O)N(R^8)(R^9)$, $-(C_{1-6}$ alkylenyl$)-N(R^8)S(O)_2N(R^8)(R^9)$, $-(C_{1-6}$ alkylenyl$)-C(O)R^6$, $-(C_{1-6}$ alkylenyl$)-C(O)OR^6$, and $-(C_{1-6}$ alkylenyl$)-C(O)N(R^8)(R^9)$;

$R^3$ is benzimidazolyl, indazolyl, benzothiazolyl, benzoxazolyl, or quinolinyl; each of which is independently unsubstitued or substituted with 1, 2, or 3 substituents independently selected from the group consisting of alkyl, alkenyl, alkynyl, halogen, $G^3$, $-(C_{1-6}$ alkylenyl$)-G^3$, $-O(alkyl)$, $-O(haloalkyl)$, $-SR^{Z1}$, $-S(O)R^{Z2}$, $-S(O)_2R^{Z2}$, $-C(O)N(R^{Z3})(R^{Z4})$, and haloalkyl; with the proviso that when $R^3$ is quinolinyl, then $R^2$ is substituted with 1, 2, 3, or 4 substituents wherein one of the substituents is $G^2$, $R^4$ is alkyl, haloalkyl, halogen, or —CN;

$R^5$ is hydrogen, alkyl, haloalkyl, halogen, or —CN;

each occurrence of $R^6$ and $R^9$ are each independently hydrogen, alkyl, haloalkyl, $-(C_{1-6}$ alkylenyl$)-CN$, $-(C_{1-6}$ alkylenyl$)-OH$, $-(C_{1-6}$ alkylenyl$)-C(O)OH$, $G^3$, or $-(C_{1-6}$ alkylenyl$)-G^3$;

each occurrence of $R^7$ is independently alkyl, haloalkyl, $-(C_{1-6}$ alkylenyl$)-CN$, $-(C_{1-6}$ alkylenyl$)-OH$, $G^3$, or $-(C_{1-6}$ alkylenyl$)-G^3$;

each occurrence of $R^8$ is independently hydrogen, alkyl, or haloalkyl;

$G^2$ is a heterocycle optionally substituted with 1, 2, 3, 4, or 5 $R^{10}$ groups;

each occurrence of $G^3$ is independently aryl, heteroaryl, heterocycle, cycloalkyl, or cycloalkenyl, each of which is independently unsubstituted or substituted with 1, 2, 3, 4, or 5 $R^{10}$ groups;

each occurrence of $R^{10}$ is independently alkyl, alkenyl, alkynyl, halogen, haloalkyl, oxo, CN, $NO_2$, $-OR^{Z1}$, $-OC(O)R^{Z2}$, $-SR^{Z1}$, $-S(O)R^{Z2}$, $-S(O)_2R^{Z2}$, $-S(O)_2N(R^{Z3})(R^{Z4})$, $-N(R^{Z3})(R^{Z4})$, $-N(R^{Z3})C(O)R^{Z2}$, $-N(R^{Z3})C(O)OR^{Z2}$, $-N(R^{Z3})S(O)_2R^{Z2}$, $-N(R^{Z3})C(O)N(R^{Z3})(R^{Z4})$, $-N(R^{Z3})S(O)_2N(R^{Z3})(R^{Z4})$, $-C(O)R^{Z1}$, $-C(O)OR^{Z1}$, $-C(O)N(R^{Z3})(R^{Z4})$, $-(C_{1-6}$ alkylenyl$)-OR^{Z1}$, $-(C_{1-6}$ alkylenyl$)-OC(O)R^{Z2}$, $-(C_{1-6}$ alkylenyl$)-SR^{Z1}$, $-(C_{1-6}$ alkylenyl$)-S(O)R^{Z2}$, $-(C_{1-6}$ alkylenyl$)-S(O)_2R^{Z2}$, $-(C_{1-6}$ alkylenyl$)-S(O)_2N(R^{Z3})(R^{Z4})$, $-(C_{1-6}$ alkylenyl$)-N(R^{Z3})(R^{Z4})$, $-(C_{1-6}$ alkylenyl$)-N(R^{Z3})C(O)R^{Z2}$, $-(C_{1-6}$ alkylenyl$)-N(R^{Z3})C(O)OR^{Z2}$, $-(C_{1-6}$ alkylenyl$)-N(R^{Z3})S(O)_2R^{Z2}$, $-(C_{1-6}$ alkylenyl$)-N(R^{Z3})C(O)N(R^{Z3})(R^{Z4})$, $-(C_{1-6}$ alkylenyl$)-N(R^{Z3})S(O)_2N(R^{Z3})(R^{Z4})$, $-(C_{1-6}$ alkylenyl$)-C(O)R^{Z1}$, $-(C_{1-6}$ alkylenyl$)-C(O)OR^{Z1}$, or $-(C_{1-6}$ alkylenyl$)-C(O)N(R^{Z3})(R^{Z4})$;

each occurrence of $R^{Z1}$, $R^{Z3}$, and $R^{Z4}$, are each independently hydrogen, alkyl, or haloalkyl; and each occurrence of $R^{Z2}$ is independently alkyl or haloalkyl.

Also provided are pharmaceutical compositions comprising therapeutically effective amounts of one or more compounds of formula (I) or pharmaceutically acceptable salts or solvates thereof, in combination with one or more pharmaceutically acceptable carriers. These pharmaceutical compositions are useful for the treatment of diseases or conditions described herein.

One embodiment is directed to methods for treating cancers in mammals comprising administering thereto therapeutically effective amounts of one or more compounds described herein, or pharmaceutically acceptable salts or solvates thereof, alone or in combination with one or more pharmaceutically acceptable carriers.

Yet another embodiment pertains to methods of decreasing tumor volume in mammals comprising administering thereto therapeutically effective amounts of one or more compounds described herein, or pharmaceutically acceptable salts or solvates thereof, alone or in combination with one or more pharmaceutically acceptable carriers.

Still another embodiment pertains to methods of treating bladder cancer, breast cancer, cervical cancer, colon cancer, endometrial cancer, esophageal cancer, lung cancer, ovarian cancer, pancreatic cancer, prostate cancer, rectal cancer, skin cancer, stomach cancer or thyroid cancer in mammals, or combinations thereof; the methods comprising administering thereto therapeutically effective amounts of one or more compounds described herein or pharmaceutically acceptable salts or solvates thereof, with or without also administering radiotherapy thereto, and alone or in combination with one or more pharmaceutically acceptable carriers.

Provided herein are the use of one or more compounds described herein, or pharmaceutically acceptable salts or solvates thereof for the preparation of medicaments for use in the treatment of diseases or conditions described herein, particularly, for use in the treatment of bladder cancer, breast cancer, cervical cancer, colon cancer, endometrial cancer, esophageal cancer, lung cancer, ovarian cancer, pancreatic cancer, prostate cancer, rectal cancer, skin cancer, stomach cancer, or thyroid cancer, or combinations thereof, in mammals (e.g., human) in need thereof.

The compounds, compositions comprising the compounds, and methods for treating or preventing conditions and disorders by administering the compounds or pharmaceutical compositions are further described herein.

These and other objectives of the invention are described in the following paragraphs. These objectives should not be deemed to narrow the scope of the invention.

DETAILED DESCRIPTION

This detailed description is intended only to acquaint others skilled in the art with Applicants' invention, its principles, and its practical application so that others skilled in the art may adapt and apply the invention in its numerous forms, as they may be best suited to the requirements of a particular use. This description and its specific examples are intended for purposes of illustration only. This invention, therefore, is not limited to the embodiments described in this patent application, and may be variously modified.

Provided are compounds of formula (I)

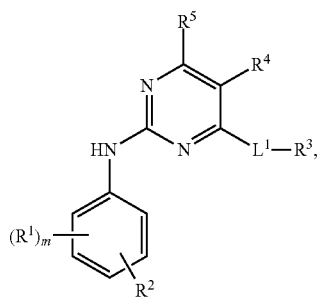

wherein $R^1$, $R^2$, $R^3$, $R^4$, $R^5$, $L^1$, and m are as disclosed above in the Summary and below in the Detailed Description. Compositions comprising such compounds and methods for treating conditions and disorders using such compounds and compositions are also disclosed.

In various embodiments, there may be variables that occur more than one time in any substituent or in the compound or any other formulae herein. Definition of a variable on each occurrence is independent of its definition at another occurrence. Further, combinations of variables are permissible only if such combinations result in stable compounds. Stable compounds are compounds that can be isolated from a reaction mixture.

a. DEFINITIONS

As used in the specification and the appended claims, unless specified to the contrary, the following terms have the meaning indicated:

The term "alkenyl" as used herein, means a straight or branched hydrocarbon chain containing from 2 to 10 carbons and containing at least one carbon-carbon double bond. Representative examples of alkenyl include, but are not limited to, ethenyl, 3-methylbut-2-enyl, prop-1-enyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkyl" as used herein, means a saturated, straight or branched hydrocarbon chain containing from 1 to 10 carbon atoms. The term "$C_{1-6}$ alkyl" as used herein, means a saturated, straight or branched chain hydrocarbon containing from 1 to 6 carbon atoms. Representative examples of alkyl include, but are not limited to, methyl, ethyl, n-propyl, iso-propyl, n-butyl, sec-butyl, iso-butyl, tert-butyl, n-pentyl, iso-pentyl, neopentyl, n-hexyl, 1-methylbutyl, 2-methylbutyl, 3-methylbutyl, 1,1-dimethylpropyl, 1,2-dimethylpropyl, 2,2-dimethylpropyl, 1-methylpropyl, 1-ethylpropyl, 1,2,2-trimethylpropyl, 2-ethylhexyl, 3-methylhexyl, 2,2-dimethylpentyl, 2,3-dimethylpentyl, n-heptyl, n-octyl, n-nonyl, and n-decyl.

The term "alkylene" or "alkylenyl" means a divalent group derived from a saturated, straight or branched hydrocarbon chain of from 1 to 10 carbon atoms. The term "$C_{1-6}$ alkylenyl" means a divalent group derived from a saturated, straight or branched hydrocarbon chain of from 1 to 6 carbon atoms. Representative examples of alkylene include, but are not limited to, —$CH_2$—, —$CH(CH_3)$—, —$CH_2C(CH_3)_2$—, —$CH(C_2H_5)$—, —$CH(CH(CH_3)(C_2H_5))$—, —$C(H)(CH_3)$ $CH_2CH_2$—, —$C(CH_3)_2$—, —$CH_2CH_2$—, —$CH_2CH_2CH_2$—, —$CH_2CH_2CH_2CH_2$—, and —$CH_2CH(CH_3)CH_2$—.

The term "alkynyl" as used herein, means a straight or branched hydrocarbon chain containing from 2 to 10 carbon atoms and containing at least one carbon-carbon triple bond. Non-limiting examples of alkynyl include, but are not limited, to acetylenyl, 1-propynyl, 2-propynyl, 1,1-dimethylprop-2-ynyl, 1-propyl-pent-3-ynyl, 3-butynyl, 2-pentynyl, and 1-butynyl.

The term "aryl" as used herein, means phenyl or a bicyclic aryl. The bicyclic aryl is naphthyl, or a phenyl fused to a monocyclic cycloalkyl, or a phenyl fused to a monocyclic cycloalkenyl. Non-limiting examples of the bicyclic aryl include, but are not limited to, dihydroindenyl, indenyl, naphthyl, dihydronaphthalenyl, and tetrahydronaphthalenyl. The aryl groups are attached to the parent molecular moiety through any carbon atom contained within the groups respectively.

The term "cycloalkenyl" as used herein, means a monocyclic or bicyclic carbocyclic ring system containing zero heteroatoms in the ring. The monocyclic cycloalkenyl has three-, four-, five-, six-, seven- or eight carbon atoms and zero heteroatoms. The three or four-membered ring systems have one double bond, the five- or six-membered ring systems have one or two double bonds, and the seven- or eight-membered ring systems have one, two or three double bonds. Non-limiting examples of monocyclic cycloalkenyls include, but are not limited to, 2-cyclohexen-1-yl, 3-cyclohexen-1-yl, 2,4-cyclohexadien-1-yl and 3-cyclopenten-1-yl. Bicyclic cycloalkenyls are exemplified by a monocyclic cycloalkenyl fused to a monocyclic cycloalkyl, or a monocyclic cycloalkenyl fused to a monocyclic cycloalkenyl. Non-limiting examples of bicyclic ring systems include, but are not limited to 3a, 4, 5, 6, 7, 7a-hexahydro-1H-indenyl, 4,5,6,7-tetrahydro-3aH-indene, and octahydronaphthalenyl. The cycloalkenyl groups are appended to the parent molecular moiety through any substitutable carbon atom within the groups, and can contain one or two alkylene bridges of 1, 2, 3, or 4 carbon atoms, wherein each bridge links two non-adjacent atoms within the groups.

The term "cycloalkyl" as used herein, means a monocyclic or a bicyclic cycloalkyl. The monocyclic cycloalkyl is a saturated carbocyclic ring system containing 3, 4, 5, 6, 7, or 8 carbon atoms and zero heteroatoms as ring atoms, and zero double bonds. Examples of monocyclic cycloalkyls include cyclopropyl, cyclobutyl, cyclopentyl, cyclohexyl, cycloheptyl, and cyclooctyl. Bicyclic cycloalkyl is exemplified by a monocyclic cycloalkyl fused to a monocyclic cycloalkyl. Non-limiting examples of bicyclic cycloalkyls include, but are not limited to, bicyclo[4.1.0]heptane, bicyclo[6.1.0] nonane, octahydroindene, and decahydronaphthalene. The monocyclic and the bicyclic cycloalkyl groups can contain one or two alkylene bridges of 1, 2, 3, or 4 carbon atoms, wherein each bridge links two non-adjacent atoms within the groups. Examples of such bridged cycloalkyls include, but are not limited to, bicyclo[3.1.1]heptyl (including but not limited thereto, bicyclo[3.1.1]hept-2-yl), bicyclo[2.2.1]heptyl, bicyclo[3.1.1]heptyl, bicyclo[2.2.2]octyl, bicyclo[3.3.1] nonyl, adamantyl (tricyclo[3.3.1.1$^{3,7}$]decane), and noradamantyl (octahydro-2,5-methanopentalene). The monocyclic and the bicyclic cycloalkyl groups of the present compounds can be appended to the parent molecular moiety through any substitutable carbon atom of the groups.

The term "halo" or "halogen" as used herein, means —Cl, —Br, —I, or —F.

The term "haloalkyl" as used herein, means an alkyl group, as defined herein, in which one, two, three, four, five, six, or seven hydrogen atoms are replaced by halogen. Representative examples of haloalkyl include, but are not limited to, chloromethyl, 2-fluoroethyl, 2-fluoropropyl, 2-fluoro-1-methylethyl, 2,2-difluoroethyl, trifluoromethyl, 2,2,2-trifluoroethyl, 2,2,2-trifluoro-1,1-dimethylethyl, difluoromethyl, 3-fluoro-3-methylbutyl, 3,3,3-trifluoropropyl, pentafluoroethyl, 2-chloro-3-fluoropentyl, and 2-iodoethyl.

The term "$C_{1-6}$ haloalkyl" as used herein, means a $C_{1-6}$ alkyl group, as defined herein, in which one, two, three, four, five, six, or seven hydrogen atoms are replaced by halogen.

The term "heteroaryl," as used herein, means a monocyclic heteroaryl or a bicyclic heteroaryl. The monocyclic heteroaryl is a 5- or 6-membered ring containing at least one heteroatom independently selected from the group consisting of O, N, and S. The 5-membered ring contains two double bonds and one, two, three, or four heteroatoms. The 6-membered ring contains three double bonds and one, two, three, or four heteroatoms. Non-limiting examples of monocyclic heteroaryl include, but are not limited to, furanyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl is exemplified by a monocyclic heteroaryl fused to phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Non-limiting examples of bicyclic heteroaryls include, but are not limited to, benzofuranyl, benzoxadiazolyl, benzoxazolyl (including but not limited thereto, 1,3-benzoxazolyl such as 1,3-benzoxazol-4-yl), benzothiazolyl (including, but not limited thereto, 1,3-benzothiazolyl, 1,3-benzothiazol-5-yl), benzimidazolyl (including but not limited thereto, 1H-benzimidazol-4-yl, 1H-benzimidazol-5-yl, 1H-benzimidazol-6-yl), benzodioxolyl, benzothienyl, chromenyl, cinnolinyl, furopyridine, indolyl, indazolyl (including but not limited thereto, 1H-indazol-5-yl, 2H-indazol-5-yl), isoindolyl, isoquinolinyl, naphthyridinyl, oxazolopyridine, quinolinyl (including but not limited thereto, quinolin-6-yl, quinolin-7-yl), and thienopyridinyl. The monocyclic and the bicyclic heteroaryl groups are connected to the parent molecular moiety through any substitutable carbon atom or any substitutable nitrogen atom contained within the groups. The nitrogen and the sulfur heteroatoms in the heteroaryl rings may optionally be oxidized and are within the scope of the invention.

The term "heterocycle" or "heterocyclic" as used herein, means a monocyclic or a bicyclic ring system containing at least one heteroatom in the ring. The monocyclic heterocycle is a 3-, 4-5-, 6-, 7-, or 8-membered monocyclic ring containing at least one heteroatom independently selected from the group consisting of O, N, and S. The 3- or 4-membered ring contains 1 heteroatom selected from the group consisting of O, N and S, and optionally one double bond. The 5-membered ring contains zero or one double bond, and one, two or three heteroatoms in the ring selected from the group consisting of O, N and S. The 6-, 7-, or 8-membered ring contains zero, one, or two double bonds, and one, two, or three heteroatoms in the ring selected from the group consisting of O, N and S. Non-limiting examples of monocyclic heterocycles include, but are not limited to, azetidinyl, azepanyl, aziridinyl, diazepanyl, 1,3-dioxanyl, 1,4-dioxanyl, 1,3-dioxolanyl, 4,5-dihydroisoxazol-5-yl, 3,4-dihydropyran-6-yl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl (including but not limited to piperazin-1-yl), piperidinyl (including but not limited to, piperidin-1-yl), pyranyl, pyrazolinyl, pyrazolidinyl, pyrrolinyl, pyrrolidinyl, tetrahydrofuranyl, tetrahydropyranyl, tetrahydrothienyl, thiadiazolinyl, thiadiazolidinyl, thiazolinyl, thiazolidinyl, thiomorpholinyl, thiopyranyl, and trithianyl. The bicyclic heterocycle is exemplified by a monocyclic heterocycle fused to a phenyl group, or a monocyclic heterocycle fused to a monocyclic cycloalkyl group, or a monocyclic heterocycle fused to a monocyclic cycloalkenyl group, or a monocyclic heterocycle fused to a monocyclic heterocycle group. Non limiting examples of bicyclic heterocycles include, but are not limited to, 1,3-benzodioxol-4-yl, 1,3-benzodithiolyl, 2,3-dihydro-1,4-benzodioxinyl, dihydrobenzofuranyl, 2,3-dihydro-1-benzothienyl, 2,3-dihydro-1H-indolyl, and 1,2,3,4-tetrahydroquinolinyl. The heterocycle groups are connected to the parent molecular moiety through any substitutable carbon atom or any substitutable nitrogen atom contained within the group. The monocyclic or bicyclic heterocycle groups can contain an alkenylene bridge of 2, 3, or 4 carbon atoms, or one or two alkylene bridges of 1, 2, 3, or 4 carbon atoms, wherein each bridge links two non-adjacent carbon atoms within the groups. Examples of such bridged heterocycles include, but are not limited to, oxaadamantane (2-oxatricyclo[3.3.1.1$^{3,7}$] decane), octahydro-2,5-epoxypentalene, hexahydro-2H-2,5-methanocyclopenta[b]furan, hexahydro-1H-1,4-methanocyclopenta[c]furan, oxabicyclo[2.2.1]heptane and 2,4-dioxabicyclo[4.2.1]nonane. The nitrogen and sulfur heteroatoms in the heterocycle rings may optionally be oxidized (e.g. 1,1-dioxidothiomorpholinyl (thiomorpholine sulfone)), and the nitrogen atoms may optionally be quarternized.

If a substituent is described as being optionally substituted with up to a particular number of non-hydrogen radicals, that substituent may be either (1) not substituted; or (2) substituted by up to that particular number of non-hydrogen radicals or by up to the maximum number of substitutable positions on the substituent, whichever is less. Thus, for example, if a substituent is described as a heteroaryl optionally substituted with up to 5 non-hydrogen radicals, then any heteroaryl with less than 5 substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical.

The term "oxo" as used herein, means =O.

The terms "treat", "treating", and "treatment" refer to a method of alleviating or abrogating a disease and/or its attendant symptoms.

The terms "prevent", "preventing" and "prevention" refer to a method of preventing the onset of a disease and/or its attendant symptoms or barring a subject from acquiring a disease. As used herein, "prevent", "preventing" and "prevention" also include delaying the onset of a disease and/or its attendant symptoms and reducing a subject's risk of acquiring a disease.

The term "therapeutically effective amount" refers to that amount of the compound being administered sufficient to prevent development of or alleviate to some extent one or more of the symptoms of the condition or disorder being treated.

The term "modulate" refers to the ability of a compound to increase or decrease the function, or activity, of a kinase. "Modulation", as used herein in its various forms, is intended to encompass antagonism, agonism, partial antagonism and/ or partial agonism of the activity associated with kinase.

Kinase inhibitors are compounds that, e.g., bind to, partially or totally block stimulation, decrease, prevent, delay activation, inactivate, desensitize, or down regulate signal transduction. Kinase activators are compounds that, e.g., bind to, stimulate, increase, open, activate, facilitate, enhance activation, sensitize or up regulate signal transduction.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The "subject" is defined herein to include animals such as mammals, including, but not limited to, primates (e.g., humans), cows, sheep, goats, horses, dogs, cats, rabbits, rats, mice and the like. In preferred embodiments, the subject is a human.

b. COMPOUNDS

IGF-1R inhibitors have formula (I) as described in the Summary.

Particular values of variable groups in compounds of formula (I) are as follows. Such values may be used where appropriate with any of the other values, definitions, claims or embodiments defined hereinbefore or hereinafter.

In compounds of formula (I), the variable 'm' has meanings as provided for in the Summary section. For example, certain embodiments provide compounds of formula (I) wherein m is 0. Certain embodiments pertain to compounds of formula (I) wherein m is 1.

$R^1$, if present, has values as described in the Summary. For example, each $R^1$, if present can be the same or different and is independently alkyl (e.g. $C_{1-6}$ alkyl), halogen, haloalkyl (e.g. trifluoromethyl), or —$OR^{Z1}$. In certain embodiments $R^1$, if present, is —$OR^{Z1}$ wherein $R^{Z1}$ is as disclosed in the Summary. For example, $R^{Z1}$ is $C_{1-6}$ alkyl such as but not limited to methyl.

Thus, provided herein but not limited thereto, are compounds of formula (I) wherein m is 1 and $R^1$ is —$OR^{Z1}$ such as, but not limited to, those of formula (I-i)

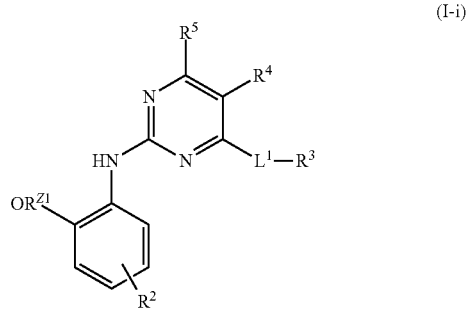

wherein variables $R^2$, $R^3$, $R^4$, $R^5$, $R^{Z1}$, and $L^1$ are as disclosed above in the Summary for formula (I) and in the embodiments below.

$L^1$ for compounds of formula (I) and (I-i) has values as disclosed in the Summary. One class of compounds of formula (I) and (I-i) include those defined wherein $L^1$ is NH. Another class of compounds includes those wherein $L^1$ is O.

$R^4$ for compounds of formula (I) and (I-i) has meanings as set forth in the Summary. In one class of compounds of formula (I) and (I-i), $R^4$ is $C_{1-6}$ alkyl (e.g. methyl), $C_{1-6}$ haloalkyl (e.g. trifluoromethyl), halogen (e.g. Br, Cl), or —CN.

$R^5$ has values as disclosed in the Summary. For example, in conjunction with any above or below embodiments of compounds of formula (I) and (I-i), $R^5$ is hydrogen.

$R^3$ has values as set forth in the Summary. For example, certain embodiments provide compounds of formula (I) and (I-i) wherein $R^3$ is indazolyl, benzimidazolyl, benzothiazolyl, or benzoxazolyl. One class of compounds include those wherein $R^3$ is benzimidazolyl such as, but not limited to, 1H-benzimidazol-4-yl, 1H-benzimidazol-5-yl, 1H-benzimidazol-6-yl. Other embodiments include, but are not limited to, those of formula (I) and (I-i) wherein $R^3$ is indazolyl (e.g. 1H-indazol-5-yl, 2H-indazol-5-yl). Further, another class of compounds of formula (I) and (I-i) includes, but is not limited to, those wherein $R^3$ is benzoxazolyl (e.g. 1,3-benzoxazol-4-yl) or benzothiazolyl (e.g. 1,3-benzothiazol-5-yl). Yet another class of compounds of formula (I) and (I-i) includes, but is not limited to, those wherein $R^3$ is quinolinyl (e.g. quinolin-6-yl, quinolin-7-yl). Each of the aforementioned rings of $R^3$ is optionally substituted.

The optional substituents of $R^3$ are as set forth in the Summary. In conjunction with any above or below embodiments of compounds of formula (I) and (I-i), each of these optional substituents of $R^3$ can be the same or different and is, for example, independently alkyl (e.g. $C_{1-6}$ alkyl such as but not limited to, methyl), halogen (e.g. Cl, F, and the like), $G^3$ (for example, optionally substituted aryl such as optionally substituted phenyl), —($C_{1-6}$ alkylenyl)-$G^3$ (e.g. —$CH_2$-phenyl, —$CH_2$—$CH_2$-phenyl; wherein the phenyl moiety is optionally substituted), —$S(O)_2R^{Z2}$, —$C(O)N(R^{Z3})(R^{Z4})$, or haloalkyl (e.g. $C_{1-6}$ haloalkyl such as but not limited to, trifluoromethyl). In certain embodiments, the optional substituent is $G^3$ (for example, optionally substituted aryl such as optionally substituted phenyl). In certain embodiments, each of the optional substituents of $R^3$ is independently selected from the group consisting of alkyl (e.g. $C_{1-6}$ alkyl such as but not limited to, methyl), halogen (e.g. Cl, F, and the like), —$S(O)_2R^{Z2}$, —$C(O)N(R^{Z3})(R^{Z4})$, and haloalkyl (e.g. $C_{1-6}$ haloalkyl such as but not limited to, trifluoromethyl). In certain embodiments, each of the optional substituents of $R^3$ is independently selected from the group consisting of alkyl (e.g. $C_{1-6}$ alkyl such as but not limited to, methyl) and —$S(O)_2R^{Z2}$. $R^{Z2}$, $R^{Z3}$, and $R^{Z4}$ for the aforementioned embodiments are as defined in the Summary. For example, $R^{Z2}$ is $C_{1-6}$ alkyl such as, but not limited to, methyl, ethyl, or isopropyl. $R^{Z3}$, and $R^{Z4}$ are, for example, independently hydrogen or $C_{1-6}$ alkyl such as, but not limited to, methyl, ethyl, or isopropyl.

$R^2$ has values as described in the Summary. In certain embodiments, $R^2$ is an optionally substituted monocyclic heterocycle. In certain embodiments, $R^2$ is a monocyclic heterocycle substituted with one or two substituents. In certain embodiment, $R^2$ is a monocyclic heterocycle substituted with one substituent. Non limiting examples of the monocyclic ring of $R^2$ include pyrrolidinyl, morpolinyl, thiomorpholinyl, 1,1-dioxothiomorpholinyl, piperazinyl, and piperidinyl, each of which is optionally substituted.

The optional substituents of $R^2$ are as set forth in the Summary. In conjunction with any above or below embodiments of compounds of formula (I) and (I-i), each of these optional substituents of $R^2$ can be the same or different and is, for example, independently alkyl (e.g. $C_{1-6}$ alkyl such as but not limited to, methyl, ethyl, isopropyl, and the like), haloalkyl (e.g. $C_{1-6}$ haloalkyl such as but not limited to, trifluoromethyl), $G^2$, or $N(R^8)(R^9)$. In certain embodiments, the substituents of $R^2$ is selected from the group consisting of $C_{1-6}$ alkyl and $N(R^8)(R^9)$. In certain embodiments, the optional substituent is $G^2$. $G^2$, $R^8$, and $R^9$ are as described in the Summary. $G^2$, for example, is an optionally substituted monocyclic heterocycle. In certain embodiments, $G^2$ is an optionally substituted piperazinyl. In certain embodiments, $G^2$ is piperazinyl substituted with $C_{1-6}$ alkyl (e.g. methyl, ethyl). $R^8$ and $R^9$ are for example, are each independently hydrogen or $C_{1-6}$ alkyl such as, but not limited to, methyl or ethyl. In certain embodiments, $R^8$ and $R^9$ are the same or different and are independently $C_{1-6}$ alkyl such as, but not limited to, methyl or ethyl.

It is appreciated that compounds of formula (I) and (I-i) with combinations of the above embodiments and subsets of the particular groups defined, including particular, more particular and preferred embodiments are contemplated.

Accordingly, one aspect relates to a group of compounds of formula (I) or (I-i), wherein $L^1$ is N(H) and $R^3$ is indazolyl, benzimidazolyl, benzoxazolyl, or benzothiazolyl; each of which is optionally substituted.

Another aspect relates to a group of compounds of formula (I) or (I-i) wherein $L^1$ is NH and $R^3$ is optionally substituted indazolyl.

Yet another aspect relates to a group of compounds of formula (I) or (I-i) wherein $L^1$ is NH and $R^3$ is optionally substituted benzimidazolyl.

Still another aspect relates to a group of compounds of formula (I) or (I-i) wherein $L^1$ is NH and $R^3$ is optionally substituted benzoxazolyl or optionally substituted benzothiazolyl.

Another aspect relates to a group of compounds of formula (I) or (I-i), wherein $L^1$ is O and $R^3$ is indazolyl, benzimidazolyl, benzoxazolyl, or benzothiazolyl; each of which is optionally substituted.

Yet another aspect relates to a group of compounds of formula (I) or (I-i) wherein $L^1$ is O and $R^3$ is optionally substituted indazolyl.

Still another aspect relates to a group of compounds of formula (I) or (I-i) wherein $L^1$ is O and $R^3$ is optionally substituted benzimidazolyl.

Another aspect relates to a group of compounds of formula (I) or (I-i) wherein $L^1$ is O and $R^3$ is optionally substituted benzoxazolyl or optionally substituted benzothiazolyl.

Within each group of compounds of formula (I) or (I-i) described above, the variables $R^1$, $R^2$, $R^4$, $R^5$, $R^{Z1}$, and m, and the optional substituents of $R^3$ are as described in the Summary and in the Detailed Description sections.

Thus, for each group of compounds of formula (I) or (I-i) described above, examples of a subgroup include but are not limited to those wherein $R^5$ is hydrogen.

Other examples of a subgroup of compounds of formula (I) include but are not limited to those wherein $R^5$ is hydrogen and m is 0.

Yet other examples of a subgroup of compounds of formula (I) include but are not limited to those wherein $R^5$ is hydrogen, m is 1, and $R^1$ is $OR^{Z1}$ wherein $R^{Z1}$ is as described in the Summary and Detailed Description sections.

Still other examples of a subgroup of compounds of formula (I) or (I-i) include but are not limited to those wherein $R^5$ is hydrogen and $R^2$ is an optionally substituted monocyclic heterocycle (e.g. pyrrolidinyl, morpolinyl, thiomorpholinyl, 1,1-dioxothiomorpholinyl, piperazinyl, or piperidinyl, each of which is optionally substituted as described in the Summary and the Detailed Description sections).

Still other examples of a subgroup of compounds of formula (I) or (I-i) include but are not limited to those wherein $R^5$ is hydrogen, $R^2$ is a monocyclic heterocycle (e.g. pyrrolidinyl, morpolinyl, thiomorpholinyl, 1,1-dioxothiomorpholinyl, piperazinyl, or piperidinyl, each of which is optionally substituted) optionally substituted with one or two substituents independently selected from the group consisting of alkyl (e.g. $C_{1-6}$ alkyl such as but not limited to, methyl, ethyl, isopropyl, and the like), haloalkyl (e.g. $C_{1-6}$ haloalkyl such as but not limited to, trifluoromethyl), $G^2$, and $N(R^8)(R^9)$; wherein $G^2$, $R^8$, and $R^9$ are as set forth in the Summary and the Detailed Description sections.

Further examples of a subgroup of compounds of formula (I) or (I-i) include but are not limited to those wherein $R^5$ is hydrogen, $R^2$ is a monocyclic heterocycle (e.g. pyrrolidinyl, morpolinyl, thiomorpholinyl, 1,1-dioxothiomorpholinyl, piperazinyl, or piperidinyl, each of which is optionally substituted) substituted with one $G^2$ group, and $G^2$ is as set forth in the Summary and the Detailed Description sections.

Yet other examples of a subgroup of compounds of formula (I) or (I-i) include but are not limited to those wherein $R^5$ is hydrogen, $R^2$ is a monocyclic heterocycle (e.g. pyrrolidinyl, morpolinyl, thiomorpholinyl, 1,1-dioxothiomorpholinyl, piperazinyl, or piperidinyl, each of which is optionally substituted) substituted with one $G^2$ group, and $G^2$ is optionally substituted piperazinyl.

Yet another embodiment is directed to a group of compounds of formula (I) wherein
  $L^1$ is NH;
  m is 0 or 1;
  $R^1$ is $OR^{Z1}$;
  $R^2$ is a monocyclic heterocycle ((e.g. pyrrolidinyl, morpolinyl, thiomorpholinyl, piperazinyl, or piperidinyl) substituted with one $G^2$ group;
  $G^2$ is an optionally substituted monocyclic heterocycle (e.g. optionally substituted piperazinyl);
  $R^3$ is indazolyl substituted with 1 or 2 substituents independently selected from the group consisting of alkyl (e.g. $C_{1-6}$ alkyl such as but not limited to, methyl) and $—S(O)_2R^{Z2}$.

Yet another embodiment is directed to a group of compounds of formula (I-i) wherein
  $L^1$ is NH;
  $R^2$ is a monocyclic heterocycle ((e.g. pyrrolidinyl, morpolinyl, thiomorpholinyl, piperazinyl, or piperidinyl) substituted with one $G^2$ group;
  $G^2$ is an optionally substituted monocyclic heterocycle (e.g. optionally substituted piperazinyl); and
  $R^3$ is indazolyl substituted with 1 or 2 substituents independently selected from the group consisting of alkyl (e.g. $C_{1-6}$ alkyl such as but not limited to, methyl) and $—S(O)_2R^{Z2}$.

Yet another aspect relates to a group of compounds of formula (I) or (I-i) wherein $L^1$ is NH, $R^3$ is optionally substituted quinolinyl, and $R^2$ is a monocyclic heterocycle ((e.g. pyrrolidinyl, morpolinyl, thiomorpholinyl, piperazinyl, or piperidinyl) substituted with 1, 2, or 3 substituents wherein one of the substituents is $G^2$, and the others are independently selected from alkyl (e.g. $C_{1-6}$ alkyl such as but not limited to, methyl, ethyl, isopropyl, and the like) and haloalkyl (e.g. $C_{1-6}$ haloalkyl such as but not limited to, trifluoromethyl).

Yet another aspect relates to a group of compounds of formula (I) or (I-i) wherein $L^1$ is NH, $R^3$ is optionally substituted quinolinyl, and $R^2$ is a monocyclic heterocycle ((e.g. pyrrolidinyl, morpolinyl, thiomorpholinyl, piperazinyl, or piperidinyl) substituted with one $G^2$ group.

Yet another aspect relates to a group of compounds of formula (I) or (I-i) wherein $L^1$ is O, $R^3$ is optionally substituted quinolinyl, and $R^2$ is a monocyclic heterocycle ((e.g. pyrrolidinyl, morpolinyl, thiomorpholinyl, piperazinyl, or piperidinyl) substituted with 1, 2, or 3 substituents wherein one of the substituents is $G^2$, and the others are independently selected from alkyl (e.g. $C_{1-6}$ alkyl such as but not limited to, methyl, ethyl, isopropyl, and the like) and haloalkyl (e.g. $C_{1-6}$ haloalkyl such as but not limited to, trifluoromethyl).

Yet another aspect relates to a group of compounds of formula (I) or (I-i) wherein $L^1$ is O, $R^3$ is optionally substituted quinolinyl, and $R^2$ is a monocyclic heterocycle ((e.g. pyrrolidinyl, morpholinyl, thiomorpholinyl, piperazinyl, or piperidinyl) substituted with one $G^2$ group.

Within each of the four groups of compounds of formula (I) or (I-i) described in the preceding four paragraphs, the variables m, $R^1$, $R^4$, $R^5$, $R^{Z1}$, m, and $G^2$ and the optional substituents of $R^3$ are as described in the Summary and the Detailed Description sections.

Thus, for each of the above four groups of compounds of formula (I) or (I-i), examples of a subgroup include but are not limited to those wherein $R^5$ is hydrogen.

Examples of another subgroup for each of the above four groups of compounds of formula (I) include but are not limited to those wherein $R^5$ is hydrogen and m is 0.

Yet other examples of a subgroup for each of the above four groups of compounds of formula (I) include but are not limited to those wherein $R^5$ is hydrogen, m is 1, and $R^1$ is $OR^{Z1}$ wherein $R^{Z1}$ is as described in the Summary and Detailed Description sections. For example, $R^{Z1}$ is $C_{1-6}$ alkyl such as, but not limited to, methyl.

Further examples of a subgroup for each of the above four groups of compounds of formula (I) or (I-i) include but are not limited to those wherein $R^5$ is hydrogen and $G^2$ is optionally substituted piperazinyl.

Non limiting examples of compounds of formula (I) and (I-i) include, but are not limited to, 5-bromo-$N^2$-[4-(4-ethylpiperazin-1-yl)phenyl]-$N^4$-[2-(trifluoromethyl)-1H-benzimidazol-5-yl]pyrimidine-2,4-diamine;
$N^4$-(2-benzyl-1H-benzimidazol-5-yl)-5-bromo-$N^2$-[4-(4-ethylpiperazin-1-yl)phenyl]pyrimidine-2,4-diamine;
5-bromo-$N^2$-[4-(4-ethylpiperazin-1-yl)phenyl]-$N^4$-[2-(2-phenylethyl)-1H-benzimidazol-5-yl]pyrimidine-2,4-diamine;
$N^4$-(1-benzyl-1H-benzimidazol-5-yl)-5-bromo-$N^2$-[4-(4-ethylpiperazin-1-yl)phenyl]pyrimidine-2,4-diamine;
$N^4$-(1-benzyl-1H-benzimidazol-6-yl)-5-bromo-$N^2$-[4-(4-ethylpiperazin-1-yl)phenyl]pyrimidine-2,4-diamine;
5-bromo-$N^2$-[4-(4-ethylpiperazin-1-yl)phenyl]-$N^4$-(2-methyl-1H-benzimidazol-4-yl)pyrimidine-2,4-diamine;
5-bromo-$N^2$-[4-(4-ethylpiperazin-1-yl)phenyl]-$N^4$-1H-indazol-5-ylpyrimidine-2,4-diamine;
5-chloro-$N^2$-[4-(4-ethylpiperazin-1-yl)phenyl]-$N^4$-1H-indazol-5-ylpyrimidine-2,4-diamine;
$N^2$-[4-(4-ethylpiperazin-1-yl)phenyl]-$N^4$-1H-indazol-5-yl-5-methylpyrimidine-2,4-diamine;
2-{[4-(4-ethylpiperazin-1-yl)phenyl]amino}-4-(1H-indazol-5-ylamino)pyrimidine-5-carbonitrile;
$N^2$-[4-(4-ethylpiperazin-1-yl)phenyl]-$N^4$-1H-indazol-5-yl-5-(trifluoromethyl)pyrimidine-2,4-diamine;
5-bromo-$N^2$-{4-[4-(dimethylamino)piperidin-1-yl]-2-methoxyphenyl}-$N^4$-1H-indazol-5-ylpyrimidine-2,4-diamine;
5-bromo-$N^4$-1H-indazol-5-yl-$N^2$-{2-methoxy-4-[4-(4-methylpiperazin-1-yl)piperidin-1-yl]phenyl}pyrimidine-2,4-diamine;
$N^4$-1,3-benzothiazol-5-yl-5-bromo-$N^2$-[4-(4-ethylpiperazin-1-yl)phenyl]pyrimidine-2,4-diamine;
5-bromo-$N^2$-[4-(4-ethylpiperazin-1-yl)phenyl]-$N^4$-(2-methyl-1,3-benzoxazol-4-yl)pyrimidine-2,4-diamine;
5-bromo-$N^2$-{4-[4-(dimethylamino)piperidin-1-yl]-2-methoxyphenyl}-$N^4$-(2-methyl-1H-benzimidazol-4-yl)pyrimidine-2,4-diamine;
5-chloro-$N^2$-{4-[4-(dimethylamino)piperidin-1-yl]-2-methoxyphenyl}-$N^4$-(2-methyl-1H-benzimidazol-4-yl)pyrimidine-2,4-diamine;
5-chloro-$N^2$-{4-[4-(dimethylamino)piperidin-1-yl]-2-methoxyphenyl}-$N^4$-(1-methyl-1H-indazol-5-yl)pyrimidine-2,4-diamine;
5-bromo-$N^2$-{4-[4-(dimethylamino)piperidin-1-yl]-2-methoxyphenyl}-$N^4$-(1-methyl-1H-indazol-5-yl)pyrimidine-2,4-diamine;
5-bromo-$N^4$-(6-chloro-1H-indazol-5-yl)-$N^2$-{4-[4-(dimethylamino)piperidin-1-yl]-2-methoxyphenyl}pyrimidine-2,4-diamine;
5-bromo-$N^2$-{4-[4-(dimethylamino)piperidin-1-yl]-2-methoxyphenyl}-$N^4$-(6-methyl-1H-indazol-5-yl)pyrimidine-2,4-diamine;
5-bromo-$N^2$-{4-[4-(dimethylamino)piperidin-1-yl]-2-methoxyphenyl}-$N^4$-(2-methyl-1,3-benzothiazol-5-yl)pyrimidine-2,4-diamine;
5-bromo-$N^2$-{4-[4-(dimethylamino)piperidin-1-yl]-2-methoxyphenyl}-$N^4$-[6-(isopropylsulfonyl)-1H-indazol-5-yl]pyrimidine-2,4-diamine;
5-bromo-$N^2$-{4-[4-(dimethylamino)piperidin-1-yl]-2-methoxyphenyl}-$N^4$-[6-(isopropylthio)-1H-indazol-5-yl]pyrimidine-2,4-diamine;
5-chloro-$N^2$-{4-[4-(dimethylamino)piperidin-1-yl]-2-methoxyphenyl}-$N^4$-(2-methyl-1,3-benzoxazol-5-yl)pyrimidine-2,4-diamine;
5-chloro-$N^2$-{4-[4-(dimethylamino)piperidin-1-yl]-2-methoxyphenyl}-$N^4$-[6-(isopropylsulfonyl)-1H-indazol-5-yl]pyrimidine-2,4-diamine;
5-bromo-$N^2$-{4-[4-(dimethylamino)piperidin-1-yl]-2-methoxyphenyl}-$N^4$-[6-(isopropylsulfonyl)-1-methyl-1H-indazol-5-yl]pyrimidine-2,4-diamine;
5-bromo-$N^4$-[6-(isopropylsulfonyl)-1-methyl-1H-indazol-5-yl]-$N^2$-{2-methoxy-4-[4-(4-methylpiperazin-1-yl)piperidin-1-yl]phenyl}pyrimidine-2,4-diamine;
5-bromo-$N^2$-{4-[4-(dimethylamino)piperidin-1-yl]-2-methoxyphenyl}-$N^4$-[6-(isopropylsulfonyl)-2-methyl-2H-indazol-5-yl]pyrimidine-2,4-diamine;
5-bromo-$N^2$-{4-[4-(dimethylamino)piperidin-1-yl]-2-methoxyphenyl}-$N^4$-[6-(ethylsulfonyl)-1H-indazol-5-yl]pyrimidine-2,4-diamine;
5-bromo-$N^2$-{4-[4-(dimethylamino)piperidin-1-yl]phenyl}-$N^4$-[6-(ethylsulfonyl)-1H-indazol-5-yl]pyrimidine-2,4-diamine;
5-bromo-$N^4$-[6-(ethylsulfonyl)-1H-indazol-5-yl]-$N^2$-(2-methoxy-4-morpholin-4-ylphenyl)pyrimidine-2,4-diamine;
5-bromo-$N^2$-{4-[4-(dimethylamino)piperidin-1-yl]-2-methoxyphenyl}-$N^4$-[6-(ethylsulfonyl)-1-methyl-1H-indazol-5-yl]pyrimidine-2,4-diamine;
5-bromo-$N^2$-{4-[4-(dimethylamino)piperidin-1-yl]-2-methoxyphenyl}-$N^4$-[1-methyl-6-(methylsulfonyl)-1H-indazol-5-yl]pyrimidine-2,4-diamine;
5-{[5-bromo-2-({4-[4-(dimethylamino)piperidin-1-yl]-2-methoxyphenyl}amino)pyrimidin-4-yl]amino}-N,1-dimethyl-1H-indazole-6-carboxamide;
5-bromo-$N^2$-{4-[4-(dimethylamino)piperidin-1-yl]phenyl}-$N^4$-[6-(ethylsulfonyl)-1-methyl-1H-indazol-5-yl]pyrimidine-2,4-diamine;
5-bromo-$N^2$-{4-[4-(dimethylamino)piperidin-1-yl]phenyl}-$N^4$-[1-methyl-6-(methylsulfonyl)-1H-indazol-5-yl]pyrimidine-2,4-diamine;

5-{[5-bromo-2-({4-[4-(dimethylamino)piperidin-1-yl]phenyl}amino)pyrimidin-4-yl]amino}-N,1-dimethyl-1H-indazole-6-carboxamide;

5-bromo-N⁴-[6-(ethylsulfonyl)-1-methyl-1H-indazol-5-yl]-N²-(2-methoxy-4-morpholin-4-ylphenyl)pyrimidine-2,4-diamine;

5-bromo-N²-(2-methoxy-4-morpholin-4-ylphenyl)-N⁴-[1-methyl-6-(methylsulfonyl)-1H-indazol-5-yl]pyrimidine-2,4-diamine;

5-({5-bromo-2-[(2-methoxy-4-morpholin-4-ylphenyl)amino]pyrimidin-4-yl}amino)-N,1-dimethyl-1H-indazole-6-carboxamide;

5-bromo-N⁴-[6-(ethylsulfonyl)-1-methyl-1H-indazol-5-yl]-N²-[4-(4-isopropylpiperazin-1-yl)-2-methoxyphenyl]pyrimidine-2,4-diamine;

5-bromo-N²-[4-(4-isopropylpiperazin-1-yl)-2-methoxyphenyl]-N⁴-[1-methyl-6-(methylsulfonyl)-1H-indazol-5-yl]pyrimidine-2,4-diamine;

5-[(5-bromo-2-{[4-(4-isopropylpiperazin-1-yl)-2-methoxyphenyl]amino}pyrimidin-4-yl)amino]-N,1-dimethyl-1H-indazole-6-carboxamide;

5-bromo-N²-[4-(1,1-dioxidothiomorpholin-4-yl)phenyl]-N⁴-[6-(ethylsulfonyl)-1-methyl-1H-indazol-5-yl]pyrimidine-2,4-diamine;

5-bromo-N⁴-[6-(ethylsulfonyl)-1-methyl-1H-indazol-5-yl]-N²-{2-methoxy-4-[4-(4-methylpiperazin-1-yl)piperidin-1-yl]phenyl}pyrimidine-2,4-diamine;

5-bromo-N²-{2-methoxy-4-[4-(4-methylpiperazin-1-yl)piperidin-1-yl]phenyl}-N⁴-(2-phenylquinolin-6-yl)pyrimidine-2,4-diamine;

5-bromo-N²-{2-methoxy-4-[4-(4-methylpiperazin-1-yl)piperidin-1-yl]phenyl}-N⁴-(2-phenylquinolin-7-yl)pyrimidine-2,4-diamine;

5-bromo-N²-{2-methoxy-4-[4-(4-methylpiperazin-1-yl)piperidin-1-yl]phenyl}-N⁴-quinolin-6-ylpyrimidine-2,4-diamine;

5-bromo-N²-{2-methoxy-4-[4-(4-methylpiperazin-1-yl)piperidin-1-yl]phenyl}-N⁴-quinolin-7-ylpyrimidine-2,4-diamine; and 5-bromo-N-{2-methoxy-4-[4-(4-methylpiperazin-1-yl)piperidin-1-yl]phenyl}-4-(quinolin-7-yloxy)pyrimidin-2-amine;

or pharmaceutically acceptable salts or solvates thereof.

Compounds of the present application may exist as stereoisomers wherein, asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, Pure Appl. Chem., 1976, 45: 13-30.

It will be appreciated that two or more asymmetric centers may be present in the present compounds, hence several diastereomers and enantiomers of the exemplified structures will often be possible, and that pure diastereomers and enantiomers represent preferred embodiments. It is intended that pure diasteromers, pure enantiomers, and mixtures thereof, are within the scope of the invention.

Various stereoisomers (including enantiomers and diastereomers) and mixtures thereof (including racemates) are contemplated. Individual stereoisomers of present compounds may be prepared synthetically from commercially available starting materials that contain asymmetric or chiral centers or by preparation of racemic mixtures followed by resolution of the individual stereoisomer using methods that are known to those of ordinary skill in the art. Examples of resolution are, for example, (i) attachment of a mixture of enantiomers to a chiral auxiliary, separation of the resulting mixture of diastereomers by recrystallization or chromatography, followed by liberation of the optically pure product; or (ii) separation of the mixture of enantiomers or diastereomers on chiral chromatographic columns.

Geometric isomers may exist in the present compounds. Thus various geometric isomers and mixtures thereof resulting from the disposition of substituents around a carbon-carbon double bond, a carbon-nitrogen double bond, a cycloalkyl group, or a heterocycle group are part of the invention. Substituents around a carbon-carbon double bond or a carbon-nitrogen bond are designated as being of Z or E configuration and substituents around a cycloalkyl or a heterocycle are designated as being of cis or trans configuration.

Within the present application it is to be understood that compounds disclosed herein may exist as individual tautomers or equilibrium mixtures thereof wherein a proton of a compound shifts from one atom to another, as illustrated below:

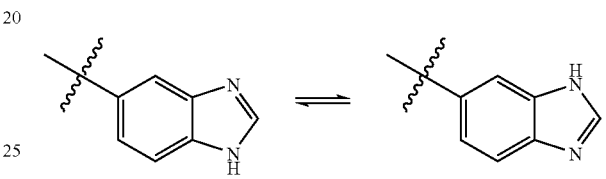

Though structural representations within this specification may show only one of the possible tautomeric or stereoisomeric forms, it is to be understood that the invention encompasses all tautomeric or stereoisomeric form, and mixtures thereof, and is not to be limited merely to any one tautomeric or stereoisomeric form utilized within the naming of the compounds or drawings.

The present compounds can exist in radiolabeled or isotope labeled form containing one or more atoms having an atomic mass or mass number different from the atomic mass or mass number most abundantly found in nature. Isotopes of atoms such as hydrogen, carbon, phosphorous, sulfur, fluorine, chlorine, and iodine include, but are not limited to, ²H, ³H, ¹⁴C, ³²P, ³⁵S, ¹⁸F, ³⁶Cl, and ¹²⁵I. Compounds that contain other radioisotopes of these and/or other atoms are within the scope of this invention. In one embodiment, the isotope-labeled compounds contain deuterium (²H), tritium (³H) or ¹⁴C radioisotopes. Isotope and radiolabeled compounds of this invention can be prepared by the general methods well known to persons having ordinary skill in the art. Such isotope and radiolabeled compounds can be conveniently prepared by carrying out the procedures disclosed in the above Examples and Schemes by substituting a readily available isotope or radiolabeled reagent for a non-labeled reagent. The isotope and radiolabeled compounds of the invention may be used as standards to determine the effectiveness of IGF-IR ligands or modulators in the binding assays. The isotope and radiolabeled compounds of the invention or pharmaceutically acceptable salts or solvates thereof may also be used for treating or preventing diseases or conditions described herein.

c. BIOLOGICAL DATA

The following example describes the assay that may be used to identify compounds having kinase activity.

IGF-1R kinase activity was assayed by a homogenous time-resolved fluorescence (HTRF) in vitro kinase assay (Mathis, G., *HTRF(R) Technology*. J Biomol Screen, 1999. 4(6): p. 309-314). Specifically, 10 μL C-terminal GSTtagged, recombinant, human IGF-1R, amino acids 954-1367 expressed by baculovirus in Sf21 cells (Cell Singaling Technology) was mixed with 10 µL inhibitor (various concentrations, 2% final DMSO) and 10 µL of ATP (50 µM final concentration) in reaction buffer (50 mM HEPES, pH 7.5, 10 mM MgCl$_2$, 2 mM MnCl$_2$, 0.1% BSA and 1 mM DTT, 40 µL final volume). The reaction was initiated by addition of 10 µL of biotinylated peptide substrate (Biotin-Ahx-AEEEYF-FLFA, 0.5 µM final concentration) in a black 384-well plate (Packard). After 60 minutes incubation at room temperature, the reaction was quenched by addition of 60 µL stop/revelation buffer to give 30 mM EDTA, 1 µg/mL streptavidin-APC (Prozyme), 50 ng/mL anti-phosphotyrosine mAb PT66-K Europium Cryptate, 30 mM HEPES, pH 7.5, 120 mM KF, 0.005% Tween-20, 0.05% BSA). The quenched reaction was allowed to stand at room temperature for 1 hour and then read in a time-resolved fluorescence detector (Envision, Perkin Elmer) at 615 nm and 665 nm simultaneously. The ratio between the signal of 615 nm and 665 nm was used in the calculation of the IC$_{50}$.

Table 1 demonstrates the utility of the representative examples of compounds described herein as inhibitors of IGF-1R kinases. In Table 1, "A" represents IC$_{50}$ of less than 10 nM; "B" represents IC$_{50}$ of between 10 nM and 50 nM; "C" represents IC$_{50}$ of between 51 nM and 100 nM; "D" represents IC$_{50}$ of between 101 nM and 500 nM; and "E" represents IC$_{50}$ of greater than 500 nM.

TABLE 1

| Example # | IC$_{50}$ |
|---|---|
| 1 | E |
| 2 | E |
| 3 | E |
| 4 | D |
| 5 | E |
| 6 | E |
| 7 | C |
| 8 | D |
| 9 | E |
| 10 | E |
| 11 | D |
| 12 | B |
| 13 | B |
| 14 | D |
| 15 | D |
| 16 | D |
| 17 | E |
| 18 | D |
| 19 | C |
| 20 | B |
| 21 | D |
| 22 | C |
| 23 | A |
| 24 | B |
| 25 | E |
| 26 | B |
| 27 | A |
| 28 | A |
| 29 | D |
| 30 | A |
| 31 | B |
| 32 | B |
| 33 | A |
| 34 | B |
| 35 | B |
| 36 | B |
| 37 | B |
| 38 | B |
| 39 | B |
| 40 | B |
| 41 | B |
| 42 | A |
| 43 | B |

TABLE 1-continued

| Example # | IC$_{50}$ |
|---|---|
| 44 | B |
| 45 | C |
| 46 | A |
| 47 | E |
| 48 | E |
| 49 | B |
| 50 | B |
| 51 | B |

Compounds assessed by the above-described assay were found to have IGF-1R inhibiting activity.

d. METHODS OF USING THE COMPOUNDS

In one aspect, the present invention provides methods of using one or more compounds or composition described herein to treat or prevent a disease or condition involving mediation, overexpression or disregulation of IGF-1R kinases in a mammal. In particular, compounds described herein are expected to have utility in treatment of diseases or conditions during which protein kinases such as IGF-1R kinase family members are expressed.

In one group of embodiments, diseases and conditions of humans or other animals that can be treated with inhibitors of IGF-1R kinases, include, but are not limited to, diseases involving overexpression or unregulation of a protein kinase family member such as but not limited to cancer. Cancers include, but are not limited to, hematologic and solid tumor types such as acoustic neuroma, acute leukemia, acute lymphoblastic leukemia, acute myelogenous leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer (including estrogen-receptor positive breast cancer), bronchogenic carcinoma, Burkitt's lymphoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, gastric carcinoma, germ cell testicular cancer, gestational trophobalstic disease, glioblastoma, head and neck cancer, heavy chain disease, hemangioblastoma, hepatoma, hepatocellular cancer, hormone insensitive prostate cancer, leiomyosarcoma, liposarcoma, lung cancer (including small cell lung cancer and non-small cell lung cancer), lymphangioendothelio-sarcoma, lymphangiosarcoma, lymphoblastic leukemia, lymphoma (lymphoma, including diffuse large B-cell lymphoma, follicular lymphoma, Hodgkin's lymphoma and non-Hodgkin's lymphoma), malignancies and hyperproliferative disorders of the bladder, breast, colon, lung, ovaries, pancreas, prostate, skin and uterus, lymphoid malignancies of T-cell or B-cell origin, leukemia, medullary carcinoma, medulloblastoma, melanoma, meningioma, mesothelioma, multiple myeloma, myelogenous leukemia, myeloma, myxosarcoma, neuroblastoma, oligodendroglioma, oral cancer, osteogenic sarcoma, ovarian cancer, pancreatic cancer, papillary adenocarcinomas, papillary carcinoma, peripheral T-cell lymphoma, pinealoma, polycythemia vera, prostate cancer (including hormone-insensitive (refractory) prostate cancer), rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), stomach cancer, squamous cell carcinoma, synovioma, sweat gland carcinoma, testicular cancer (including germ cell testicular cancer), thyroid cancer, Waldenström's macroglobulinemia, testicular tumors, uterine cancer, Wilms' tumor and the like.

It is also expected that compounds described herein would be useful in treating pediatric cancers or neoplasms including embryonal rhabdomyosarcoma, pediatric acute lymphoblastic leukemia, pediatric acute myelogenous leukemia, pediatric alveolar rhabdomyosarcoma, pediatric anaplastic ependymoma, pediatric anaplastic large cell lymphoma, pediatric anaplastic medulloblastoma, pediatric atypical teratoid/rhabdoid tumor of the central nervous system, pediatric biphenotypic acute leukemia, pediatric Burkitts lymphoma, pediatric cancers of Ewing's family of tumors such as primitive neuroectodermal rumors, pediatric diffuse anaplastic Wilm's tumor, pediatric favorable histology Wilm's tumor, pediatric glioblastoma, pediatric medulloblastoma, pediatric neuroblastoma, pediatric neuroblastoma-derived myelocytomatosis, pediatric pre-B-cell cancers (such as leukemia), pediatric psteosarcoma, pediatric rhabdoid kidney tumor, pediatric rhabdomyosarcoma, and pediatric T-cell cancers such as lymphoma and skin cancer and the like.

Involvement of IGF and IGFR in cancer is reported in Nature Reviews Cancer 8, 915 (2008).

The methods of the present invention typically involve administering to a subject in need of therapeutic treatment therapeutically effective amounts of one or more compound of formula (I). Therapeutically effective amounts of a compound having formula (I) depend on recipient of treatment, disease treated and severity thereof, composition comprising it, time of administration, route of administration, duration of treatment, potency, rate of clearance and whether or not another drug is co-administered. The amount of a compound having formula (I) used to make a composition to be administered daily to a patient in a single dose or in divided doses is from about 0.03 to about 200 mg/kg body weight. Single dose compositions contain these amounts or a combination of submultiples thereof.

e. COMBINATION THERAPY

Further provided herein are methods of using one or more compounds or composition of the invention in combination with one or more additional active agents. Compounds described herein are expected to be useful when used with:

alkylating agents, angiogenesis inhibitors, antibodies, antimetabolites, antimitotics, antiproliferatives, aurora kinase inhibitors, other apoptosis promoters (for example, Bcl-xL, Bcl-w and Bfl-1) inhibitors, Bcr-Abl kinase inhibitors, BiTE (Bi-Specific T cell Engager) antibodies, biologic response modifiers, cyclin-dependent kinase inhibitors, cell cycle inhibitors, cyclooxygenase-2 inhibitors, DVD Ig's, leukemia viral oncogene homolog (ErbB2) receptor inhibitors, growth factor inhibitors, heat shock protein (HSP)-90 inhibitors, histone deacetylase (HDAC) inhibitors, hormonal therapies, immunologicals, inhibitors of apoptosis proteins (IAP's) intercalating antibiotics, kinase inhibitors, mammalian target of rapamycin inhibitors, microRNA's mitogen-activated extracellular signal-regulated kinase inhibitors, multivalent binding proteins, non-steroidal anti-inflammatory drugs (NSAIDs), poly ADP (adenosine diphosphate)-ribose polymerase (PARP) inhibitors, platinum chemotherapeutics, polo-like kinase (Plk) inhibitors, proteosome inhibitors, purine analogs, pyrimidine analogs, receptor tyrosine kinase inhibitors, retinoids/deltoids plant alkaloids, small inhibitory ribonucleic acids (siRNA's), topoisomerase inhibitors, combinations thereof and the like.

A BiTE antibody is a bi-specific antibody that directs T-cells to attach cancer cells by simultaneously binding the two cells. The T-cell then attacks the target cancer cell. Exemplary BiTE antibodies include adecatumumab (Micromet MT201), blinatumomab (Micromet MT103) and the like.

SiRNA's are molecules having endogenous RNA bases or chemically modified nucleotides. The modifications shall not abolish cellular activity, but rather impart increased stability and/or increased cellular potency. Examples of chemical modifications include phosphorothioate groups, 2'-deoxynucleotide, 2'-OCH$_3$-containing ribonucleotides, 2'-F-ribonucleotides, 2'-methoxyethyl ribonucleotides or a combination thereof. The siRNA can have varying lengths (10-200 bps) and structures (hairpins, single/double strands, bulges, nicks/gaps, mismatches) and processed in the cell to provide active gene silencing. In certain embodiments, a double-stranded siRNA (dsRNA) can have the same number of nucleotides on each strand (blunt ends) or asymmetric ends (overhangs). The overhang of 1-2 nucleotides can be present on the sense and/or the antisense strand, as well as present on the 5'- and/or the 3'-ends of a given strand.

Multivalent binding proteins are binding proteins comprising two or more antigen binding sites. The multivalent binding protein is preferably engineered to have the three or more antigen binding sites and is generally not a naturally occurring antibody. The term "multispecific binding protein" means a binding protein capable of binding two or more related or unrelated targets. Dual variable domain (DVD) binding proteins are tetravalent or multivalent binding proteins binding proteins comprising two or more antigen binding sites. Such DVDs may be monospecific, i.e., capable of binding one antigen or multispecific, i.e., capable of binding two or more antigens. DVD binding proteins comprising two heavy chain DVD polypeptides and two light chain DVD polypeptides are referred to as DVD Ig. Each half of a DVD Ig comprises a heavy chain DVD polypeptide, a light chain DVD polypeptide, and two antigen binding sites. Each binding site comprises a heavy chain variable domain and a light chain variable domain with a total of 6 CDRs involved in antigen binding per antigen binding site.

Alkylating agents include altretamine, AMD-473, AP-5280, apaziquone, bendamustine, brostallicin, busulfan, carboquone, carmustine (BCNU), chlorambucil, CLORETAZINE® (laromustine, VNP 40101M), cyclophosphamide, decarbazine, estramustine, fotemustine, glufosfamide, ifosfamide, KW-2170, lomustine (CCNU), mafosfamide, melphalan, mitobronitol, mitolactol, nimustine, nitrogen mustard N-oxide, ranimustine, temozolomide, thiotepa, TREANDA® (bendamustine), treosulfan, rofosfamide and the like.

Angiogenesis inhibitors include endothelial-specific receptor tyrosine kinase (Tie-2) inhibitors, epidermal growth factor receptor (EGFR) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs, vascular endothelial growth factor receptor tyrosine kinase (VEGFR) inhibitors and the like. Antimetabolites include ALIMTA® (metrexed disodium, LY231514, MTA), 5-azacitidine, XELODA® (capecitabine), carmofur, LEUSTAT® (cladribine), clofarabine, cytarabine, cytarabine ocfosfate, cytosine arabinoside, decitabine, deferoxamine, doxifluridine, eflornithine, EICAR (5-ethynyl-1-β-D-ribofuranosylimidazole-4-carboxamide), enocitabine, ethnylcytidine, fludarabine, 5-fluorouracil alone or in combination with leucovorin, GEMZAR® (gemcitabine), hydroxyurea, ALKERAN® (melphalan), mercaptopurine, 6-mercaptopurine riboside, methotrexate, mycophenolic acid, nelarabine, nolatrexed, ocfosfate, pelitrexol, pentostatin, raltitrexed, Ribavirin, triapine, trimetrexate, S-1, tiazofurin, tegafur, TS-1, vidarabine, UFT and the like.

Bcl-2 proteins inhibitors include AT-101 ((−)gossypol), GENASENSE® (G3139 or oblimersen (Bcl-2-targeting antisense oligonucleotide)), IPI-194, IPI-565, N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide) (ABT-737), N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide (ABT-263), GX-070 (obatoclax) and the like.

Bcr-Abl kinase inhibitors include DASATINIB® (BMS-354825), GLEEVEC® (imatinib) and the like.

CDK inhibitors include AZD-5438, BMI-1040, BMS-032, BMS-387, CVT-2584, flavopyridol, GPC-286199, MCS-5A, PD0332991, PHA-690509, seliciclib (CYC-202, R-roscovitine), ZK-304709 and the like.

COX-2 inhibitors include ABT-963, ARCOXIA® (etoricoxib), BEXTRA® (valdecoxib), BMS347070, CELEBREX® (celecoxib), COX-189 (lumiracoxib), CT-3, DERAMAXX® (deracoxib), JTE-522, 4-methyl-2-(3,4-dimethylphenyl)-1-(4-sulfamoylphenyl-1H-pyrrole),
MK-663 (etoricoxib), NS-398, parecoxib, RS-57067, SC-58125, SD-8381, SVT-2016, S-2474, T-614, VIOXX® (rofecoxib) and the like.

EGFR inhibitors include ABX-EGF, anti-EGFR immunoliposomes, EGF-vaccine, EMD-7200, ERBITUX® (cetuximab), HR3, IgA antibodies, IRESSA® (gefitinib), TARCEVA® (erlotinib or OSI-774), TP-38, EGFR fusion protein, TYKERB® (lapatinib) and the like.

ErbB2 receptor inhibitors include CP-724-714, CI-1033 (canertinib), HERCEPTIN® (trastuzumab), TYKERB® (lapatinib), OMNITARG® (2C4, petuzumab), TAK-165, GW-572016 (ionafarnib), GW-282974, EKB-569, PI-166, dHER2 (HER2 vaccine), APC-8024 (HER-2 vaccine), anti-HER/2neu bispecific antibody, B7.her2IgG3, AS HER2 trifunctional bispecfic antibodies, mAB AR-209, mAB 2B-1 and the like. Histone deacetylase inhibitors include depsipeptide, LAQ-824, MS-275, trapoxin, suberoylanilide hydroxamic acid (SAHA), TSA, valproic acid and the like. HSP-90 inhibitors include 17-AAG-nab, 17-AAG, CNF-101, CNF-1010, CNF-2024, 17-DMAG, geldanamycin, IPI-504, KOS-953, MYCOGRAB® (human recombinant antibody to HSP-90), NCS-683664, PU24FC1, PU-3, radicicol, SNX-2112, STA-9090 VER49009 and the like.

Inhibitors of apoptosis proteins include ApoMab (a fully human affinity-matured IgG1 monoclonal antibody), antibodies that target TRAIL or death receptors (e.g., pro-apoptotic receptor agonists DR4 and DR5), conatumumab, ETR2-ST01, GDC0145, (lexatumumab), HGS-1029, LBY-135, PRO-1762 and tratuzumab.

MEK inhibitors include ARRY-142886, ARRY-438162 PD-325901, PD-98059 and the like.

mTOR inhibitors include AP-23573, CCI-779, everolimus, RAD-001, rapamycin, temsirolimus and the like.

Non-steroidal anti-inflammatory drugs include AMIGESIC® (salsalate), DOLOBID® (diflunisal), MOTRIN® (ibuprofen), ORUDIS® (ketoprofen), RELAFEN® (nabumetone), FELDENE® (piroxicam), ibuprofen cream, ALEVE® (naproxen) and NAPROSYN® (naproxen), VOLTAREN® (diclofenac), INDOCIN® (indomethacin), CLINORIL® (sulindac), TOLECTIN® (tolmetin), LODINE® (etodolac), TORADOL® (ketorolac), DAYPRO® (oxaprozin) and the like.

PDGFR inhibitors include C-451, CP-673, CP-868596 and the like. Platinum chemotherapeutics include cisplatin, ELOXATIN® (oxaliplatin) eptaplatin, lobaplatin, nedaplatin, PARAPLATIN® (carboplatin), satraplatin and the like. Polo-like kinase inhibitors include BI-2536 and the like.

Thrombospondin analogs include ABT-510, ABT-567, TSP-1 and the like.

VEGFR inhibitors include AVASTIN® (bevacizumab), ABT-869, AEE-788, ANGIOZYME™ (a ribozyme that inhibits angiogenesis (Ribozyme Pharmaceuticals (Boulder, Colo.) and Chiron, (Emeryville, Calif.)), axitinib (AG-13736), AZD-2171, CP-547,632, IM-862, MACUGEN (pegaptamib), NEXAVAR® (sorafenib, BAY43-9006), pazopanib (GW-786034), vatalanib (PTK-787, ZK-222584), SUTENT® (sunitinib, SU-11248), VEGF trap, ZACTIMA™ (vandetanib, ZD-6474) and the like.

Antibiotics include intercalating antibiotics aclarubicin, actinomycin D, amrubicin, annamycin, adriamycin, BLENOXANE® (bleomycin), daunorubicin, CAELYX® or MYOCET® (liposomal doxorubicin), elsamitrucin, epirbucin, glarbuicin, ZAVEDOS® (idarubicin), mitomycin C, nemorubicin, neocarzinostatin, peplomycin, pirarubicin, rebeccamycin, stimalamer, streptozocin, VALSTAR® (valrubicin), zinostatin and the like.

Topoisomerase inhibitors include aclarubicin, 9-aminocamptothecin, amonafide, amsacrine, becatecarin, belotecan, BN-80915, CAMPTOSAR® (irinotecan hydrochloride), camptothecin, CARDIOXANE® (dexrazoxine), diflomotecan, edotecarin, ELLENCE® or PHARMORUBICIN® (epirubicin), etoposide, exatecan, 10-hydroxycamptothecin, gimatecan, lurtotecan, mitoxantrone, orathecin, pirarbucin, pixantrone, rubitecan, sobuzoxane, SN-38, tafluposide, topotecan and the like.

Antibodies include AVASTIN® (bevacizumab), CD40-specific antibodies, chTNT-1/B, denosumab, ERBITUX® (cetuximab), HUMAX-CD4® (zanolimumab), IGF1R-specific antibodies, lintuzumab, PANOREX® (edrecolomab), RENCAREX® (WX G250), RITUXAN® (rituximab), ticilimumab, trastuzimab and and the like.

Hormonal therapies include ARIMIDEX® (anastrozole), AROMASIN® (exemestane), arzoxifene, CASODEX® (bicalutamide), CETROTIDE® (cetrorelix), degarelix, deslorelin, DESOPAN® (trilostane), dexamethasone, DROGENIL®, (flutamide), EVISTA® (raloxifene), AFEMA™ (fadrozole), FARESTON® (toremifene), FASLODEX® (fulvestrant), FEMARA® (letrozole), formestane, glucocorticoids, HECTOROL® (doxercalciferol), RENAGEL® (sevelamer carbonate), lasofoxifene, leuprolide acetate, MEGACE® (megesterol), MIFEPREX® (mifepristone), NILANDRON™ (nilutamide), NOLVADEX® (tamoxifen citrate), PLENAXIS™ (abarelix), prednisone, PROPECIA® (finasteride), rilostane, SUPREFACT® (buserelin), TRELSTAR® (luteinizing hormone releasing hormone (LHRH)), VANTAS® (Histrelin implant), VETORYL® (trilostane or modrastane), ZOLADEX® (fosrelin, goserelin) and the like.

Deltoids and retinoids include seocalcitol (EB1089, CB1093), lexacalcitrol (KH1060), fenretinide, PANRETIN® (aliretinoin), ATRAGEN® (liposomal tretinoin), TARGRETIN® (bexarotene), LGD-1550 and the like.

PARP inhibitors include ABT-888, olaparib, KU-59436, AZD-2281, AG-014699, BSI-201, BGP-15, INO-1001, ONO-2231 and the like.

Plant alkaloids include, but are not limited to, vincristine, vinblastine, vindesine, vinorelbine and the like.

Proteasome inhibitors include VELCADE® (bortezomib), MG132, NPI-0052, PR-171 and the like.

Examples of immunologicals include interferons and other immune-enhancing agents. Interferons include interferon alpha, interferon alpha-2a, interferon alpha-2b, interferon beta, interferon gamma-1a, ACTIMMUNE® (interferon gamma-1b), or interferon gamma-n1, combinations thereof and the like. Other agents include ALFAFERONE®, (IFN-α), BAM-002 (oxidized glutathione), BEROMUN® (tasonermin), BEXXAR® (tositumomab), CAMPATH® (alemtuzumab), CTLA4 (cytotoxic lymphocyte antigen 4), decarbazine, denileukin, epratuzumab, GRANOCYTE® (lenograstim), lentinan, leukocyte alpha interferon, imiquimod, MDX-010 (anti-CTLA-4), melanoma vaccine, mitumomab, molgramostim, MYLOTARG™ (gemtuzumab ozogamicin), NEUPOGEN® (filgrastim), OncoVAC-CL, OVAREX® (oregovomab), pemtumomab (Y-muHMFG1), PROVENGE® (sipuleucel-T), sargaramostim, sizofilan, teceleukin, THERACYS® (Bacillus Calmette-Guerin), ubenimex, VIRULIZIN® (immunotherapeutic, Lorus Pharmaceuticals), Z-100 (Specific Substance of Maruyama (SSM)), WF-10 (Tetrachlorodecaoxide (TCDO)), PROLEUKIN® (aldesleukin), ZADAXIN® (thymalfasin), ZENAPAX® (daclizumab), ZEVALIN® (90Y-Ibritumomab tiuxetan) and the like.

Biological response modifiers are agents that modify defense mechanisms of living organisms or biological responses, such as survival, growth, or differentiation of tissue cells to direct them to have anti-tumor activity and include include krestin, lentinan, sizofiran, picibanil PF-3512676 (CpG-8954), ubenimex and the like. Pyrimidine analogs include cytarabine (ara C or Arabinoside C), cytosine arabinoside, doxifluridine, FLUDARA® (fludarabine), 5-FU (5-fluorouracil), floxuridine, GEMZAR® (gemcitabine), TOMUDEX® (ratitrexed), TROXATYL™ (triacetyluridine troxacitabine) and the like.

Purine analogs include LANVIS® (thioguanine) and PURI-NETHOL® (mercaptopurine).

Antimitotic agents include batabulin, epothilone D (KOS-862), N-(2-((4-hydroxyphenyl)amino)pyridin-3-yl)-4-methoxybenzenesulfonamide, ixabepilone (BMS 247550), paclitaxel, TAXOTERE® (docetaxel), PNU100940 (109881), patupilone, XRP-9881 (larotaxel), vinflunine, ZK-EPO (synthetic epothilone) and the like.

Compounds described herein can also be used as radiosensitizeser that enhance the efficacy of radiotherapy. Examples of radiotherapy include external beam radiotherapy, teletherapy, brachtherapy and sealed, unsealed source radiotherapy and the like.

Additionally, compounds described herein may be combined with other chemptherapeutic agents such as ABRAXANE™ (ABI-007), ABT-100 (farnesyl transferase inhibitor), ADVEXIN® (Ad5CMV-p53 vaccine), ALTOCOR® or MEVACOR® (lovastatin), AMPLIGEN® (poly I:poly C12U, a synthetic RNA), APTOSYN® (exisulind), AREDIA® (pamidronic acid), arglabin, L-asparaginase, atamestane (1-methyl-3,17-dione-androsta-1,4-diene), AVAGE® (tazarotene), AVE-8062 (combreastatin derivative) BEC2 (mitumomab), cachectin or cachexin (tumor necrosis factor), canvaxin (vaccine), CEAVAC® (cancer vaccine), CELEUK® (celmoleukin), CEPLENE® (histamine dihydrochloride), CERVARIX® (human papillomavirus vaccine), CHOP® (C: CYTOXAN® (cyclophosphamide); H: ADRIAMYCIN® (hydroxydoxorubicin); O: Vincristine (ONCOVIN®); P: prednisone), CYPAT™ (cyproterone acetate), combrestatin A4P, DAB(389)EGF (catalytic and translocation domains of diphtheria toxin fused via a His-Ala linker to human epidermal growth factor) or TransMID-107R™ (diphtheria toxins), dacarbazine, dactinomycin, 5,6-dimethylxanthenone-4-acetic acid (DMXAA), eniluracil, EVIZON™ (squalamine lactate), DIMERICINE® (T4N5 liposome lotion), discodermolide, DX-8951f (exatecan mesylate), enzastaurin, EPO906 (epithilone B), GARDASIL® (quadrivalent human papillomavirus (Types 6, 11, 16, 18) recombinant vaccine), GASTRIMMUNE®, GENASENSE®, GMK (ganglioside conjugate vaccine), GVAX® (prostate cancer vaccine), halofuginone, histerelin, hydroxycarbamide, ibandronic acid, IGN-101, IL-13-PE38, IL-13-PE38QQR (cintredekin besudotox), IL-13-pseudomonas exotoxin, interferon-α, interferon-γ, JUNOVAN™ or MEPACT™ (mifamurtide), lonafarnib, 5,10-methylenetetrahydrofolate, miltefosine (hexadecylphosphocholine), NEOVASTAT® (AE-941), NEUTREXIN® (trimetrexate glucuronate), NIPENT® (pentostatin), ONCONASE® (a ribonuclease enzyme), ONCOPHAGE® (melanoma vaccine treatment), ONCOVAX® (IL-2 Vaccine), ORATHECIN™ (rubitecan), OSIDEM® (antibody-based cell drug), OVAREX® MAb (murine monoclonal antibody), paditaxel, PANDIMEX™ (aglycone saponins from ginseng comprising 20(S)protopanaxadiol (aPPD) and 20(S)protopanaxatriol (aPPT)), panitumumab, PANVAC®-VF (investigational cancer vaccine), pegaspargase, PEG Interferon A, phenoxodiol, procarbazine, rebimastat, REMOVAB® (catumaxomab), REVLIMID® (lenalidomide), RSR13 (efaproxiral), SOMATULINE® LA (lanreotide), SORIATANE® (acitretin), staurosporine (Streptomyces staurospores), talabostat (PT100), TARGRETIN® (bexarotene), TAXOPREXIN® (DHA-paclitaxel), TELCYTA® (canfosfamide, TLK286), temilifene, TEMODAR® (temozolomide), tesmilifene, thalidomide, THERATOPE® (STn-KLH), thymitaq (2-amino-3,4-dihydro-6-methyl-4-oxo-5-(4-pyridylthio)quinazoline dihydrochloride), TNFERADE™ (adenovector: DNA carrier containing the gene for tumor necrosis factor-α), TRACLEER® or ZAVESCA® (bosentan), tretinoin (Retin-A), tetrandrine, TRISENOX® (arsenic trioxide), VIRULIZIN®, ukrain (derivative of alkaloids from the greater celandine plant), vitaxin (anti-alphavbeta3 antibody), XCYTRIN® (motexafin gadolinium), XINLAY™ (atrasentan), XYOTAX™ (paclitaxel poliglumex), YONDELIS® (trabectedin), ZD-6126, ZINECARD® (dexrazoxane), ZOMETA® (zolendronic acid), zorubicin and the like.

Combination therapy includes administration of a single pharmaceutical dosage formulation containing one or more of the compounds and one or more additional pharmaceutical agents, as well as administration of the compounds and each additional pharmaceutical agent in its own separate pharmaceutical dosage formulation. For example, one or more active ingredients (including present compounds and additional pharmaceutical agents) may be administered to the patient together, in a single oral dosage composition having a fixed ratio of each active ingredient, such as a tablet or capsule; or each active ingredient may be administered in separate oral dosage formulations.

Separate dosage formulations may be administered at essentially the same time (e.g., concurrently) or at separately staggered times (e.g., sequentially).

f. PHARMACEUTICAL COMPOSITIONS

Pharmaceutical compositions comprising compounds described herein or pharmaceutically acceptable salts or solvates thereof are also provided. The pharmaceutical compositions comprise compounds of interest formulated together with one or more non-toxic pharmaceutically acceptable carriers.

Another aspect relates to pharmaceutical compositions comprising compounds described herein, or pharmaceutically acceptable salts or solvates thereof, and one or more pharmaceutically acceptable carriers, alone or in combination with one or more additional active agents.

The pharmaceutical compositions can be administered to humans and other mammals orally, rectally, parenterally, intracisternally, intravaginally, intraperitoneally, topically (as by powders, ointments or drops), bucally or as an oral or nasal spray. The term "parenterally" as used herein, refers to modes of administration which include intravenous, intramuscular, intraperitoneal, intrasternal, subcutaneous and intraarticular injection and infusion.

The term "pharmaceutically acceptable carrier" as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions for parenteral injection comprise pharmaceutically acceptable sterile aqueous or non-aqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents which delay absorption such as aluminum monostearate and gelatin.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds of this invention with suitable non-irritating carriers or carriers such as cocoa butter, polyethylene glycol or a suppository wax which are solid at room temperature but liquid at body temperature and therefore melt in the rectum or vaginal cavity and release the active compound.

Present compounds can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., Methods in Cell Biology, Volume XIV, Academic Press, New York, N.Y. (1976), p. 33 et seq.

Dosage forms for topical administration include powders, sprays, ointments and inhalants. The active compound may be mixed under sterile conditions with a pharmaceutically acceptable carrier and any needed preservatives, buffers or propellants which may be required. Opthalmic formulations, eye ointments, powders and solutions are also contemplated as being within the scope of this invention.

This invention also is directed, in part, to all salts of the compounds described herein. A salt of a compound may be advantageous due to one or more of the salt's properties, such as, for example, enhanced pharmaceutical stability in differing temperatures and humidities, or a desirable solubility in water or other solvents. Where a salt is intended to be administered to a patient, the salt preferably is pharmaceutically acceptable and/or physiologically compatible. Pharmaceutically acceptable salts include salts commonly used to form alkali metal salts and to form addition salts of free acids or free bases. In general, these salts typically may be prepared by conventional means by reacting, for example, the appropriate acid or base with a compound of the invention.

The phrase "pharmaceutically acceptable salt" means those salts which are, within the scope of sound medical judgment, suitable for use in contact with the tissues of humans and lower animals without undue toxicity, irritation, allergic response and the like and are commensurate with a reasonable benefit/risk ratio.

Pharmaceutically acceptable salts are well known in the art. For example, S. M. Berge et al. describe pharmaceutically acceptable salts in detail in (J. Pharmaceutical Sciences, 1977, 66: 1 et seq). The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, malate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid and citric acid.

Basic addition salts can be prepared in situ during the final isolation and purification of compounds of this invention by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like.

The present compounds may be modified by appending appropriate functionalities to enhance selective biological properties. Such modifications are known in the art and include those which increase biological penetration into a given biological compartment (e.g. blood, lymphatic system, central nervous system), increase oral bioavailability, increase solubility to allow administration by injection, alter metabolism, and alter rate of excretion.

The term "pharmaceutically acceptable prodrug" or "prodrug" as used herein, represents those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use.

Contemplated also are compounds formed by synthetic means or formed by in vivo biotransformation of a prodrug.

Compounds and their salts described herein can exist in unsolvated as well as solvated forms, including hydrated forms, such as hemi-hydrates. In general, the solvated forms, with pharmaceutically acceptable solvents such as water and ethanol among others are equivalent to the unsolvated forms.

g. GENERAL SYNTHESIS

This invention is intended to encompass compounds of the invention when prepared by synthetic processes or by metabolic processes. Preparation of the compounds by metabolic processes includes those occurring in the human or animal body (in vivo) or processes occurring in vitro.

The compounds of the invention may be prepared by a variety of processes well known for the preparation of compounds of this class. For example, the compounds of the invention wherein the variables have meanings as set forth in the summary section unless otherwise noted, can be synthesized as shown in Schemes 1 and 2.

Abbreviations which have been used in the descriptions of the Schemes and the Examples that follow are: DMF for N,N-dimethylformamide, DMSO for dimethyl sulfoxide, and TFA for trifluoroacetic acid.

The synthetic schemes depicted are not intended to comprise a comprehensive list of all means by which the compounds described and claimed herein may be synthesized. Further methods will be evident to those of ordinary skill in the art. Further, the various synthetic steps described below may be performed in an alternate sequence or order to give the desired compounds.

Compounds of general formula (I) wherein $L^1$ is NH can be prepared using general synthetic procedures as depicted in Scheme 1.

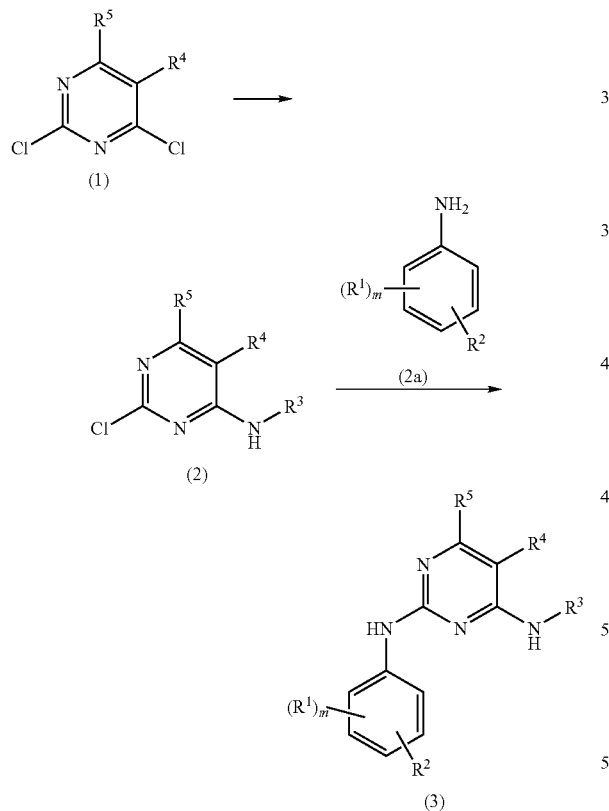

Dichloropyrimidines of formula (1) is treated with amines of formula $R^3NH_2$, in the presence of a base, such as sodium hydride, and a solvent such as DMF, at a temperature of about 0° C. to about room temperature to afford amines of formula (2).

Alternatively, the reaction can be effected in the presence of a base such as diisopropylethyl amine in a solvent such as n-butanol or isopropanol, at about room temperature to about 70° C.

Amines of formula (2) are reacted with amines of formula (2a), in a solvent such as n-butanol or isopropanol, and in the presence of an acid such as concentrated hydrochloric acid or hydrogen chloride in dioxane, and at a temperature from about 60° C. to about 100° C. to produce diamino-pyrimidines of formula (3).

Alternatively, the reaction can be performed in a solvent such as glacial acetic acid.

The coupling reaction between (2) and (2a) can also be accomplished in the presence of palladium acetate, a base such as but not limited to cesium carbonate, and 9,9-dimethyl-4,5-bis(diphenylphosphino)xanthane, in a solvent such as dioxane or N,N-dimethylformamide, at elevated temperature such as from about 90° C. to about 160° C., and optionally under microwave irradiation.

Compounds of formula general (I) wherein $L^1$ is O can be prepared using general procedure as illustrated in Scheme 2.

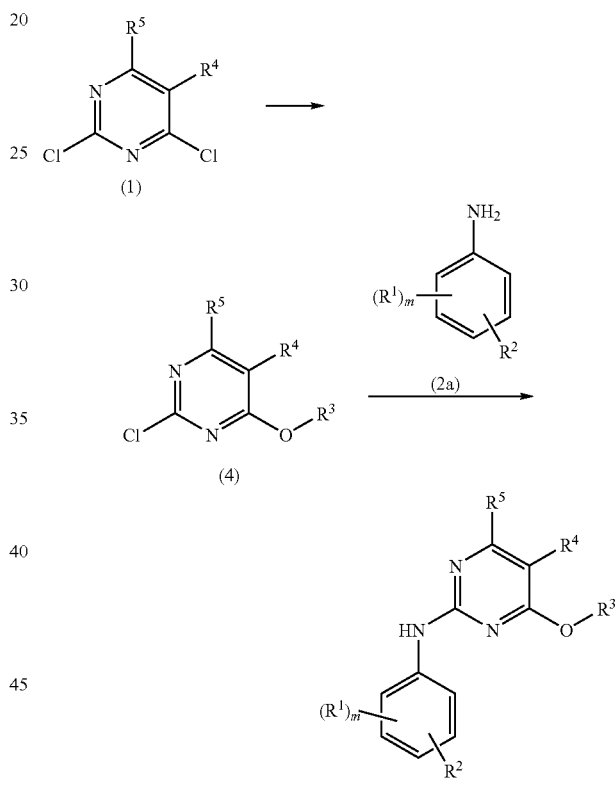

Dichloropyrimidines of formula (1) is coupled with alcohols of formula $R^3OH$, in the presence of a base, such as sodium carbonate or sodium hydride, and a solvent such as N,N-dimethylformamide, at a temperature of about 0° C. to about room temperature to provide ether of formula (4). Ether of formula (4) can be converted to compounds of formula (5) using the reaction conditions as described in Scheme 1 for the transformation of (2) to (3).

Amines of formula $R^3NH_2$ and that of formula (2a) are either commercially available, or can be prepared using methodologies known to those skilled in the art. Certain amines can also be prepared utilizing analogous reaction conditions as those described in the specific examples.

It will be appreciated that the synthetic schemes and specific examples as illustrated in the Examples section are illustrative and are not to be read as limiting the scope of the invention as it is defined in the appended claims. All alternatives, modifications, and equivalents of the synthetic methods and specific examples are included within the scope of the claims.

Optimum reaction conditions and reaction times for each individual step may vary depending on the particular reactants employed and substituents present in the reactants used. Unless otherwise specified, solvents, temperatures and other reaction conditions may be readily selected by one of ordinary skill in the art. Specific procedures are provided in the Examples section. The intermediates may be isolated or carried on in situ, with or without purification. Purification methods are known in the art and include, e.g. by eliminating the solvent from the residue and further purified according to methodologies generally known in the art such as, but not limited to, crystallization, distillation, extraction, trituration and chromatography (liquid and gas phase), reverse phase HPLC, and the like. Unless otherwise described, the starting materials and reagents are either commercially available or may be prepared by one skilled in the art from commercially available materials using methods described in the chemical literature.

Routine experimentations, including appropriate manipulation of the reaction conditions (e.g. temperature, duration, pressure, and atmosphere (inert gas, ambient)), reagents (e.g. additional reagents such as bases, catalysts, and salt forms of the reagents), and sequence of the synthetic route, protection of any chemical functionality that may not be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which may be found in T. Greene and P. Wuts, Protecting Groups in Organic Synthesis ($3^{rd}$ ed.), John Wiley & Sons, NY (1999), which is incorporated herein by reference in its entirety. Synthesis of the compounds of the invention may be accomplished by methods analogous to those described in the synthetic schemes described hereinabove and in specific examples.

Starting materials, if not commercially available, may be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound of the invention is required, it may be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound of the invention is required, it may be obtained by carrying out one of the above procedures using a pure geometric isomer as a starting material, or by resolution of a mixture of the geometric isomers of the compound or intermediates using a standard procedure such as chromatographic separation.

Following Examples may be used for illustrative purposes and should not be deemed to narrow the scope of the invention.

h. EXAMPLES

Example 1

5-bromo-$N^2$-[4-(4-ethylpiperazin-1-yl)phenyl]-$N^4$-[2-(trifluoromethyl)-1H-benzimidazol-5-yl]pyrimidine-2,4-diamine Example 1A To a mixture of 5-bromo-2,4-dichloropyrimidine (0.128 mL, 1.0 mmol) and 2-(trifluoromethyl)-1H-benzo[d]imidazol-5-amine (0.201 g, 1.000 mmol) in n-butanol (5 mL) was added N-ethyl-N-isopropylpropan-2-amine (0.206 mL, 1.5 mmol). The mixture was stirred at 100° C. for two hours and then cooled and concentrated to dryness. The residue was triturated with water and the resulting solid was dried in vacuum to provide the title compound (0.28 g, 71%). MS: (ESI(+)) m/e 393.6, 393.8 (M+H)$^+$.

Example 1B 5-bromo-$N^2$-[4-(4-ethylpiperazin-1-yl)phenyl]-$N^4$-[2-(trifluoromethyl)-1H-benzimidazol-5-yl]pyrimidine-2,4-diamine A scintillation vial was charged with EXAMPLE 1A (98 mg, 0.25 mmol), 4-(4-ethylpiperazin-1-yl)aniline (66.7 mg, 0.325 mmol), n-butanol (4 ml) and 4 N hydrogen chloride in dioxane (62.5 µL, 0.250 mmol). The mixture was stirred at 80° C. overnight. The reaction mixture was cooled and quenched with water (10 mL), adjusted to pH~13 with slow addition of conc. aq. NaOH. The mixture was extracted with ethyl acetate and the extract was concentrated. The crude product was purified with HPLC on a C18 reverse-phase column using a gradient of water and acetonitrile with 0.1% TFA as a buffer. The title compound was obtained as the TFA salt as an off-white solid (100 mg, 51%). MS: (ESI(+)) m/e 561.2, 563.2 (M+H)$^+$; $^1$H NMR (500 MHz, DMSO-d$_6$) δ ppm 9.53 (bs, 1H), 9.39 (s, 1H), 8.99 (s, 1H), 8.22 (s, 1H), 7.94 (s, 1H), 7.73 (d, 1H), 7.57 (d, 1H), 7.43 (d, 2H), 6.76 (d, 2H), 6.51 (s, 1H), 3.66-3.53 (m, 4H), 3.21-3.09 (m, 4H), 2.87 (t, 2H), 1.26 (q, 3H).

Example 2

$N^4$-(2-benzyl-1H-benzimidazol-5-yl)-5-bromo-$N^2$-[4-(4-ethylpiperazin-1-yl)phenyl]pyrimidine-2,4-diamine Example 2A The title compound was prepared according to the procedure of EXAMPLE 1A, substituting 2-benzyl-1H-benzo[d]imidazol-5-amine for 2-(trifluoromethyl)-1H-benzo[d]imidazol-5-amine. MS: (ESI(+)) m/e 413.9, 415.9 (M+H)$^-$.

Example 2B $N^4$-(2-benzyl-1H-benzimidazol-5-yl)-5-bromo-$N^2$-[4-(4-ethylpiperazin-1-yl)phenyl]pyrimidine-2,4-diamine The TFA salt of the title compound was prepared according to the procedure of EXAMPLE 1B, substituting EXAMPLE 2A for EXAMPLE 1A. MS: (ESI(+)) m/e 583.2, 585.2 (M+H)$^+$; $^1$H NMR (500 MHz, DMSO-d$_6$) δ ppm 9.80 (bs, 1H), 9.30 (s, 1H), 8.98 (s, 1H), 8.24 (s, 1H), 8.05 (s, 1H), 7.77-7.72 (m, 2H), 7.47-7.34 (m, 7H), 6.84 (d, 2H), 4.51 (s, 2H), 3.72-3.53 (m, 4H), 3.22 (t, 2H), 3.10-2.91 (m, 4H), 1.26 (q, 3H).

Example 3

5-bromo-$N^2$-[4-(4-ethylpiperazin-1-yl)phenyl]-$N^4$-[2-(2-phenylethyl)-1H-benzimidazol-5-yl]pyrimidine-2,4-diamine Example 3A The title compound was prepared according to the procedure of EXAMPLE 1A, substituting 2-phenethyl-1H-benzo[d]imidazol-5-amine for 2-(trifluoromethyl)-1H-benzo[d]imidazol-5-amine. MS: (ESI(+)) m/e 427.9, 419.9 (M+H)⁻.

Example 3B 5-bromo-$N^2$-[4-(4-ethylpiperazin-1-yl)phenyl]-$N^4$-[2-(2-phenylethyl)-1H-benzimidazol-5-yl]pyrimidine-2,4-diamine The TFA salt of title compound was prepared according to the procedure of EXAMPLE 1B, substituting EXAMPLE 3A for EXAMPLE 1A. MS: (ESI(+)) m/e 597.3, 599.3 (M+H)⁺; ¹H NMR (500 MHz, DMSO-$d_6$) δ ppm 9.82 (bs, 1H), 9.25 (s, 1H), 8.92 (s, 1H), 8.23 (s, 1H), 8.05 (s, 1H), 7.78-7.72 (m, 2H), 7.47 (d, 2H), 7.33-7.21 (m, 5H), 6.84 (d, 2H), 3.72-3.53 (m, 4H), 3.41 (t, 2H), 3.43 (t, 2H), 3.22 (t, 2H), 3.10-2.91 (m, 4H), 1.26 (q, 3H).

Example 4

$N^4$-(1-benzyl-1-benzimidazol-5-yl)-5-bromo-$N^2$-[4-(4-ethylpiperazin-1-yl)phenyl]pyrimidine-2,4-diamine Example 4A The title compound was prepared according to the procedure of EXAMPLE 1A, substituting 1-benzyl-1H-benzo[d]imidazol-5-amine for 2-(trifluoromethyl)-1H-benzo[d]imidazol-5-amine. MS: (ESI(+)) m/e 413.9, 415.9 (M+H)⁻.

Example 4B $N^4$-(1-benzyl-1H-benzimidazol-5-yl)-5-bromo-$N^2$-[4-(4-ethylpiperazin-1-yl)phenyl]pyrimidine-2,4-diamine The title compound was prepared according to the procedure of EXAMPLE 1B, substituting EXAMPLE 4A for EXAMPLE 1A, with the exception that the crude product was purified by normal phase chromatography on a silica gel column eluted with 5% ammonia saturated methanol in CH₂Cl₂. MS: (ESI(+)) m/e 583.2, 585.2 (M+H)⁺; ¹H NMR (500 MHz, DMSO-$d_6$) δ ppm 8.94 (s, 1H), 8.48 (s, 1H), 8.40 (s, 1H), 8.10 (s, 1H), 7.84 (s, 1H), 7.48 (d, 1H), 7.38-7.27 (m, 8H), 6.64 (d, 2H), 5.51 (s, 2H), 2.97-2.94 (m, 4H), 2.50-2.46 (m, 4H), 2.37 (t, 2H), 1.03 (q, 3H).

Example 5

$N^4$-(1-benzyl-1H-benzimidazol-6-yl)-5-bromo-$N^2$-[4-(4-ethylpiperazin-1-yl)phenyl]pyrimidine-2,4-diamine Example 5A The title compound was prepared according to the procedure of EXAMPLE 1A, substituting 1-benzyl-1H-benzo[d]imidazol-6-amine for 2-(trifluoromethyl)-1H-benzo[d]imidazol-5-amine. MS: (ESI(+)) m/e 413.9, 415.9 (M+H).

Example 5B $N^4$-(1-benzyl-1H-benzimidazol-6-yl)-5-bromo-$N^2$-[4-(4-ethylpiperazin-1-yl)phenyl]pyrimidine-2,4-diamine The TFA salt of the title compound was prepared according to the procedure of EXAMPLE 1B, substituting EXAMPLE 5A for EXAMPLE 1A. MS: (ESI(+)) m/e 583.2, 585.3 (M+H)⁺; ¹H NMR (500 MHz, DMSO-$d_6$) δ ppm 9.82 (bs, 1H), 9.32 (s, 1H), 9.25 (s, 1H), 9.01 (s, 1H), 8.23 (s, 1H), 8.01 (s, 1H), 7.80 (d, 1H), 7.71 (d, 1H), 7.41 (d, 2H), 7.34-7.30 (m, 5H), 6.80 (d, 2H), 5.57 (s, 1H), 3.72-3.53 (m, 4H), 3.20 (t, 2H), 3.11-2.91 (m, 4H), 1.26 (q, 3H).

Example 6

5-bromo-$N^2$-[4-(4-ethylpiperazin-1-yl)phenyl]-$N^4$-(2-methyl-1H-benzimidazol-4-yl)pyrimidine-2,4-diamine Example 6A The title compound was prepared according to the procedure of EXAMPLE 1A, substituting 2-methyl-1H-benzo[d]imidazol-4-amine for 2-(trifluoromethyl)-1H-benzo[d]imidazol-5-amine. MS: (ESI(+)) m/e 337.8, 339.8 (M+H)⁻.

Example 6B 5-bromo-$N^2$-[4-(4-ethylpiperazin-1-yl)phenyl]-$N^4$-(2-methyl-1H-benzimidazol-4-yl)pyrimidine-2,4-diamine The title compound was prepared according to the procedure of EXAMPLE 1B, substituting EXAMPLE 6A for EXAMPLE 1A, with the exception that the crude product was purified by normal phase chromatography on a silica gel column eluted with 5% ammonia saturated methano in CH₂Cl₂. MS: (ESI(+)) m/e 507.0, 509.0 (M+H)⁺; ¹H NMR (500 MHz, DMSO-$d_6$) δ ppm 12.31 (s, 1H), 9.18 (s, 1H), 8.37 (s, 1H), 8.22 (s, 1H), 8.18 (s, 1H), 7.46 (d, 2H), 7.14 (d, 1H), 7.08 (d, 1H), 6.87 (d, 2H), 3.18 (s, 3H), 3.09-2.94 (m, 4H), 2.50-2.46 (m, 4H), 2.37 (t, 2H), 1.03 (q, 3H).

Example 7

5-bromo-$N^2$-[4-(4-ethylpiperazin-1-yl)phenyl]-$N^4$-1H-indazol-5-ylpyrimidine-2,4-diamine Example 7A The title compound was prepared according to the procedure of EXAMPLE 1A, substituting 5-amino-indole for 2-(trifluoromethyl)-1H-benzo[d]imidazol-5-amine. MS: (ESI(+)) m/e 321.8, 323.8 (M+H)⁺.

Example 7B 5-bromo-$N^2$-[4-(4-ethylpiperazin-1-yl)phenyl]-$N^4$-1H-indazol-5-ylpyrimidine-2,4-diamine The title compound was prepared according to the procedure of EXAMPLE 1B, substituting EXAMPLE 7A for EXAMPLE 1A, with the exception that the crude product was purified by normal phase chromatography on a silica gel column eluted with 5% ammonia saturated methanol in CH$_2$Cl$_2$. MS: (ESI(+)) m/e 493.1, 495.1 (M+H)⁺; $^1$H NMR (500 MHz, DMSO-d$_6$) δ ppm 13.00 (s, 1H), 8.94 (s, 1H), 8.53 (s, 1H), 8.11 (s, 1H), 8.01 (s, 1H), 7.94 (s, 1H), 7.53 (d, 1H), 7.46 (d, 1H), 7.32 (d, 2H), 6.60 (d, 2H), 2.99-2.96 (m, 4H), 2.50-2.46 (m, 4H), 2.35 (t, 2H), 1.03 (q, 3H).

Example 8

5-chloro-$N^2$-[4-(4-ethylpiperazin-1-yl)phenyl]-$N^4$-1H-indazol-5-ylpyrimidine-2,4-diamine

Example 8A

The title compound was prepared as described in EXAMPLE 1A substituting 2,4,5-trichloropyrimidine for 5-bromo-2,4-dichloropyrimidine and 1H-indazol-5-amine for 2-(trifluoromethyl)-1H-benzo[d]imidazol-5-amine. MS (DCI(+)) m/e 280 (M+H)⁺.

Example 8B 5-chloro-$N^2$-[4-(4-ethylpiperazin-1-yl)phenyl]-$N^4$-1H-indazol-5-ylpyrimidine-2,4-diamine The title compound was prepared as described in EXAMPLE 1B substituting EXAMPLE 8A for EXAMPLE 1A with the exception that the crude product was purified by medium pressure liquid chromatography on silica gel, eluting with a 1, 2.5, 5% 7N-methanolic ammonia in dichloromethane step gradient. MS (ESI(+)) m/e 449 (M+H)⁺, (ESI(−)) m/e 447 (M−H)⁻; $^1$H NMR (300 MHz, DMSO-d$_6$) δ ppm 13.02 (s, 1H), 8.98 (s, 1H), 8.79 (s, 1H), 8.04 (s, 1H), 8.00 (d, 2H), 7.44-7.58 (m, 2H), 7.35 (d, 2H), 6.64 (d, 2H), 2.92-3.04 (m, 4H), 2.43-2.50 (m, 4H), 2.36 (q, 2H), 1.03 (t, 3H).

Example 9

$N^2$-[4-(4-ethylpiperazin-1-yl)phenyl]-$N^4$-1H-indazol-5-yl-5-methylpyrimidine-2,4-diamine

Example 9A

The title compound was prepared as described in EXAMPLE 1A substituting 2,4-dichloro-5-methylpyrimidine for 5-bromo-2,4-dichloropyrimidine and 1H-indazol-5-amine for 2-(trifluoromethyl)-1H-benzo[d]imidazol-5-amine. MS (DCI(+)) m/e 260 (M+H)⁺.

Example 9B $N^2$-[4-(4-ethylpiperazin-1-yl)phenyl]-$N^4$-1H-indazol-5-yl-5-methylpyrimidine-2,4-diamine The title compound was prepared as described in EXAMPLE 1B substituting EXAMPLE 9A for EXAMPLE 1A with the exception that the crude product was purified by medium pressure liquid chromatography on silica gel, eluting with a 1, 2.5, 5% 7N-methanolic ammonia in dichloromethane step gradient. MS (ESI(+)) m/e 429 (M+H)⁺, (ESI(−)) m/e 427 (M−H)⁻; 1H NMR (300 MHz, DMSO-d$_6$) δ ppm 12.95 (s, 1H), 8.60 (s, 1H), 8.22 (s, 1H), 8.09 (s, 1H), 7.97 (s, 1H), 7.80 (s, 1H), 7.39-7.53 (m, 4H), 6.68 (d, 2H), 2.94-3.04 (m, 4H), 2.45-2.49 (m, 4H), 2.36 (q, 2H), 2.10 (s, 3H), 1.03 (t, 3H).

Example 10

2-{[4-(4-ethylpiperazin-1-yl)phenyl]amino}-4-(1H-indazol-5-ylamino)pyrimidine-5-carbonitrile

Example 10A

The title compound was prepared as described in EXAMPLE 1A substituting 2,4-dichloropyrimidine-5-carbonitrile for 5-bromo-2,4-dichloropyrimidine and 1H-indazol-5-amine for 2-(trifluoromethyl)-1H-benzo[d]imidazol-5-amine. MS (DCI(+)) m/e 271 (M+H)⁺.

Example 10B

2-{[4-(4-ethylpiperazin-1-yl)phenyl]amino}-4-(1H-indazol-5-ylamino)pyrimidine-5-carbonitrile The title compound was prepared as described in EXAMPLE 1B substituting EXAMPLE 10A for EXAMPLE 1A with the exception that the crude product was purified by medium pressure liquid chromatography on silica gel, eluting with a 1, 2.5, 5% 7N-methanolic ammonia in dichloromethane step gradient. MS (ESI(+)) m/e 440 (M+H)⁺, (ESI(−)) m/e 438 (M−H)⁻; $^1$H NMR (300 MHz, DMSO-d$_6$) δ ppm 13.05 (s, 1H), 9.66 (s, 1H), 9.46 (s, 1H), 8.42 (s, 1H), 8.02 (s, 1H), 7.88 (s, 1H), 7.50-7.55 (m, 1H), 7.42 (d, 1H), 7.32 (s, 2H), 6.56 (s, 2H), 2.95-3.04 (m, 4H), 2.44-2.49 (m, 4H), 2.36 (q, 2H), 1.03 (t, 3H).

Example 11

$N^2$-[4-(4-ethylpiperazin-1-yl)phenyl]-$N^4$-1H-indazol-5-yl-5-(trifluoromethyl)pyrimidine-2,4-diamine

Example 11A

The title compound was prepared as described in EXAMPLE 1A substituting 2,4-dichloro-5-(trifluoromethyl)pyrimidine for 5-bromo-2,4-dichloropyrimidine and 1H-indazol-5-amine for 2-(trifluoromethyl)-1H-benzo[d]imidazol-5-amine. MS (DCI(+)) m/e 314 (M+H)⁺.

Example 11B $N^2$-[4-(4-ethylpiperazin-1-yl)phenyl]-$N^4$-1H-indazol-5-yl-5-(trifluoromethyl)pyrimidine-2,4-diamine The title compound was prepared as described in EXAMPLE 1B substituting EXAMPLE 11A for EXAMPLE 1A with the exception that the crude product was purified by medium pressure liquid chromatography on silica gel, eluting with a 2.5, 5, 10% 7N-methanolic ammonia in dichloromethane step gradient. MS (ESI(+)) m/e 483 (M+H)⁺, (ESI(−)) m/e 481 (M−H)⁻; 1H NMR (300 MHz, DMSO-d$_6$) δ ppm 13.08 (s, 1H), 9.37 (s, 1H), 8.73 (s, 1H), 8.27 (s, 1H), 8.05 (s, 1H), 7.78 (s, 1H), 7.55 (d, 1H), 7.33 (d, 1H), 7.21 (s, 2H), 6.41 (s, 2H), 2.84-3.03 (m, 4H), 2.41-2.48 (m, 4H), 2.35 (q, 2H), 1.03 (t, 3H).

Example 12

5-bromo-$N^2$-{4-[4-(dimethylamino)piperidin-1-yl]-2-methoxyphenyl}-$N^4$-1H-indazol-5-ylpyrimidine-2,4-diamine

Example 12A

A solution of 4-fluoro-2-methoxy-1-nitrobenzene (1.711 g, 10 mmol), N,N-dimethylpiperidin-4-amine (1.410 g, 11.00 mmol) and N-ethyl-N-isopropylpropan-2-amine (3.48 ml, 20.00 mmol) in anhydrous N,N-dimethylformamide (25 mL) was stirred at 70° C. overnight. The mixture was cooled, concentrated and the residue was mixed with water (60 mL), adjusted to pH 12, then extracted with $CH_2Cl_2$. The crude product was purified on a silica gel column eluting with 7.5% methanol in $CH_2Cl_2$ saturated with $NH_3$ to give 2.76 g of a yellow oil which turned into a solid upon standing. (ESI(+)) m/e 280.1 $(M+H)^+$.

Example 12B

EXAMPLE 12A (2.7 g, 9.67 mmol), iron (2.70 g, 48.3 mmol) and ammonium chloride (0.517 g, 9.67 mmol) were mixed with absolute ethanol (20 mL) and water (5 mL). The mixture was refluxed for 2 hours and filtered through a nylon membrane. The filtrate was concentrated to remove most of ethanol. The aqueous solution was adjusted to pH 13-14 and extracted with $CH_2Cl_2$. The organic solution was dried ($MgSO_4$), filtered, and concentrated to give a brown solid. (ESI(+)) m/e 250.2 $(M+H)^+$.

Example 12C 5-bromo-$N^2$-{4-[4-(dimethylamino)piperidin-1-yl]-2-methoxyphenyl}-$N^4$-1H-indazol-5-ylpyrimidine-2,4-diamine A scintillation vial was charged with EXAMPLE 7A (243 mg, 0.75 mmol) and EXAMPLE 12B (224 mg, 0.9 mmol), glacial acetic acid (10 ml) and 4 N hydrogen chloride in dioxane (190 µL, 0.75 mmol). The mixture was stirred at 115° C. for 6 hours. The reaction mixture was cooled, and concentrated. The residue was taken up in water (10 mL). The mixture was adjusted to pH~13 (conc. aq. NaOH) and extracted with ethyl acetate. The crude product was purified with HPLC on a C18 reverse-phase column using a gradient of water and acetonitrile with 0.1% TFA as a buffer. The title compound was obtained as the TFA salt as an off-white solid. MS: (ESI(+)) m/e 537.2, 539.2 $(M+H)^+$; $^1$H NMR (500 MHz, DMSO-$d_6$) δ ppm 9.81 (bs, 1H), 9.75 (s, 1H), 9.21 (s, 1H), 8.29 (s, 1H), 8.06 (s, 1H), 7.89 (s, 1H), 7.55 (d, 1H), 7.42 (d, 1H), 7.26 (d, 1H), 6.63 (s, 1H), 6.20 (bs, 1H), 3.82-3.79 (m, 2H), 3.77 (s, 3H), 3.35-3.29 (m, 1H), 2.79 (s, 6H), 2.71-2.64 (m, 2H), 2.07-2.05 (m, 2H), 1.69-1.61 (m, 2H).

Example 13

5-bromo-$N^4$-1H-indazol-5-yl-$N^2$-{2-methoxy-4-[4-(4-methylpiperazin-1-yl)piperidin-1-yl]phenyl}pyrimidine-2,4-diamine The TFA salt of the title compound was prepared according to the procedure of EXAMPLE 12C, substituting EXAMPLE 47B for EXAMPLE 12B. MS: (ESI(+)) m/e 594.2, 596.2 $(M+H)^+$; $^1$H NMR (500 MHz, DMSO-$d_6$) δ ppm 13.02 (bs, 1H), 9.58 (s, 1H), 9.01 (s, 1H), 8.26 (s, 1H), 8.05 (s, 1H), 7.90 (s, 1H), 7.55 (d, 1H), 7.42 (d, 1H), 7.30 (d, 1H), 6.67 (s, 1H), 6.24 (bs, 1H), 3.85-3.79 (m, 6H), 3.78 (s, 3H), 3.63-3.18 (m, 4H), 3.17-3.10 (m, 1H), 2.84 (s, 3H), 2.75-2.70 (m, 2H), 2.07-2.05 (m, 2H), 1.66-1.60 (m, 2H).

Example 14

$N^4$-1,3-benzothiazol-5-yl-5-bromo-$N^2$-[4-(4-ethylpiperazin-1-yl)phenyl]pyrimidine-2,4-diamine

Example 14A

The title compound was prepared according to the procedure of EXAMPLE 1A, substituting 5-amino-benzo[d]thiazole for 2-(trifluoromethyl)-1H-benzo[d]imidazol-5-amine. MS: (ESI(+)) m/e 340.8, 342.8 $(M+H)^+$.

Example 14B $N^4$-1,3-benzothiazol-5-yl-5-bromo-$N^2$-[4-(4-ethylpiperazin-1-yl)phenyl]pyrimidine-2,4-diamine The title compound was prepared according to the procedure of EXAMPLE 1B, substituting EXAMPLE 14A for EXAMPLE 1A, with the exception that the crude product was purified by normal phase chromatography on a silica gel column eluted with 5% ammonia saturated methanol in $CH_2Cl_2$. MS: (ESI(+)) m/e 510.1, 512.1 $(M+H)^+$; $^1$H NMR (500 MHz, DMSO-$d_6$) δ ppm 9.41 (s, 1H), 9.10 (s, 1H), 8.73 (s, 1H), 8.37 (s, 1H), 8.18 (s, 1H), 8.11 (d, 1H), 7.73 (d, 1H), 7.37 (d, 2H), 6.67 (d, 2H), 3.00-2.98 (m, 4H), 2.50-2.46 (m, 4H), 2.35 (t, 2H), 1.03 (q, 3H).

Example 15

5-bromo-$N^2$-[4-(4-ethylpiperazin-1-yl)phenyl]-$N^4$-(2-methyl-1,3-benzoxazol-4-yl)pyrimidine-2,4-diamine

Example 15A

The title compound was prepared according to the procedure of EXAMPLE 1A, substituting 2-methyl-4-aminobenzo[d]oxazole for 2-(trifluoromethyl)-1H-benzo[d]imidazol-5-amine. MS: (ESI(+)) m/e 338.8, 340.8 (M+H).

Example 15B 5-bromo-$N^2$-[4-(4-ethylpiperazin-1-yl)phenyl]-$N^4$-(2-methyl-1,3-benzoxazol-4-yl)pyrimidine-2,4-diamine The title compound was prepared according to the procedure of EXAMPLE 1B, substituting EXAMPLE 15A for EXAMPLE 1A, with the exception that the crude product was purified by normal phase chromatography on a silica gel column eluted with 5% ammonia saturated methanol in $CH_2Cl_2$. MS: (ESI(+)) m/e 508.0, 510.0 $(M+H)^+$; $^1$H NMR (500 MHz, DMSO-$d_6$) δ ppm 9.20 (s, 1H), 8.31 (s, 1H), 8.24 (s, 1H), 8.10 (bs, 1H), 7.42 (d, 1H), 7.33-7.27 (m, 3H), 6.79 (d, 2H), 3.06-3.04 (m, 4H), 2.61 (s, 3H), 2.50-2.46 (m, 4H), 2.35 (t, 2H), 1.03 (q, 3H).

Example 16

5-bromo-$N^2$-{4-[4-(dimethylamino)piperidin-1-yl]-2-methoxyphenyl}-$N^4$-(2-methyl-1H-benzimidazol-4-yl)pyrimidine-2,4-diamine The title compound was prepared according to the procedure of EXAMPLE 12C, substituting EXAMPLE 6A for EXAMPLE 7A, with the exception that the crude product was purified by normal phase chromatography on a silica gel column eluted with 5% ammonia saturated methanol in $CH_2Cl_2$. MS: (ESI(+)) m/e 551.1, 553.1 $(M+H)^+$; $^1$H NMR (500 MHz, DMSO-$d_6$) δ ppm 12.33 (s, 1H), 8.33 (s, 1H), 8.13 (s, 1H), 8.10 (s, 1H), 7.96 (s, 1H), 7.38 (d, 1H), 7.09 (d, 1H), 6.95 (t, 1H), 6.64 (d, 1H), 6.47 (dd, 1H), 3.82-3.79 (m, 2H), 3.75 (s, 3H), 2.70-2.66 (m, 2H), 2.21 (s, 6H), 2.19-2.18 (m, 1H), 1.86-1.80 (m, 2H), 1.55-1.47 (m, 2H).

Example 17

5-chloro-$N^2$-{4-[4-(dimethylamino)piperidin-1-yl]-2-methoxyphenyl}-$N^4$-(2-methyl-1H-benzimidazol-4-yl)pyrimidine-2,4-diamine

Example 17A

The title compound was prepared according to the procedure of EXAMPLE 1A, substituting 2,4,5-trichloro-pyrimidine for 5-bromo-2,4-dichloropyrimidine and 2-methyl-4-amino-benzimidazole for 2-(trifluoromethyl)-1H-benzo[d]imidazol-5-amine. MS: (ESI(+)) m/e 294.1, 296.1 $(M+H)^+$.

Example 17B 5-chloro-$N^2$-{4-[4-(dimethylamino)piperidin-1-yl]-2-methoxyphenyl}-$N^4$-(2-methyl-1H-benzimidazol-4-yl)pyrimidine-2,4-diamine The title compound was prepared according to the procedure of EXAMPLE 12C, substituting EXAMPLE 17A for EXAMPLE 7A, with the exception that the crude product was purified by normal phase chromatography on a silica gel column eluted with 5% ammonia saturated methanol in $CH_2Cl_2$. MS: (ESI(+)) m/e 507.2, 509.2 $(M+H)^+$; $^1$H NMR (500 MHz, DMSO-$d_6$) δ ppm 12.32 (s, 1H), 8.32 (s, 1H), 8.17 (s, 1H), 8.16 (s, 1H), 7.97 (s, 1H), 7.38 (d, 1H), 7.09 (d, 1H), 6.95 (t, 1H), 6.64 (d, 1H), 6.49 (dd, 1H), 3.78-3.71 (m, 2H), 3.75 (s, 3H), 2.70-2.66 (m, 2H), 2.21 (s, 6H), 2.19-2.18 (m, 1H), 1.86-1.80 (m, 2H), 1.55-1.47 (m, 2H).

Example 18

5-chloro-$N^2$-{4-[4-(dimethylamino)piperidin-1-yl]-2-methoxyphenyl}-$N^4$-(1-methyl-1H-indazol-5-yl)pyrimidine-2,4-diamine

Example 18A

The title compound was prepared according to the procedure of EXAMPLE 1A, substituting 2,4,5-trichloro-pyrimidine for 5-bromo-2,4-dichloropyrimidine and 1-methyl-5-amino-1H-indazole for 2-(trifluoromethyl)-1H-benzo[d]imidazol-5-amine. MS: (ESI(+)) m/e 291.8, 293.8 $(M+H)^+$.

Example 18B 5-chloro-$N^2$-{4-[4-(dimethylamino)piperidin-1-yl]-2-methoxyphenyl}-$N^4$-(1-methyl-1H-indazol-5-yl)pyrimidine-2,4-diamine The title compound was prepared according to the procedure of EXAMPLE 25B, substituting EXAMPLE 18A for EXAMPLE 25A. MS: (ESI(+)) m/e 507.2 $(M+H)^+$; $^1$H NMR (500 MHz, DMSO-$d_6$) δ ppm 9.97 (s, 1H), 9.90 (s, 1H), 9.32 (s, 1H), 8.25 (s, 1H), 8.01 (s, 1H), 7.93 (s, 1H), 7.65 (d, 1H), 7.52 (d, 1H), 7.28 (d, 1H), 6.67 (s, 1H), 6.32 (s, 1H), 4.06 (s, 3H), 3.92-3.83 (m, 2H), 3.78 (s, 3H), 3.35-3.30 (m, 1H), 2.79 (s, 6H), 2.73-2.68 (m, 2H), 2.09-2.07 (m, 2H), 1.71-1.63 (m, 2H).

Example 19

5-bromo-$N^2$-{4-[4-(dimethylamino)piperidin-1-yl]-2-methoxyphenyl}-$N^4$-(1-methyl-1H-indazol-5-yl)pyrimidine-2,4-diamine

Example 19A

The title compound was prepared according to the procedure of EXAMPLE 1A, substituting 1-methyl-5-amino-1H-indazole for 2-(trifluoromethyl)-1H-benzo[d]imidazol-5-amine. MS: (ESI(+)) m/e 337.8, 339.8 $(M+H)^-$.

Example 19B 5-bromo-$N^2$-{4-[4-(dimethylamino)piperidin-1-yl]-2-methoxyphenyl}-$N^4$-(1-methyl-1H-indazol-5-yl)pyrimidine-2,4-diamine The TFA salt of the title compound was prepared according to the procedure of EXAMPLE 12C, substituting EXAMPLE 19A for EXAMPLE 7A. MS: (ESI(+)) m/e 551.1, 553.1 $(M+H)^+$; $^1$H NMR (500 MHz, DMSO-$d_6$) δ ppm 9.70 (s, 1H), 9.54 (s, 1H), 8.94 (s, 1H), 8.25 (s, 1H), 8.00 (s, 1H), 7.90 (s, 1H), 7.64 (d, 1H), 7.48 (d, 1H), 7.29 (d, 1H), 6.64 (s, 1H), 6.23 (s, 1H), 4.06 (s, 3H), 3.92-3.83 (m, 2H), 3.77 (s, 3H), 3.34-3.28 (m, 1H), 2.79 (s, 6H), 2.70-2.65 (m, 2H), 2.08-2.06 (m, 2H), 1.71-1.63 (m, 2H).

Example 20

5-bromo-$N^4$-(6-chloro-1H-indazol-5-yl)-$N^2$-{4-[4-(dimethylamino)piperidin-1-yl]-2-methoxyphenyl}pyrimidine-2,4-diamine

Example 20A

The title compound was prepared according to the procedure of EXAMPLE 1A, substituting 5-amino-6-chloro-indazole for 2-(trifluoromethyl)-1H-benzo[d]imidazol-5-amine. MS: (ESI(+)) m/e 357.7, 359.7 $(M+H)^+$.

Example 20B 5-bromo-$N^4$-(6-chloro-1H-indazol-5-yl)-$N^2$-{4-[4-(dimethylamino)piperidin-1-yl]-2-methoxyphenyl}pyrimidine-2,4-diamine The TFA salt of the title compound was prepared according to the procedure of EXAMPLE 12C, substituting EXAMPLE 20A for EXAMPLE 7A. MS: (ESI(+)) m/e 571.0, 573.0 (M+H)$^+$; $^1$H NMR (500 MHz, DMSO-d$_6$) δ ppm 13.34 (bs, 1H), 9.63 (bs, 2H), 8.72 (bs, 1H), 8.28 (s, 1H), 8.14 (s, 1H), 7.97 (s, 1H), 7.84 (s, 1H), 7.10 (d, 1H), 6.56 (s, 1H), 5.84 (bs, 1H), 3.75 (s, 3H), 3.78-3.69 (m, 2H), 3.34-3.27 (m, 1H), 2.79 (s, 6H), 2.64-2.60 (m, 2H), 2.08-2.02 (m, 2H), 1.64-1.58 (m, 2H).

Example 21

5-bromo-N$^2$-{4-[4-(dimethylamino)piperidin-1-yl]-2-methoxyphenyl}-N$^4$-(6-methyl-1H-indazol-5-yl)pyrimidine-2,4-diamine Example 21A The title compound was prepared as described in EXAMPLE 12B substituting 6-methyl-5-nitro-1H-indazole for EXAMPLE 12A. MS (DCI(+)) m/e 148 (M+H)$^+$.

Example 21B

The title compound was prepared as described in EXAMPLE 1A substituting EXAMPLE 21A for 2-(trifluoromethyl)-1H-benzo[d]imidazol-5-amine. MS (ESI(+)) m/e 338, 340 (M+H)$^+$, (ESI(−)) m/e 336, 338 (M−H)$^-$.

Example 21C 5-bromo-N$^2$-{4-[4-(dimethylamino)piperidin-1-yl]-2-methoxyphenyl}-N$^4$-(6-methyl-1H-indazol-5-yl)pyrimidine-2,4-diamine The title compound was prepared as described in EXAMPLE 1B substituting EXAMPLE 21B for EXAMPLE 1A and EXAMPLE 12B for 4-(4-ethylpiperazin-1-yl)aniline with the exception that the crude product was purified by medium pressure liquid chromatography on silica gel, eluting with a 1.5, 4, 10% 7N-methanolic ammonia in dichloromethane step gradient. MS (ESI(+)) m/e 551, 553 (M+H)$^+$, (ESI(−)) m/e 549, 551 (M−H)$^-$; 1H NMR (300 MHz, DMSO-d$_6$) δ ppm 12.96 (s, 1H), 8.43 (s, 1H), 8.05-8.09 (m, 1H), 7.99 (s, 1H), 7.67-7.73 (m, 1H), 7.45 (s, 1H), 7.34 (s, 1H), 7.25 (d, 1H), 6.48 (d, 1H), 5.75 (s, 1H), 3.72 (s, 3H), 3.48 (d, 2H), 2.44-2.56 (m, 2H), 2.27 (s, 3H), 2.19 (s, 6H), 2.06-2.16 (m, 1H), 1.78 (s, 2H), 1.33-1.52 (m, 2H).

Example 22

5-bromo-N$^2$-{4-[4-(dimethylamino)piperidin-1-yl]-2-methoxyphenyl}-N$^4$-(2-methyl-1,3-benzothiazol-5-yl)pyrimidine-2,4-diamine Example 22A The title compound was prepared as described in EXAMPLE 1A substituting 2-methylbenzo[d]thiazol-5-amine for 2-(trifluoromethyl)-1H-benzo[d]imidazol-5-amine. MS (ESI(+)) m/e 355, 357 (M+H)$^+$, (ESI(−)) m/e 353, 355 (M−H)$^-$.

Example 22B 5-bromo-N$^2$-{4-[4-(dimethylamino)piperidin-1-yl]-2-methoxyphenyl}-N$^4$-(2-methyl-1,3-benzothiazol-5-yl)pyrimidine-2,4-diamine The title compound was prepared as described in EXAMPLE 1B substituting EXAMPLE 22A for EXAMPLE 1A and EXAMPLE 12B for 4-(4-ethylpiperazin-1-yl)aniline with the exception that the crude product was purified by medium pressure liquid chromatography on silica gel, eluting with a 1.5, 4, 10% 7N-methanolic ammonia in dichloromethane step gradient. MS (ESI(+)) m/e 568, 570 (M+H)$^+$, (ESI(−)) m/e 566, 568 (M−H)$^-$; 1H NMR (300 MHz, DMSO-d$_6$) δ ppm 8.65 (s, 1H), 8.18 (d, 1H), 8.11-8.15 (m, 1H), 7.89 (d, 1H), 7.84 (s, 1H), 7.54-7.62 (m, 1H), 7.44 (d, 1H), 6.58 (d, 1H), 6.27 (dd, 1H), 3.78 (s, 3H), 3.62 (d, 2H), 2.81 (s, 3H), 2.60 (t, 2H), 2.19 (s, 6H), 2.10-2.15 (m, 1H), 1.82 (d, 2H), 1.37-1.53 (m, 2H).

Example 23

5-bromo-N$^2$-{4-[4-(dimethylamino)piperidin-1-yl]-2-methoxyphenyl}-N$^4$-[6-(isopropylsulfonyl)-1H-indazol-5-yl]pyrimidine-2,4-diamine Example 23A A mixture of 6-fluoro-5-nitro-1H-indazole (543 mg, 3 mmol), propane-2-thiol (308 μL, 3.30 mmol) and cesium carbonate (977 mg, 3.00 mmol) in anhydrous 1-methyl-2-pyrrolidinone (5 mL) was stirred at 60° C. overnight and the quenched with water (30 mL). The mixture was extracted with dichloromethane. The organic solution was concentrated and the residue purified on a silica gel column, eluting with 60% ethyl acetate, to give the title compound as a yellow solid. 0.39 g, 54% yield. MS: (DCI/NH$_3$) m/e 238.0 (M+H)$^+$, 255.1 (M+NH$_4$)$^+$.

Example 23B

The title compound was prepared according to the procedure of 12B, substituting EXAMPLE 23A for EXAMPLE 12A. (DCI/NH$_3$) m/e 208.1 (M+H)$^+$.

Example 23C

The title compound was prepared according to the procedure of EXAMPLE 1A, substituting EXAMPLE 23B for 2-(trifluoromethyl)-1H-benzo[d]imidazol-5-amine. MS: (ESI(+)) m/e 395.8, 397.8 (M+H)$^+$.

Example 23D

To a mixture of EXAMPLE 23C (100 mg, 0.251 mmol) and dichloromethane (5 mL) was added 3-chlorobenzoperoxoic acid (155 mg, 0.627 mmol). After stirring at room temperature for 1 hour, the reaction mixture was quenched with 5% aqueous Na$_2$CO$_3$ solution and extracted with dichloromethane. The organic solution was concentrated and the residue was purified on a silica gel column eluting with 40% and 60% ethyl acetate to give the title compound. 63 mg, 58% yield. (ESI(+)) m/e 427.9, 429.9 (M+H)$^+$.

Example 23E 5-bromo-N$^2$-{4-[4-(dimethylamino)piperidin-1-yl]-2-methoxyphenyl}-N$^4$-[6-(isopropylsulfonyl)-1H-indazol-5-yl]pyrimidine-2,4-diamine The title compound was prepared according to the procedure of EXAMPLE 12C, substituting EXAMPLE 233D for EXAMPLE 7A, with the exception that the crude material was purified by normal phase chromatography on a silica gel column eluted with 5% ammonia saturated methanol in CH$_2$Cl$_2$. MS: (ESI(+)) m/e 643.2, 645.2 (M+H)$^+$; $^1$H NMR (500 MHz, DMSO-d$_6$) δ ppm 13.58 (s, 1H), 9.02 (s, 1H), 8.60 (s, 1H), 8.18 (s, 1H), 8.12-8.08 (m, 3H), 7.26 (d, 1H), 6.61 (s, 1H), 6.25 (bs, 1H), 3.72 (s, 3H), 3.74-3.66 (m, 2H), 3.45-3.42 (m, 1H), 2.66-2.62 (m, 2H), 2.21 (s, 6H), 2.16 (m, 1H), 1.86-1.84 (m, 2H), 1.53-1.48 (m, 2H), 1.16 (d, 6H).

Example 24

5-bromo-N$^2$-{4-[4-(dimethylamino)piperidin-1-yl]-2-methoxyphenyl}-N$^4$-[6-(isopropylthio)-1H-indazol-5-yl]pyrimidine-2,4-diamine The title compound was prepared according to the procedure of EXAMPLE 12C, substituting EXAMPLE 23C for EXAMPLE 7A, with the exception that the crude product was purified by normal phase chromatography on a silica gel column eluted with 5% ammonia saturated methanol in CH$_2$Cl$_2$. MS: (ESI(+)) m/e 611.2, 613.2 (M+H)$^+$; $^1$H NMR (500 MHz, DMSO-d$_6$) δ ppm 13.05 (s, 1H), 8.79 (s, 1H), 8.47 (s, 1H), 8.14 (s, 1H), 8.08 (s, 1H), 7.90 (s, 1H), 7.72 (s, 1H), 7.29 (d, 1H), 6.64 (s, 1H), 6.34 (d, 1H), 3.72 (s, 3H), 3.74-3.66 (m, 2H), 3.30-3.24 (m, 1H), 2.69-2.65 (m, 2H), 2.21 (s, 6H), 2.16 (m, 1H), 1.88-1.85 (m, 2H), 1.56-1.48 (m, 2H), 1.22 (d, 6H).

Example 25

5-chloro-N$^2$-{4-[4-(dimethylamino)piperidin-1-yl]-2-methoxyphenyl}-N$^4$-(2-methyl-1,3-benzoxazol-5-yl)pyrimidine-2,4-diamine

Example 25A

The title compound was prepared as described in EXAMPLE 1A substituting 2,4,5-trichloropyrimidine for 5-bromo-2,4-dichloropyrimidine and 2-methylbenzo[d]oxazol-5-amine for 2-(trifluoromethyl)-1H-benzo[d]imidazol-5-amine. MS (ESI(+)) m/e 295 (M+H)$^+$, (ESI(−)) m/e 293 (M−H)$^-$.

Example 25B 5-chloro-N$^2$-{4-[4-(dimethylamino)piperidin-1-yl]-2-methoxyphenyl}-N$^4$-(2-methyl-1,3-benzoxazol-5-yl)pyrimidine-2,4-diamine A 5 mL microwave vial was charged with EXAMPLE 25A (85 mg, 0.288 mmol), EXAMPLE 12B, palladium acetate (6.47 mg, 0.029 mmol), cesium carbonate (188 mg, 0.576 mmol), 9,9-dimethyl-4,5-bis(diphenylphosphino)xanthene (25.00 mg, 0.043 mmol) and dioxane (4 mL). The vial was purged with argon, sealed and microwave heated at 150° C. for 30 min. The reaction mixture was cooled, diluted with 50% brine (50 mL), and extracted with dichloromethane (3×50 mL). The combined organic layers were dried over sodium sulfate, filtered, concentrated and dried to a brown glass which was purified by medium pressure liquid chromatography on silica gel eluted with a 1, 2.5, 5, 10% 7N-methanolic ammonia in dichloromethane step gradient to give the title compound (72.5 mg, 50%). MS (ESI(+)) m/e 508 (M+H)$^+$, (ESI(−)) m/e 506 (M−H)$^-$; 1H NMR (300 MHz, DMSO-d$_6$) δ ppm 8.80 (s, 1H), 8.03 (s, 1H), 7.94 (s, 1H), 7.79 (s, 1H), 7.51-7.54 (m, 2H), 7.44 (d, 1H), 6.59 (d, 1H), 6.32 (dd, 1H), 3.78 (s, 3H), 3.64 (d, 2H), 2.57-2.67 (m, 5H), 2.22-2.26 (m, 6H), 2.10-2.17 (m, 1H), 1.82 (d, 2H), 1.47 (dd, 2H).

Example 26

5-chloro-N$^2$-{4-[4-(dimethylamino)piperidin-1-yl]-2-methoxyphenyl}-N$^4$-[6-(isopropylsulfonyl)-1H-indazol-5-yl]pyrimidine-2,4-diamine

Example 26A

The title compound was prepared according to the procedure of EXAMPLE 1A, substituting 2,4,5-trichloropyrimidine for 5-bromo-2,4-drichloropyrimidine and EXAMPLE 23B for 2-(trifluoromethyl)-1H-benzo[d]imidazol-5-amine. MS: (ESI(+)) m/e 353.8, 355.8 (M+H)$^+$.

Example 26B

The title compound was prepared according to the procedure of EXAMPLE 23D, substituting EXAMPLE 26A for EXAMPLE 23C. MS: (ESI(+)) m/e 383.9, 385.9 (M+H)$^+$.

Example 26C

The title compound was prepared according to the procedure of EXAMPLE 12C, substituting EXAMPLE 26B for EXAMPLE 7A, with the exception that the crude product was purified by normal phase chromatography on a silica gel column eluted with 5% ammonia saturated methanol in CH$_2$Cl$_2$. MS: (ESI(+)) m/e 599.2, 601.2 (M+H)$^+$; $^1$H NMR (500 MHz, DMSO-d$_6$) δ ppm 13.56 (s, 1H), 9.18 (s, 1H), 8.63 (s, 1H), 8.12-8.09 (m, 4H), 7.28 (d, 1H), 6.62 (s, 1H), 6.28 (d, 1H), 3.72 (s, 3H), 3.69-3.67 (m, 2H), 3.48-3.42 (m, 1H), 2.67-2.62 (m, 2H), 2.21 (s, 6H), 2.16 (m, 1H), 1.86-1.84 (m, 2H), 1.53-1.48 (m, 2H), 1.16 (d, 6H).

Example 27

5-bromo-N$^2$-{4-[4-(dimethylamino)piperidin-1-yl]-2-methoxyphenyl}-N$^4$-[6-(isopropylsulfonyl)-1-methyl-1H-indazol-5-yl]pyrimidine-2,4-diamine

Example 27A

A 100 mL flask was charged with sodium hydride (60% mineral oil dispersion, 0.100 g, 2.500 mmol) and tetrahydrofuran (20 mL). A solution of 6-fluoro-5-nitro-1H-indazole (0.362 g, 2.000 mmol) in tetrahydrofuran (10 mL) was added dropwise and the mixture was stirred for 30 minutes under nitrogen. The reaction mixture was cooled in an ice bath and a solution of iodomethane (0.498 ml, 8.00 mmol) in tetrahydrofuran (5 ml) was added dropwise. After stirring for 30 min, the ice bath was removed. The reaction was stirred for about 3 hours at ambient temperature, diluted with brine (80 ml), and extracted with ether (3×60 ml). The combined organics were dried over sodium sulfate, filtered, and concentrated to a brown solid which was purified by medium pressure liquid chromatography on silica gel eluted with a 10, 20, 40% ethyl acetate in hexanes step gradient to give the title compound 166 mg, 42%. MS (DCI(+)) m/e 196 (M+H)$^+$, 213 (M+NH$_4$)$^+$.

Example 27B

A 20 mL vial was charged with EXAMPLE 27A (520 mg, 2.66 mmol) and 1-methyl-2-pyrrolidinone (10 ml). To this was added sodium propane-2-thiolate (378 mg, 3.46 mmol). The vial was purged with argon, sealed, and heated at 60° C. overnight. The reaction mixture was cooled and concentrated.

The residue was partitioned between dichloromethane (75 mL) and 50% brine (75 mL). The aqueous layer was further extracted with dichloromethane (2×75 mL). The combined organic layers were dried over sodium sulfate, filtered, and concentrated to an oil which, upon trituration with water, yielded the title compound 585 mg, 87%. MS (DCI(+)) m/e 252 (M+H)$^+$.

Example 27C

The title compound was prepared as described in EXAMPLE 12B substituting EXAMPLE 27B for EXAMPLE 12A. MS (DCI(+)) m/e 222 (M+H)$^+$.

Example 27D

The title compound was prepared as described in EXAMPLE 1A substituting EXAMPLE 27C for 2-(trifluoromethyl)-1H-benzo[d]imidazol-5-amine. MS (ESI(+)) m/e 412,414 (M+H)$^+$, (ESI(–)) m/e 410, 414 (M–H)$^-$.

Example 27E

A 20 mL vial charged with EXAMPLE 27D (415 mg, 1.005 mmol) and dichloromethane (10 mL). To this was added 3-chlorobenzoperoxoic acid (70%, 620 mg, 2.51 mmol) and the vial was purged with argon, sealed and stirred at ambient temperature for 1 hour. The reaction mixture was quenched with excess 1M-sodium carbonate and then diluted with brine (70 mL) and dichloromethane (70 mL). The aqueous layer was further extracted with dichloromethane (2×50 mL). The combined organics were dried over sodium sulfate, filtered, and concentrated. The residue was purified by medium pressure liquid chromatography on silica gel eluted with a 0, 1, 2, 5% ethyl acetate in dichloromethane step gradient to give the title compound 362 mg, 81%. MS (ESI(–)) m/e 442, 444 (M–H)$^-$.

Example 27F 5-bromo-N$^2$-{4-[4-(dimethylamino)piperidin-1-yl]-2-methoxyphenyl}-N$^4$-[6-(isopropylsulfonyl)-1-methyl-1H-indazol-5-yl]pyrimidine-2,4-diamine The TFA salt of the title compound was prepared as described in EXAMPLE 1B substituting EXAMPLE 27E for EXAMPLE 1A and EXAMPLE 12B for 4-(4-ethylpiperazin-1-yl)aniline. MS (ESI(+)) m/e 657, 659 (M+H)$^+$, (ESI(–)) m/e 655, 657 (M–H)$^-$; $^1$H NMR (300 MHz, DMSO-d$_6$) δ ppm 9.08 (s, 1H), 8.60 (s, 1H), 8.16-8.24 (m, 2H), 8.08 (d, 2H), 7.27 (d, 1H), 6.61 (d, 1H), 6.29 (dd, 1H), 4.15 (s, 3H), 3.63-3.75 (m, 5H), 3.37-3.51 (m, 1H), 2.59-2.72 (m, 2H), 2.13-2.25 (m, 7H), 1.85 (d, 2H), 1.41-1.58 (m, 2H), 1.18 (d, 6H).

Example 28

5-bromo-N$^4$-[6-(isopropylsulfonyl)-1-methyl-1H-indazol-5-yl]-N$^2$-{2-methoxy-4-[4-(4-methylpiperazin-1-yl)piperidin-1-yl]phenyl}pyrimidine-2,4-diamine The title compound was prepared as described in EXAMPLE 1B substituting EXAMPLE 27E for EXAMPLE 1A and EXAMPLE 48B for 4-(4-ethylpiperazin-1-yl)aniline with the exception that the crude product was purified by medium pressure liquid chromatography on silica gel with a 1.5, 4, 6% 7N-methanolic ammonia in dichloromethane step gradient. MS (ESI(+)) m/e 712, 714 (M+H)$^-$, (ESI(–)) m/e 710, 712 (M–H)$^-$; $^1$H NMR (300 MHz, DMSO-d$_6$) δ ppm 9.08 (s, 1H), 8.60 (s, 1H), 8.16-8.24 (m, 2H), 8.07 (d, 2H), 7.27 (d, 1H), 6.61 (d, 1H), 6.28 (dd, 1H), 4.15 (s, 3H), 3.64-3.75 (m, 5H), 3.36-3.53 (m, 1H), 2.59-2.72 (m, 2H), 2.51 (s, 4H), 2.24-2.39 (m, 5H), 2.15 (s, 3H), 1.84 (s, 2H), 1.40-1.62 (m, 2H), 1.18 (d, 6H).

Example 29

5-bromo-N$^2$-{4-[4-(dimethylamino)piperidin-1-yl]-2-methoxyphenyl}-N$^4$-[6-(isopropylsulfonyl)-2-methyl-2H-indazol-5-yl]pyrimidine-2,4-diamine Example 29A The title compound was obtained as one of the isomeric products in EXAMPLE 27A. MS: DCI m/e 196.2 (M+H)$^+$.

Example 29B

A scintillation vial was charged with 6-fluoro-2-methyl-5-nitro-2H-indazole (0.37 g, 1.896 mmol), anhydrous 1-methyl-2-pyrrolidinone (10 mL) and sodium propane-2-thiolate (0.269 g, 2.465 mmol). The mixture was stirred at 60° C. for overnight. The mixture was concentrated to dryness and the residue was taken up in water (20 mL). The resulting solid was collected by filtration, washed with water and dried to provide a yellow solid (395 mg, 83%). MS: DCI m/e 252.1 (M+H)$^+$.

Example 29C

The title compound was prepared according to the procedure of EXAMPLE 12B, substituting EXAMPLE 29B for EXAMPLE 12A. MS: DCI m/e 222.0 (M+H)$^+$.

Example 29D

The title compound was prepared according to the procedure of EXAMPLE 1A, substituting EXAMPLE 29C for 2-(trifluoromethyl)-1H-benzo[d]imidazol-5-amine. MS: (ESI(+)) m/e 411.9, 413.9 (M+H)$^+$.

Example 29E

The title compound was prepared according to the procedure of EXAMPLE 23D, substituting EXAMPLE 29D for EXAMPLE 23C. MS: (ESI(+)) m/e 443.8, 445.8 (M+H)$^+$.

Example 29F

The title compound was prepared according to the procedure of EXAMPLE 12C, substituting EXAMPLE 29E for EXAMPLE 7A, with the exception that the crude product was purified by normal phase chromatography on a silica gel column eluted with 5% ammonia saturated methanol in CH$_2$Cl$_2$. MS: (ESI(+)) m/e 628.9, 630.9 (M+H)$^+$; $^1$H NMR (500 MHz, DMSO-d$_6$) δ ppm 8.97 (s, 1H), 8.51 (s, 1H), 8.35 (s, 1H), 8.19 (s, 1H), 8.17 (1H), 8.08 (s, 1H), 7.29 (d, 1H), 6.62 (s, 1H), 6.26 (d, 1H), 4.27 (s, 3H), 3.73 (s, 3H), 3.69-3.66 (m, 2H), 3.44-3.38 (m, 1H), 2.67-2.62 (m, 2H), 2.21 (s, 6H), 2.16 (m, 1H), 1.86-1.84 (m, 2H), 1.54-1.46 (m, 2H), 1.16 (d, 6H).

Example 30

5-bromo-$N^2$-{4-[4-(dimethylamino)piperidin-1-yl]-2-methoxyphenyl}-$N^4$-[6-(ethylsulfonyl)-1H-indazol-5-yl]pyrimidine-2,4-diamine

Example 30A

The title compound was prepared according to the procedure of EXAMPLE 29B, substituting 5-nitro-6-fluoro-1H-indazole for 6-fluoro-2-methyl-5-nitro-2H-indazole and sodium ethanethioalate for propane-2-thiolate. MS: DCI m/e 224.0 (M+H)$^+$, 241.1 (M+NH4)$^+$.

Example 30B

The title compound was prepared according to the procedure of EXAMPLE 12B, substituting EXAMPLE 30A for EXAMPLE 12A. MS: DCI m/e 194.0 (M+H)$^+$.

Example 30C

The title compound was prepared according to the procedure of EXAMPLE 1A, substituting EXAMPLE 30B for 2-(trifluoromethyl)-1H-benzo[d]imidazol-5-amine. MS: (ESI(+)) m/e 381.8, 383.8 (M+H)$^+$.

Example 30D

The title compound was prepared according to the procedure of EXAMPLE 23D, substituting EXAMPLE 30C for EXAMPLE 23C. MS: (ESI(+)) m/e 415.8, 417.8 (M+H)$^+$.

Example 30E

The title compound was prepared according to the procedure of EXAMPLE 12C, substituting EXAMPLE 30D for EXAMPLE 7A, with the exception that the crude product was purified by normal phase chromatography on a silica gel column eluted with 5% ammonia saturated methanol in CH$_2$Cl$_2$. MS: (ESI(+)) m/e 628.9, 630.9 (M+H)$^+$; $^1$H NMR (500 MHz, DMSO-d$_6$) δ ppm 13.58 (s, 1H), 8.93 (s, 1H), 8.60 (s, 1H), 8.53 (s, 1H), 8.19 (s, 1H), 8.15 (s, 1H), 8.08 (s, 1H), 7.26 (d, 1H), 6.60 (s, 1H), 6.19 (d, 1H), 3.73 (s, 3H), 3.66-3.63 (m, 2H), 3.31-3.29 (m, 1H), 2.64 (m, 2H), 2.21 (s, 6H), 2.16 (q, 2H), 1.85-1.83 (m, 2H), 1.52-1.45 (m, 2H), 1.08 (t, 3H).

Example 31

5-bromo-$N^2$-{4-[4-(dimethylamino)piperidin-1-yl]phenyl}-$N^4$-[6-(ethylsulfonyl)-1H-indazol-5-yl]pyrimidine-2,4-diamine A Biotage pressure vial was charged with EXAMPLE 30D (100 mg, 0.240 mmol), EXAMPLE 36B (97 mg, 0.480 mmol), iso-propyl alcohol (6 mL) and 4 N hydrogen chloride in dioxane (120 μL, 0.480 mmol). The dark homogeneous solution was stirred at 125° C. overnight (~16 hours) on a heating block behind a safety shield. The mixture was cooled and concentrated. The residue was re-dissolved in DMSO-methanol (50/50) and purified on a reverse-phase HPLC using a gradient of water-acetonitrile with 0.1% TFA as the buffer to provide the TFA salt of the title compound as an off-white solid. MS: (ESI(+)) m/e 599.1, 601.1 (M+H)$^+$; $^1$H NMR (500 MHz, DMSO-d$_6$) δ ppm 9.63 (s, 1H), 9.47 (s, 1H), 9.13 (s, 1H), 8.41 (s, 1H), 8.29 (s, 1H), 8.27 (s, 1H), 8.21 (s, 1H), 7.22 (d, 2H), 6.61 (d, 2H), 3.56-3.59 (m, 2H), 3.34 (q, 2H), 2.79 (s, 6H), 2.69-2.64 (m, 2H), 2.49-2.51 (m, 1H), 2.08-2.06 (m, 2H), 1.71-1.64 (m, 2H), 1.06 (t, 3H).

Example 32

5-bromo-$N^4$-[6-(ethylsulfonyl)-1H-indazol-5-yl]-$N^2$-(2-methoxy-4-morpholin-4-ylphenyl)pyrimidine-2,4-diamine The TFA salt of the title compound was prepared according to the procedure of EXAMPLE 31, substituting EXAMPLE 30D for EXAMPLE 29E and 2-methoxy-4-morpholinoaniline for EXAMPLE 36B. MS: (ESI(+)) m/e 588.0, 590.0 (M+H)$^+$; $^1$H NMR (500 MHz, DMSO-d$_6$) δ ppm 9.54 (s, 1H), 8.77 (s, 1H), 8.36 (s, 1H), 8.27 (s, 1H), 8.23 (s, 1H), 8.18 (s, 1H), 7.12 (d, 1H), 6.60 (d, 1H), 6.03 (bs, 1H), 3.74 (s, 3H), 3.77-3.70 (m, 4H), 3.34 (q, 2H), 3.12-3.05 (m, 4H), 1.07 (t, 3H).

Example 33

5-bromo-$N^2$-{4-[4-(dimethylamino)piperidin-1-yl]-2-methoxyphenyl}-$N^4$-[6-(ethylsulfonyl)-1-methyl-1H-indazol-5-yl]pyrimidine-2,4-diamine

Example 33A

The title compound was prepared as described in EXAMPLE 27B substituting sodium ethanethiolate for sodium propane-2-thiolate. MS (DCI(+)) m/e 238 (M+H)$^+$, 255 (M+NH4)$^+$.

Example 33B

The title compound was prepared as described in EXAMPLE 12B substituting EXAMPLE 33A for EXAMPLE 12A. MS (DCI(+)) m/e 208 (M+H)$^+$.

Example 33C

The title compound was prepared as described in EXAMPLE 1A substituting EXAMPLE 33B for 2-(trifluoromethyl)-1H-benzo[d]imidazol-5-amine. MS (ESI(+)) m/e 398, 400 (M+H)$^+$, (ESI(−)) m/e 396, 398 (M−H)$^-$.

Example 33D

The title compound was prepared as described in EXAMPLE 27E substituting EXAMPLE 33C for EXAMPLE 27D. MS (ESI(+)) m/e 430, 432 (M+H)$^+$, (ESI(−)) m/e 428, 430 (M−H)$^-$.

Example 33E 5-bromo-$N^2$-{4-[4-(dimethylamino)piperidin-1-yl]-2-methoxyphenyl}-$N^4$-[6-(ethylsulfonyl)-1-methyl-1H-indazol-5-yl]pyrimidine-2,4-diamine A 20 mL microwave vial charged with EXAMPLE 33D (100 mg, 0.232 mmol), EXAMPLE 12B (87 mg, 0.348 mmol), and 2-propanol (8 mL). To this was added hydrogen chloride (4N in dioxane, 0.232 mL, 0.929 mmol), the vial was purged with argon, sealed and heated at 125° C. for 24 hours. The reaction mixture was cooled, concentrated and the residue was purified by preparative reverse phase HPLC with a gradient of acetonitrile and 0.1% trifluoroacetic acid in water to provide the TFA salt of the title compound 112 mg, 64%.

MS (ESI(+)) m/e 643, 645 (M+H)⁺, (ESI(−)) m/e 641, 643 (M−H)⁻; 1H NMR (300 MHz, DMSO-d$_6$) δ ppm 9.55 (s, 1H), 9.30 (s, 1H), 8.43 (s, 1H), 8.28 (s, 1H), 8.25 (s, 1H), 8.14 (s, 1H), 7.20 (d, 1H), 6.63 (d, 1H), 6.13 (s, 1H), 4.18 (s, 3H), 3.81 (d, 2H), 3.75 (s, 3H), 3.25-3.41 (m, 3H), 2.80 (d, 6H), 2.66 (t, 2H), 2.05 (s, 2H), 1.59-1.75 (m, 2H), 1.07-1.13 (m, 3H).

Example 34

5-bromo-N²-{4-[4-(dimethylamino)piperidin-1-yl]-2-methoxyphenyl}-N⁴-[1-methyl-6-(methylsulfonyl)-1H-indazol-5-yl]pyrimidine-2,4-diamine Example 34A The title compound was prepared as described in EXAMPLE 27B substituting sodium methanethiolate for sodium propane-2-thiolate. MS (DCI(+)) m/e 224 (M+H)⁺, 241 (M+NH$_4$)⁺.

Example 34B

The title compound was prepared as described in EXAMPLE 12B substituting EXAMPLE 34A for EXAMPLE 12A. MS (DCI(+)) m/e 194 (M+H)⁺.

Example 34C

The title compound was prepared as described in EXAMPLE 1A substituting EXAMPLE 34B for 2-(trifluoromethyl)-1H-benzo[d]imidazol-5-amine. MS (ESI(+)) m/e 398, 400 (M+H)⁺, (ESI(−)) m/e 396, 398 (M−H)⁻.

Example 34D

The title compound was prepared as described in EXAMPLE 27E substituting EXAMPLE 34C for EXAMPLE 27D. MS (ESI(+)) m/e 416, 418 (M+H)⁺, (ESI(−)) m/e 414, 416 (M−H)⁻.

Example 34E 5-bromo-N²-{4-[4-(dimethylamino)piperidin-1-yl]-2-methoxyphenyl}-N⁴-[1-methyl-6-(methylsulfonyl)-1H-indazol-5-yl]pyrimidine-2,4-diamine The TFA salt of the title compound was prepared as described in EXAMPLE 33E substituting EXAMPLE 34D for EXAMPLE 33D. MS (ESI(+)) m/e 629, 631 (M+H)⁺; (ESI(−)) m/e 627, 629 (M−H)⁻; ¹H NMR (300 MHz, DMSO-d$_6$) δ ppm 9.50 (s, 1H), 9.25 (s, 1H), 8.40 (s, 1H), 8.32 (s, 1H), 8.24 (s, 1H), 8.15 (s, 1H), 7.21 (d, 1H), 6.62 (d, 1H), 6.12 (d, 1H), 4.18 (s, 3H), 3.76-3.82 (m, 2H), 3.76 (s, 3H), 3.29-3.36 (m, 1H), 3.27 (s, 3H), 2.80 (d, 6H), 2.65 (t, 2H), 2.06 (d, 2H), 1.57-1.75 (m, 2H).

Example 35

5-{[5-bromo-2-({4-[4-(dimethylamino)piperidin-1-yl]-2-methoxyphenyl}amino)pyrimidin-4-yl]amino}-N,1-dimethyl-1H-indazole-6-carboxamide Example 35A The title compound was prepared as described in EXAMPLE 27A substituting 6-chloro-5-nitro-1H-indazole for 6-fluoro-5-nitro-1H-indazole. MS (DCI(+)) m/e 212 (M+H)⁺, 229 (M+NH4)⁺.

Example 35B

A 20 mL microwave vial was charged with dibutyl vinylboronate (441 mg, 2.396 mmol), EXAMPLE 35A (338 mg, 1.597 mmol), cesium fluoride (728 mg, 4.79 mmol) and palladium tetrakis (185 mg, 0.160 mmol). Under argon the 1,2-dimethoxyethane (10 ml) and methanol (5.00 mL) were added. The vial was sealed and microwave heated at 155° C. for 25 minutes. The reaction mixture was cooled, and partitioned between 10% methanol in dichloromethane (100 ml) and 50% brine (100 ml). The aqueous layer was further extracted with dichloromethane. The combined organics were dried over sodium sulfate, filtered, and concentrated. The residue was purified medium pressure liquid chromatography on silica gel eluted with a 5, 15, 30, 60% ethyl acetate in hexane step gradient to give the title compound 276 mg, 85%. MS (DCI(+)) m/e 204 (M+H)⁻, 221 (M+NH4)⁺.

Example 35C

A 250 mL flask was charged with EXAMPLE 35B (925 mg, 4.55 mmol) and acetone (100 ml). To the resulting solution was added sodium bacarbonate (287 mg, 3.41 mmol) and potassium permanganate (2878 mg, 18.21 mmol). This mixture was stirred for 18 hours. 1M–HCl (about 125 mL) was added and stirring was continued for 5 hours at room temperature. The mixture was diluted with brine (150 ml) and extracted with ether (4×150 mL). The combined ether layers were dried over sodium sulfate, filtered, and concentrated. The residue was stirred in 1M-sodium hydroxide (100 mL), diluted with brine (100 mL) and extracted with 50% ethyl acetate/ether (3×100 mL). The aqueous layer was acidified with 2M-hydrochloric acid (100 mL) and was extracted with 10% methanol in dichloromethane (6×100 mL). The combined organics were dried over sodium sulfate, filtered, and concentrated to give the title compound (821 mg, 82%). MS (DCI(+)) m/e 239 (M+NH4)⁺.

Example 35D

A 100 mL flask charged with EXAMPLE 35C (816 mg, 3.69 mmol), dichloromethane (50 mL), and N,N-dimethylformamide (0.5 mL). This was cooled in an ice bath and oxalyl dichloride (0.612 ml, 7.01 mmol) was added dropwise. The ice bath was removed and the mixture was stirred for 2 hours. The reaction mixture was concentrated and the residue was dissolved in dichloromethane (50 ml) and added dropwise to an ice cooled solution of methanamine, (2M in tetrahydrofuran, 6.46 mL, 12.91 mmol) in dichloromethane (50 mL). The reaction mixture was stirred overnight under nitrogen while warming to ambient temperature. The reaction mixture was concentrated and the residue was purified by medium pressure liquid chromatography on silica gel eluted with a 1, 2.5, 5, 10% methanol in dichloromethane step gradient to give the title compound (388 mg, 45%). MS (DCI(+)) m/e 235 (M+H)⁺, 252 (M+NH4)⁺.

Example 35E

The title compound was prepared as described in EXAMPLE 12B substituting EXAMPLE 35D for EXAMPLE 12A. MS (DCI(+)) m/e 205 (M+H)⁺.

Example 35F

The title compound was prepared as described in EXAMPLE 1A substituting EXAMPLE 35E for 2-(trifluoromethyl)-1H-benzo[d]imidazol-5-amine. MS (ESI(+)) m/e 395, 397 (M+H)$^+$, (ESI(−)) m/e 393, 395 (M−H)$^−$.

Example 35G

The TFA salt of the title compound was prepared as described in EXAMPLE 33E substituting EXAMPLE 35F for EXAMPLE 33D. MS (ESI(+)) m/e 608, 610 (M+H)$^+$, (ESI(−)) m/e 606, 608 (M−H)$^−$; $^1$H NMR (300 MHz, DMSO-d$_6$) δ ppm 11.32 (s, 1H), 9.59 (s, 1H), 8.85-8.94 (m, 1H), 8.65 (s, 1H), 8.18-8.24 (m, 1H), 8.06 (s, 1H), 7.90 (s, 1H), 7.36 (d, 1H), 6.72 (d, 1H), 6.52 (dd, 1H), 4.07 (s, 3H), 3.87-3.98 (m, 2H), 3.75-3.78 (m, 3H), 3.27-3.42 (m, 1H), 2.85 (d, 3H), 2.81 (d, 6H), 2.69-2.77 (m, 2H), 2.09 (s, 2H), 1.63-1.79 (m, 2H).

Example 36

5-bromo-N$^2$-{4-[4-(dimethylamino)piperidin-1-yl]phenyl}-N$^4$-[6-(ethylsulfonyl)-1-methyl-1H-indazol-5-yl]pyrimidine-2,4-diamine Example 36A A 100 mL flask charged with 1-fluoro-4-nitrobenzene (2.122 mL, 20 mmol), DMSO (30 ml), N,N-dimethylpiperidin-4-amine (2.82 g, 22.00 mmol) and triethylamine (5.58 mL, 40.0 mmol). The mixture was heated at 100° C. under nitrogen for 22 hours. Upon cooling, the mixture was poured into stirring cold water (1000 mL) and the resulting solid was collected by filtration, washed with water, and dried to give the title compound (4.24 g, 85%). MS (ESI(+)) m/e 250 (M+H)$^+$, (ESI(−)) m/e 248 (M−H)$^−$.

Example 36B

The title compound was prepared as described in EXAMPLE 12B substituting EXAMPLE 36A for EXAMPLE 12A. MS (DCI(+)) m/e 220 (M+H)$^+$.

Example 36C 5-bromo-N$^2$-{4-[4-(dimethylamino)piperidin-1-yl]phenyl}-N$^4$-[6-(ethylsulfonyl)-1-methyl-1H-indazol-5-yl]pyrimidine-2,4-diamine The TFA salt of the title compound was prepared as in EXAMPLE 33E substituting EXAMPLE 36B for EXAMPLE 12B. MS (ESI(+)) m/e 613, 615 (M+H)$^+$, (ESI(−)) m/e 611, 613 (M−H)$^−$; 1H NMR (300 MHz, DMSO-d$_6$) δ ppm 9.32 (s, 1H), 9.00 (s, 1H), 8.44 (s, 1H), 8.31 (s, 1H), 8.24-8.27 (m, 1H), 8.21 (s, 1H), 7.26 (d, 2H), 6.62 (d, 2H), 4.20 (s, 3H), 3.64 (d, 2H), 3.21-3.39 (m, 3H), 2.79 (d, 6H), 2.61 (t, 2H), 2.04 (s, 2H), 1.57-1.77 (m, 2H), 1.09 (t, 3H).

Example 37

5-bromo-N$^2$-{4-[4-(dimethylamino)piperidin-1-yl]phenyl}-N$^4$-[1-methyl-6-(methylsulfonyl)-1H-indazol-5-yl]pyrimidine-2,4-diamine The TFA salt of the title compound was prepared as described in EXAMPLE 33E, substituting EXAMPLE 34D for EXAMPLE 33D and substituting EXAMPLE 36B for EXAMPLE 12B. MS (ESI(+)) m/e 599, 601 (M+H)$^+$, (ESI(−)) m/e 597, 599 (M−H)$^−$; 1H NMR (300 MHz, DMSO-d$_6$) δ ppm 9.31 (s, 1H), 8.98 (s, 1H), 8.41 (s, 1H), 8.35 (s, 1H), 8.25 (s, 1H), 8.22 (s, 1H), 7.25 (d, 2H), 6.62 (d, 2H), 4.20 (s, 3H), 3.64 (d, 2H), 3.27-3.34 (m, 1H), 3.26 (s, 3H), 2.79 (d, 6H), 2.61 (t, 2H), 2.05 (d, 2H), 1.58-1.75 (m, 2H).

Example 38

5-{[5-bromo-2-({4-[4-(dimethylamino)piperidin-1-yl]phenyl}amino)pyrimidin-4-yl]amino}-N,1-dimethyl-1H-indazole-6-carboxamide The TFA salt of the title compound was prepared as described in EXAMPLE 33E substituting EXAMPLE 35F for EXAMPLE 33D and substituting EXAMPLE 36B for EXAMPLE 12B. MS (ESI(+)) m/e 578, 580 (M+H)$^+$, (ESI(−)) m/e 576, 578 (M−H)$^−$; 1H NMR (300 MHz, DMSO-d$_6$) δ ppm 10.93 (s, 1H), 9.41 (s, 1H), 8.86 (d, 1H), 8.76 (s, 1H), 8.23 (s, 1H), 8.06 (s, 1H), 7.96 (s, 1H), 7.45 (d, 2H), 6.92 (d, 2H), 4.09 (s, 3H), 3.77 (d, 2H), 3.24-3.38 (m, 1H), 2.86 (d, 3H), 2.80 (d, 6H), 2.65-2.76 (m, 2H), 2.09 (d, 2H), 1.63-1.80 (m, 2H).

Example 39

5-bromo-N$^4$-[6-(ethylsulfonyl)-1-methyl-1H-indazol-5-yl]-N$^2$-(2-methoxy-4-morpholin-4-ylphenyl)pyrimidine-2,4-diamine The title compound was prepared as described in EXAMPLE 33E substituting 2-methoxy-4-morpholinoaniline for EXAMPLE 12B. MS (ESI(+)) m/e 602, 604 (M+H)$^+$, (ESI(−)) m/e 600, 602 (M−H)$^−$; 1H NMR (300 MHz, DMSO-d$_6$) δ ppm 9.52 (s, 1H), 8.72 (s, 1H), 8.38 (s, 1H), 8.29 (s, 1H), 8.26 (s, 1H), 8.16 (s, 1H), 7.15 (d, 1H), 6.61 (d, 1H), 6.10 (s, 1H), 4.18 (s, 3H), 3.69-3.79 (m, 7H), 3.36 (q, 2H), 3.01-3.11 (m, 4H), 1.10 (t, 3H).

Example 40

5-bromo-N$^2$-(2-methoxy-4-morpholin-4-ylphenyl)-N$^4$-[1-methyl-6-(methylsulfonyl)-1H-indazol-5-yl]pyrimidine-2,4-diamine The title compound was prepared as described in EXAMPLE 33E substituting EXAMPLE 34D for EXAMPLE 33D and substituting 2-methoxy-4-morpholinoaniline for EXAMPLE 12B. MS (ESI(+)) m/e 588, 590 (M+H)$^+$, (ESI(−)) m/e 586, 588 (M−H)$^−$; 1H NMR (300 MHz, DMSO-d$_6$) δ ppm 9.56 (s, 1H), 8.76 (s, 1H), 8.35 (s, 1H), 8.33 (s, 1H), 8.27 (s, 1H), 8.18 (s, 1H), 7.13 (d, 1H), 6.61 (d, 1H), 6.09 (s, 1H), 4.15-4.22 (m, 3H), 3.68-3.80 (m, 7H), 3.28 (s, 3H), 3.01-3.11 (m, 4H).

Example 41

5-({5-bromo-2-[(2-methoxy-4-morpholin-4-ylphenyl)amino]pyrimidin-4-yl}amino)-N,1-dimethyl-1H-indazole-6-carboxamide The title compound was prepared as described in EXAMPLE 33E substituting EXAMPLE 35F for EXAMPLE 33D and substituting 2-methoxy-4-morpholinoaniline for EXAMPLE 12B. MS (ESI(+)) m/e 588, 590 (M+H)$^+$, (ESI(−)) m/e 586, 588 (M−H)$^−$; $^1$H NMR (300 MHz, DMSO-d$_6$) δ ppm 11.60 (s, 1H), 9.17 (s, 1H), 8.87-8.98 (m, 1H), 8.63 (s, 1H), 8.24 (s, 1H), 8.08 (s, 1H), 7.93 (s, 1H), 7.32 (d, 1H), 6.72 (d, 1H), 6.52 (dd, 1H), 4.08 (s, 3H), 3.73-3.82 (m, 7H), 3.16-3.23 (m, 4H), 2.86 (d, 3H).

Example 42

5-bromo-$N^4$-[6-(ethylsulfonyl)-1-methyl-1H-indazol-5-yl]-$N^2$-[4-(4-isopropylpiperazin-1-yl)-2-methoxyphenyl]pyrimidine-2,4-diamine

Example 42A

The title compound was prepared as described in EXAMPLE 36A substituting 4-fluoro-2-methoxy-1-nitrobenzene for 1-fluoro-4-nitrobenzene and 1-isopropylpiperazine for N,N-dimethylpiperidin-4-amine. MS (DCI(+)) m/e 280 (M+H)⁻.

Example 42B

The title compound was prepared as described in EXAMPLE 12B substituting EXAMPLE 42A for EXAMPLE 12A. MS (DCI(+)) m/e 250 (M+H)⁺.

Example 42C 5-bromo-$N^4$-[6-(ethylsulfonyl)-1-methyl-1H-indazol-5-yl]-$N^2$-[4-(4-isopropylpiperazin-1-yl)-2-methoxyphenyl]pyrimidine-2,4-diamine The TFA salt of the title compound was prepared as described in EXAMPLE 33E substituting EXAMPLE 42B for EXAMPLE 12B. MS (ESI(+)) m/e 643, 645 (M+H)⁺, (ESI(-)) m/e 641, 643 (M-H)⁻; ¹H NMR (300 MHz, DMSO-d₆) δ ppm 9.24 (s, 1H), 8.45 (s, 1H), 8.33-8.41 (m, 1H), 8.29 (s, 1H), 8.25 (s, 1H), 8.15 (s, 1H), 7.29 (d, 1H), 6.68 (d, 1H), 6.16 (s, 1H), 4.19 (s, 3H), 3.82 (d, 2H), 3.76 (s, 3H), 3.57-3.65 (m, 1H), 3.53 (d, 2H), 3.36 (q, 2H), 3.07-3.22 (m, 2H), 2.92 (t, 2H), 1.32 (d, 6H), 1.07-1.14 (m, 3H).

Example 43

5-bromo-$N^2$-[4-(4-isopropylpiperazin-1-yl)-2-methoxyphenyl]-$N^4$-[1-methyl-6-(methylsulfonyl)-1H-indazol-5-yl]pyrimidine-2,4-diamine The TFA salt of the title compound was prepared as described in EXAMPLE 33E substituting EXAMPLE 34D for EXAMPLE 33D and substituting EXAMPLE 42B for EXAMPLE 12B. MS (ESI(+)) m/e 629, 631 (M+H)⁺, (ESI(-)) m/e 627, 629 (M-H)⁻; 1H NMR (300 MHz, DMSO-d₆) δ ppm 9.35 (s, 1H), 9.24 (s, 1H), 8.38-8.42 (m, 1H), 8.33 (s, 1H), 8.23-8.27 (m, 1H), 8.16 (s, 1H), 7.28 (d, 1H), 6.68 (d, 1H), 6.16 (s, 1H), 4.19 (s, 3H), 3.81 (d, 2H), 3.77 (s, 3H), 3.56-3.63 (m, 1H), 3.53 (d, 2H), 3.28 (s, 3H), 3.05-3.21 (m, 2H), 2.91 (t, 2H), 1.31 (d, 6H).

Example 44

5-[(5-bromo-2-{[4-(4-isopropylpiperazin-1-yl)-2-methoxyphenyl]amino}pyrimidin-4-yl)amino]-N,1-dimethyl-1H-indazole-6-carboxamide The TFA salt of the title compound was prepared as described in EXAMPLE 33E substituting EXAMPLE 35F for EXAMPLE 33D and substituting EXAMPLE 42B for EXAMPLE 12B. MS (ESI(+)) m/e 608, 610 (M+H)⁺, (ESI(-)) m/e 606, 608 (M-H)⁻; ¹H NMR (300 MHz, DMSO-d₆) δ ppm 11.24 (s, 1H), 9.44 (s, 1H), 8.89 (q, 1H), 8.67 (s, 1H), 8.22 (s, 1H), 8.06 (s, 1H), 7.92 (s, 1H), 7.45 (d, 1H), 6.78 (d, 1H), 6.53 (dd, 1H), 4.07 (s, 3H), 3.94 (d, 2H), 3.79 (s, 3H), 3.60-3.66 (m, 1H), 3.56 (d, 2H), 3.17 (d, 2H), 3.01 (t, 2H), 2.86 (d, 3H), 1.33 (d, 6H).

Example 45

5-bromo-$N^2$-[4-(1,1-dioxidothiomorpholin-4-yl)phenyl]-$N^4$-[6-(ethylsulfonyl)-1-methyl-1H-indazol-5-yl]pyrimidine-2,4-diamine The title compound was prepared as described in EXAMPLE 33E substituting 4-(4-aminophenyl)-thiomorpholine dioxide for EXAMPLE 12B. MS (ESI(+)) m/e 620, 622 (M+H)⁺, (ESI(-)) m/e 618, 620 (M-H)⁻; ¹H NMR (300 MHz, DMSO-d₆) δ ppm 9.35 (s, 1H), 9.07 (s, 1H), 8.41 (s, 1H), 8.31 (s, 1H), 8.26 (s, 1H), 8.23 (s, 1H), 7.26 (d, 2H), 6.65 (s, 2H), 4.21 (s, 3H), 3.58-3.63 (m, 4H), 3.34 (q, 2H), 3.05-3.11 (m, 4H), 1.08 (t, 3H).

Example 46

5-bromo-$N^4$-[6-(ethylsulfonyl)-1-methyl-1H-indazol-5-yl]-$N^2$-{2-methoxy-4-[4-(4-methylpiperazin-1-yl)piperidin-1-yl]phenyl}pyrimidine-2,4-diamine The TFA salt of the title compound was prepared as described in EXAMPLE 33E substituting EXAMPLE 47B for EXAMPLE 12B. MS (ESI(+)) m/e 698, 700 (M+H)⁺, (ESI(-)) m/e 696, 698 (M-H)⁻; 1H NMR (300 MHz, DMSO-d₆) δ ppm 9.35 (s, 1H), 8.46 (s, 1H), 8.42 (s, 1H), 8.29 (s, 1H), 8.26 (s, 1H), 8.14 (s, 1H), 7.22 (d, 1H), 6.66 (s, 1H), 6.18 (d, 1H), 4.18 (s, 3H), 3.75 (s, 5H), 3.51 (s, 2H), 3.36 (q, 2H), 3.09 (s, 5H), 2.82 (s, 3H), 2.65-2.78 (m, 2H), 2.44-2.49 (m, 2H), 2.03 (s, 2H), 1.54-1.74 (m, 2H), 1.10 (t, 3H).

Example 47

5-bromo-$N^2$-{2-methoxy-4-[4-(4-methylpiperazin-1-yl)piperidin-1-yl]phenyl}-$N^4$-(2-phenylquinolin-6-yl)pyrimidine-2,4-diamine

Example 47A 1-(1-(3-methoxy-4-nitrophenyl)piperidin-4-yl)-4-methylpiperazine In a 5 mL microwave tube was placed 4-fluoro-2-methoxy-1-nitrobenzene (0.638 g, 3.73 mmol), 1-methyl-4-(piperidin-4-yl)piperazine (0.888 g, 4.85 mmol), and triethylamine (1.559 ml, 11.18 mmol) in acetonitrile (12.43 ml) to give a yellow solution. The solution was heated in a Biotage microwave reactor at 130° C. for 30 minutes. The solvent was stripped off and the residue was placed under house vacuum. The yellow residue was purified by flash chromatography using an Argonaut Flashmaster Solo, using a gradient of 100% dichloromethane to 1:1 dichloromethane/methanol to afford a yellow solid. (ESI(+)) m/e 335.0 (M+H)⁺.

Example 47B 2-methoxy-4-(4-(4-methylpiperazin-1-yl)piperidin-1-yl)aniline

Into a 50 ml pressure bottle was charged EXAMPLE 47A (0.2476 g, 1.039 mmol), tetrahydrofuran (2 mL), ethanol (2 mL), hydrogen (30 psi), and 5% Pd—C, wet (0.050 g, 0.465 mmol). The mixture was stirred for 3 hours at room temperature and then checked by HPLC indicating no starting material present. The mixture was filtered through a nylon membrane and concentrated to afford a purple solid. (ESI(+)) m/e 305.1 (M+H)⁺.

Example 47C

N-(diphenylmethylene)-2-phenylquinolin-6-amine

In a 20 mL microwave tube was charged cesium carbonate (0.440 mL, 5.50 mmol), palladium(II)acetate (0.018 g, 0.079 mmol), and 9,9-dimethyl-4,5-bis(diphenylphosphino)xanthene (0.068 g, 0.118 mmol) in dioxane (6.0 mL) to give a yellow suspension. The mixture was stirred for 10 minutes and then triethylamine (0.016 mL, 0.118 mmol) was added. The solution was stirred for another 10 minutes; and then 6-bromo-2-phenylquinoline (1.1168 g, 3.93 mmol) and benzophenone imine (0.791 mL, 4.72 mmol) were added as a solution in dioxane (6.0 mL). The mixture was heated at 100° C. overnight. The mixture was cooled to room temperature and dilute with ethyl acetate. The organics were washed 2×100 mL with water, dried over magnesium sulfate, filtered, and concentrated onto silica gel. The reaction was purified by flash chromatography using an Argonaut Flashmaster Solo, 20 g column (10% ethyl acetate:hexanes for 30 min) to afford a yellow oil. (ESI(+)) m/e 385.0 (M+H)$^+$.

Example 47D 2-phenylquinolin-6-amine

In a 250 mL round-bottomed flask was placed EXAMPLE 47C (1.225 g, 3.19 mmol) in tetrahydrofuran (12.25 mL) to give a yellow solution. To the mixture was added hydrochloric acid (4.78 ml, 9.56 mmol). The solution was stirred at room temperature for 2 hours. To the mixture was added saturated sodium bicarbonate. The layers were separated saving the organic fraction. The organics were washed with brine, dried over magnesium sulfate, filtered, and concentrated onto silica gel. The reaction mixture was purified by flash chromatography using an Argonaut Flashmaster Solo, 20 g column (eluted with 10% ethyl acetate:hexanes for 10 min, then with 30% ethyl acetate:hexanes over 30 min) to afford a light yellow solid. (DCI(+)) m/e 221.0 (M+H)$^+$.

Example 47E

N-(5-bromo-2-chloropyrimidin-4-yl)-2-phenylquinolin-6-amine

In a 4 mL vial was charged EXAMPLE 47D (0.183 g, 0.829 mmol), 5-bromo-2,4-dichloropyrimidine (0.21 g, 0.922 mmol), and diisopropylethyl amine (0.145 mL, 0.829 mmol) in 2-propanol (4.61 mL) to give a yellow suspension. The reaction mixture was stirred at 25° C. for 20 hours. The mixture was checked by LCMS and starting material was present. The temperature was raised to 45° C. for 1 hour. The solution was cooled and diluted with dichloromethane and the organics were washed with water. The organics were dried over magnesium sulfate, filtered, and the solvent was removed by reduced pressure to afford a tan solid. (ESI(+)) m/e 412.8 (M+H)$^+$; (ESI(−)) m/e 410.9 (M−H)$^-$.

Example 47F 5-bromo-N$^2$-{2-methoxy-4-[4-(4-methylpiperazin-1-yl)piperidin-1-yl]phenyl}-N$^4$-(2-phenylquinolin-6-yl)pyrimidine-2,4-diamine In a 20 ml vial was charged EXAMPLE 47E (0.312 g, 0.758 mmol), EXAMPLE 47B (0.254 g, 0.834 mmol), and hydrochloric acid (0.227 ml, 0.909 mmol) in isoproyl alcohol (3.03 ml) to give a purple suspension. The mixture was heated at 45° C. on a hot plate overnight. The temperature was raised to 85° C. and heated for an additional 6 days then cooled. The dark residue was adsorbed onto silica gel and transfer to a 20 g silica gel column. The title compound was purified by flash chromatography using an Argonaut Flashmaster Solo, eluted with a gradient of 100% dichloromethane to 1:1 dichloromethane/methanol. The residue was further purified by HPLC using 0.1% ammonium hydroxide to afford a white solid. (ESI(+)) m/e 681.2 (M+H)$^+$; (ESI(−)) m/e 677.2 (M−H)$^-$; $^1$H NMR (300 MHz, DMSO-d$_6$) δ ppm 8.72 (s, 1H), 8.20-8.34 (m, 3H), 8.11-8.20 (m, 2H), 7.99-8.09 (m, 2H), 7.94 (s, 2H), 7.45-7.60 (m, 3H), 7.32 (d, 1H), 6.58 (d, 1H), 6.22 (d, 1H), 3.72 (s, 3H), 3.63 (d, 2H), 2.60 (t, 3H), 2.45 (s, 3H), 2.18-2.35 (m, 5H), 2.13 (s, 3H), 1.78 (dd, 2H), 1.35-1.54 (m, 2H).

Example 48

5-bromo-N$^2$-{2-methoxy-4-[4-(4-methylpiperazin-1-yl)piperidin-1-yl]phenyl}-N$^4$-(2-phenylquinolin-7-yl)pyrimidine-2,4-diamine The title compound was prepared as described in EXAMPLES 47C-47F, substituting 7-bromo-2-phenylquinoline for 6-bromo-2-phenylquinoline in EXAMPLE 47C. (ESI(+)) m/e 681.3 (M+H)$^+$; (ESI(−)) m/e 678.5 (M−H)$^-$; $^1$H-NMR (300 MHz, DMSO-d$_6$) δ ppm 8.81 (s, 1H), 8.37 (d, 1H), 8.31 (d, 3H), 8.19 (s, 1H), 8.07 (d, 1H), 7.76-7.92 (m, 3H), 7.47-7.62 (m, 4H), 6.52 (d, 1H), 6.15 (d, 1H), 3.81 (s, 3H), 3.38 (d, 2H), 2.20-2.46 (m, 10H), 2.13 (s, 4H), 1.62 (d, 2H), 1.20-1.38 (m, 2H).

Example 49

5-bromo-N$^2$-{2-methoxy-4-[4-(4-methylpiperazin-1-yl)piperidin-1-yl]phenyl}-N$^4$-quinolin-6-ylpyrimidine-2,4-diamine The title compound was prepared as described in EXAMPLES 47C-47F, substituting quinolin-6-amine for 6-bromo-2-phenylquinoline in EXAMPLE 47C. (ESI(+)) m/e 605.2 (M+H)$^+$; (ESI(−)) m/e 601.3 (M−H)$^-$; $^1$H-NMR (300 MHz, DMSO-d$_6$) δ ppm 8.76 (dd, 1H), 8.64 (s, 1H), 8.30 (s, 1H), 8.14 (s, 1H), 7.82-8.05 (m, 4H), 7.44 (dd, 1H), 7.39 (d, 1H), 6.61 (d, 1H), 6.33 (dd, 1H), 3.73 (s, 3H), 3.67 (d, 2H), 2.66 (t, 2H), 2.24-2.40 (m, 5H), 2.15 (s, 3H), 1.86 (d, 2H), 1.41-1.62 (m, 2H).

Example 50

5-bromo-N$^2$-{2-methoxy-4-[4-(4-methylpiperazin-1-yl)piperidin-1-yl]phenyl}-N$^4$-quinolin-7-ylpyrimidine-2,4-diamine The title compound was prepared as described in EXAMPLES 47C-47F, substituting quinolin-7-amine for 6-bromo-2-phenylquinoline in EXAMPLE 47C. (ESI(+)) m/e 605.2 (M+H)$^+$; (ESI(−)) m/e 603.2 (M−H)$^-$; $^1$H-NMR (300 MHz, DMSO-d$_6$) δ ppm 8.84 (dd, 1H), 8.78 (s, 1H), 8.20-8.32 (m, 2H), 8.17 (s, 1H), 7.81-7.98 (m, 3H), 7.47 (d, 1H), 7.42 (dd, 1H), 6.59 (d, 1H), 6.29 (dd, 1H), 3.78 (s, 3H), 3.59-3.69 (m, 3H), 2.61 (t, 2H), 2.17-2.48 (m, 8H), 2.14 (s, 3H), 1.82 (d, 2H), 1.46 (ddd, 2H).

Example 51

5-bromo-N-{2-methoxy-4-[4-(4-methylpiperazin-1-yl)piperidin-1-yl]phenyl}-4-(quinolin-7-yloxy)pyrimidin-2-amine

Example 51A 7-(5-bromo-2-chloropyrimidin-4-yloxy)quinoline

In a 4 mL vial was charged with quinolin-7-ol (0.200 g, 1.378 mmol) and sodium hydride (0.066 g, 1.653 mmol) in N,N-dimethylformamide (13.78 ml) to give a brown solution. The reaction was stirred at room temperature for 30 minutes and then 5-bromo-2,4-dichloropyrimidine (0.176 mL, 1.378 mmol) was added. The mixture was stirred at room temperature overnight. Diluted with 9:1 dichloromethane/methanol; washed with water and brine. The organic layer was dried over magnesium sulfate, filtered, and the solvent was removed under reduced pressure to afford a tan residue. (ESI (+)) m/e 337.7 (M+H)$^+$.

Example 51B

The title compound was prepared as described in EXAMPLE 47F, substituting EXAMPLE 52A for EXAMPLE 47E and purified by HPLC using 0.15% trifluoroacetic acid instead of 0.1% ammonium hydroxide to afford a white solid as the TFA salt. (ESI(+)) m/e 606.1 (M+H)$^+$; (ESI(−)) m/e 602.1 (M−H)$^−$; $^1$H-NMR (300 MHz, DMSO-d$_6$) δ ppm 8.97 (dd, 1H), 8.50 (dd, 1H), 8.45 (s, 1H), 8.26 (s, 1H), 8.12 (d, 1H), 7.95 (s, 1H), 7.85 (d, 1H), 7.54-7.64 (m, 2H), 7.07 (s, 1H), 6.51 (s, 1H), 3.71 (s, 3H), 3.41-3.66 (m, 4H), 2.89 (s, 5H), 2.80 (s, 3H), 2.73 (s, 5H), 1.87-2.05 (m, 2H), 1.44-1.64 (m, 2H).

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

The invention claimed is:

1. A compound of formula (I)

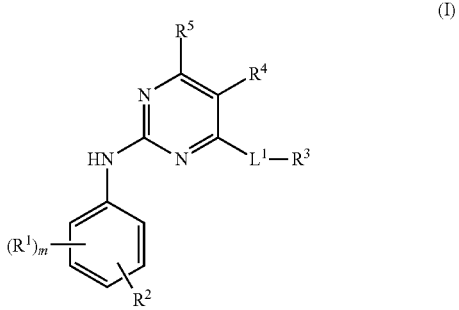

or a pharmaceutically acceptable salt, solvate, prodrug, or a combination thereof, wherein m is 0, 1, 2, 3, or 4;

L$^1$ is NH or O;

each occurrence of R$^1$, when present, is independently alkyl, alkenyl, alkynyl, halogen, haloalkyl, CN, NO$_2$, —OR$^{Z1}$, —OC(O)R$^{Z2}$, —SR$^{Z1}$, —S(O)R$^{Z2}$, —S(O)$_2$R$^{Z2}$, —S(O)$_2$N(R$^{Z3}$)(R$^{Z4}$), —N(R$^{Z3}$)(R$^{Z4}$), —N(R$^{Z3}$)C(O)R$^{Z2}$, —N(R$^{Z3}$)C(O)OR$^{Z2}$, —N(R$^{Z3}$)S(O)$_2$R$^{Z2}$, —N(R$^{Z3}$)C(O)N(R$^{Z3}$)(R$^{Z4}$), —N(R$^{Z3}$)S(O)$_2$N(R$^{Z3}$)(R$^{Z4}$), —C(O)R$^{Z1}$, —C(O)OR$^{Z1}$, —C(O)N(R$^{Z3}$)(R$^{Z4}$), —(C$_{1-6}$ alkylenyl)-OR$^{Z1}$, —(C$_{1-6}$ alkylenyl)-OC(O)R$^{Z2}$, —(C$_{1-6}$ alkylenyl)-SR$^{Z1}$, —(C$_{1-6}$ alkylenyl)-S(O)R$^{Z2}$, —(C$_{1-6}$ alkylenyl)-S(O)$_2$R$^{Z2}$, —(C$_{1-6}$ alkylenyl)-S(O)$_2$N(R$^{Z3}$)(R$^{Z4}$), —(C$_{1-6}$ alkylenyl)-N(R$^{Z3}$)(R$^{Z4}$), —(C$_{1-6}$ alkylenyl)-N(R$^{Z3}$)C(O)R$^{Z2}$, —(C$_{1-6}$ alkylenyl)-N(R$^{Z3}$)C(O)OR$^{Z2}$, —(C$_{1-6}$ alkylenyl)-N(R$^{Z3}$)S(O)$_2$R$^{Z2}$, —(C$_{1-6}$ alkylenyl)-N(R$^{Z3}$)C(O)N(R$^{Z3}$)(R$^{Z4}$), —(C$_{1-6}$ alkylenyl)-N(R$^{Z3}$)S(O)$_2$N(R$^{Z3}$)(R$^{Z4}$), —(C$_{1-6}$ alkylenyl)-C(O)R$^{Z1}$, —(C$_{1-6}$ alkylenyl)-C(O)OR$^{Z1}$, or -(C$_{1-6}$ alkylenyl)-C(O)N(R$^{Z3}$)(R$^{Z4}$);

R$^2$ is a heterocycle optionally substituted with 1, 2, 3, or 4 substituents independently selected from the group consisting of alkyl, alkenyl, alkynyl, halogen, haloalkyl, oxo, CN, NO$_2$, G$^2$, —OR$^6$, —OC(O)R$^7$, —SR$^6$, —S(O)R$^7$, —S(O)$_2$R$^7$, —S(O)$_2$N(R$^8$)(R$^9$), —N(R$^8$)(R$^9$), —N(R$^8$)C(O)R$^7$, —N(R$^8$)C(O)OR$^7$, —N(R$^8$)S(O)$_2$R$^7$, —N(R$^8$)C(O)N(R$^8$)(R$^9$), —N(R$^8$)C(O)—(C$_{1-6}$ alkylenyl)-N(R$^8$)(R$^9$), —N(R$^8$)S(O)$_2$N(R$^8$)(R$^9$), —C(O)R$^6$, —C(O)OR$^6$, —C(O)N(R$^8$)(R$^9$), —(C$_{1-6}$ alkylenyl)-G$^3$, —(C$_{1-6}$ alkylenyl)-OR$^6$, —(C$_{1-6}$ alkylenyl)-OC(O)R$^7$, —(C$_{1-6}$ alkylenyl)-SR$^6$, —(C$_{1-6}$ alkylenyl)-S(O)R$^7$, —(C$_{1-6}$ alkylenyl)-S(O)$_2$R$^7$, —(C$_{1-6}$ alkylenyl)-S(O)$_2$N(R$^8$)(R$^9$), —(C$_{1-6}$ alkylenyl)-N(R$^8$)(R$^9$), —(C$_{1-6}$ alkylenyl)-N(R$^8$)C(O)R$^7$, —(C$_{1-6}$ alkylenyl)-N(R$^8$)C(O)OR$^7$, —(C$_{1-6}$ alkylenyl)-N(R$^8$)S(O)$_2$R$^7$, —(C$_{1-6}$ alkylenyl)-N(R$^8$)C(O)N(R$^8$)(R$^9$), —(C$_{1-6}$ alkylenyl)-N(R$^8$)S(O)$_2$N(R$^8$)(R$^9$), —(C$_{1-6}$ alkylenyl)-C(O)R$^6$, —(C$_{1-6}$ alkylenyl)-C(O)OR$^6$, and —(C$_{1-6}$ alkylenyl)-C(O)N(R$^8$)(R$^9$);

R$^3$ is benzimidazolyl, indazolyl, benzothiazolyl, benzoxazolyl, or quinolinyl; each of which is independently unsubstitued or substituted with 1, 2, or 3 substituents independently selected from the group consisting of alkyl, alkenyl, alkynyl, halogen, G$^3$, —(C$_{1-6}$ alkylenyl)-G$^3$, —O(alkyl), —O(haloalkyl), —SR$^{Z1}$, —S(O)R$^{Z2}$, —S(O)$_2$R$^{Z2}$, —C(O)N(R$^{Z3}$)(R$^{Z4}$), and haloalkyl; with the proviso that when R$^3$ is quinolinyl, then R$^2$ is substituted with 1, 2, 3, or 4 substituents wherein one of the substituents is G$^2$, R$^4$ is alkyl, haloalkyl, halogen, or —CN;

R$^5$ is hydrogen, alkyl, haloalkyl, halogen, or —CN;

each occurrence of R$^6$ and R$^9$ are each independently hydrogen, alkyl, haloalkyl, —(C$_{1-6}$ alkylenyl)-CN, —(C$_{1-6}$ alkylenyl)-OH, —(C$_{1-6}$ alkylenyl)-C(O)OH, G$^3$, or —(C$_{1-6}$ alkylenyl)-G$^3$;

each occurrence of R$^7$ is independently alkyl, haloalkyl, —(C$_{1-6}$ alkylenyl)-CN, —(C$_{1-6}$ alkylenyl)-OH, G$^3$, or —(C$_{1-6}$ alkylenyl)-G$^3$;

each occurrence of R$^8$ is independently hydrogen, alkyl, or haloalkyl;

G$^2$ is a heterocycle optionally substituted with 1, 2, 3, 4, or 5 R$^{10}$ groups;

each occurrence of G$^3$ is independently aryl, heteroaryl, heterocycle, cycloalkyl, or cycloalkenyl, each of which is independently unsubstituted or substituted with 1, 2, 3, 4, or 5 R$^{10}$ groups;

each occurrence of R$^{10}$ is independently alkyl, alkenyl, alkynyl, halogen, haloalkyl, oxo, CN, NO$_2$, —OR$^{Z1}$, —OC(O)R$^{Z2}$, —SR$^{Z1}$, —S(O)R$^{Z2}$, —S(O)$_2$R$^{Z2}$, —S(O)$_2$N(R$^{Z3}$)(R$^{Z4}$), —N(R$^{Z3}$)(R$^{Z4}$), —N(R$^{Z3}$)C(O)R$^{Z2}$, —N(R$^{Z3}$)C(O)OR$^{Z2}$, —N(R$^{Z3}$)S(O)$_2$R$^{Z2}$, —N(R$^{Z3}$)C(O)N(R$^{Z3}$)(R$^{Z4}$), —N(R$^{Z3}$)S(O)$_2$N(R$^{Z3}$)(R$^{Z4}$), —C(O)R$^{Z1}$, —C(O)OR$^{Z1}$, —C(O)N(R$^{Z3}$)(R$^{Z4}$), —(C$_{1-6}$ alkylenyl)-OR$^{Z1}$, -(C$_{1-6}$ alkylenyl)-OC(O)R$^{Z2}$, —(C$_{1-6}$ alkylenyl)-SR$^{Z1}$, —(C$_{1-6}$ alkylenyl)-S(O)R$^{Z2}$, —(C$_{1-6}$ alkylenyl)-S(O)$_2$R$^{Z2}$, —(C$_{1-6}$ alkylenyl)-S(O)$_2$N(R$^{Z3}$)(R$^{Z4}$), —(C$_{1-6}$ alkylenyl)-N(R$^{Z3}$)(R$^{Z4}$), —(C$_{1-6}$ alkylenyl)-N(R$^{Z3}$)C(O)R$^{Z2}$, —(C$_{1-6}$ alkylenyl)-N(R$^{Z3}$)C(O)OR$^{Z2}$, —(C$_{1-6}$ alkylenyl)-N(R$^{Z3}$)S(O)$_2$R$^{Z2}$, —(C$_{1-6}$ alkylenyl)-N(R$^{Z3}$)C(O)N(R$^{Z3}$)(R$^{Z4}$), —(C$_{1-6}$ alkylenyl)-N(R$^{Z3}$)S(O)$_2$N(R$^{Z3}$)(R$^{Z4}$), —(C$_{1-6}$ alkylenyl)-C(O)R$^{Z1}$, —(C$_{1-6}$ alkylenyl)-C(O)OR$^{Z1}$, or —(C$_{1-6}$ alkylenyl)-C(O)N(R$^{Z3}$)(R$^{Z4}$);

each occurrence of R$^{Z1}$, R$^{Z3}$, and R$^{Z4}$, are each independently hydrogen, alkyl, or haloalkyl; and each occurrence of R$^{Z2}$ is independently alkyl or haloalkyl.

2. The compound according to claim 1 having formula (I) or a pharmaceutically acceptable salt or solvate thereof, wherein m is 1 and R$^1$ is OR$^{Z1}$.

3. The compound according to claim 1 or a pharmaceutically acceptable salt or solvate thereof having formula (I) or a pharmaceutically acceptable salt or solvate thereof, wherein
$L^1$ is NH; and
$R^3$ is indazolyl, benzimidazolyl, benzoxazolyl, or benzothiazolyl; each of which is optionally substituted.

4. The compound according to claim 1 having formula (I) or a pharmaceutically acceptable salt or solvate thereof, wherein
$L^1$ is NH;
$R^3$ is indazolyl, benzimidazolyl, benzoxazolyl, or benzothiazolyl; each of which is optionally substituted;
$R^5$ is hydrogen;
m is 1; and
$R^1$ is $OR^{Z1}$.

5. The compound according to claim 1 having formula (I), or a pharmaceutically acceptable salt or solvate thereof, wherein
$L^1$ is NH;
$R^3$ is indazolyl, benzimidazolyl, benzoxazolyl, or benzothiazolyl; each of which is optionally substituted;
$R^5$ is hydrogen; and
$R^2$ is an optionally substituted monocyclic heterocycle.

6. The compound according to claim 5 having formula (I), or a pharmaceutically acceptable salt or solvate thereof, wherein
$R^2$ is optionally substituted with one or two substituents independently selected from the group consisting of alkyl, haloalkyl, $G^2$, and $N(R^8)(R^9)$.

7. The compound according to claim 5 having formula (I), or a pharmaceutically acceptable salt or solvate thereof, wherein
$R^2$ is substituted with one $G^2$ group.

8. The compound according to claim 1 having formula (I), or a pharmaceutically acceptable salt or solvate thereof, wherein
$L^1$ is NH;
m is 0 or 1;
$R^1$ is $OR^{Z1}$,
$R^2$ is a monocyclic heterocycle substituted with one $G^2$ group;
$G^2$ is an optionally substituted monocyclic heterocycle; and
$R^3$ is indazolyl substituted with one or two substituents independently selected from the group consisting of alkyl and $-S(O)_2R^{Z2}$.

9. The compound according to claim 1 having formula (I), or a pharmaceutically acceptable salt or solvate thereof, wherein
$L^1$ is NH;
$R^3$ is optionally substituted quinolinyl; and
$R^2$ is a monocyclic heterocycle substituted with 1, 2, or 3 substituents wherein one of the substituents is $G^2$, and the others are independently selected from the group consisting of alkyl and haloalkyl.

10. The compound according to claim 1 having formula (I), or a pharmaceutically acceptable salt or solvate thereof, wherein
$L^1$ is NH;
$R^3$ is optionally substituted quinolinyl; and
$R^2$ is a monocyclic heterocycle substituted with one $G^2$ group.

11. The compound according to claim 1 having formula (I), or a pharmaceutically acceptable salt or solvate thereof, wherein
$L^1$ is O;
$R^3$ is optionally substituted quinolinyl; and
$R^2$ is a monocyclic heterocycle substituted with 1, 2, or 3 substituents wherein one of the substituents is $G^2$, and the others are independently selected from the group consisting of alkyl and haloalkyl.

12. The compound according to claim 1 having formula (I), or a pharmaceutically acceptable salt or solvate thereof, wherein
$L^1$ is O;
$R^3$ is optionally substituted quinolinyl; and
$R^2$ is a monocyclic heterocycle substituted with one $G^2$ group.

13. The compound according to claim 1 having formula (I-i) or a pharmaceutically acceptable salt or solvate thereof

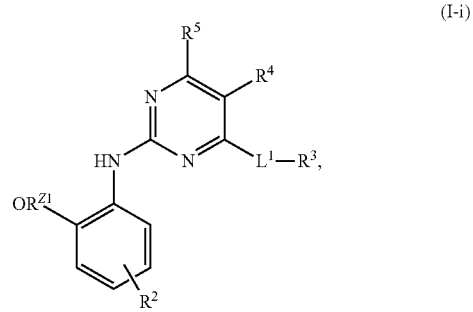

(I-i)

wherein $R^{Z1}$, $R^2$, $R^3$, $R^4$, $R^5$, and $L^1$ are as set forth in claim 1.

14. The compound according to claim 13 having formula (I-i), or a pharmaceutically acceptable salt or solvate thereof, wherein
$R^3$ is indazolyl, benzimidazolyl, benzoxazolyl, or benzothiazolyl; each of which is optionally substituted.

15. The compound according to claim 13 having formula (I-i), or a pharmaceutically acceptable salt or solvate thereof, wherein
$L^1$ is NH; and
$R^3$ is indazolyl, benzimidazolyl, benzoxazolyl, or benzothiazolyl; each of which is optionally substituted.

16. The compound according to claim 13 having formula (I-i) or a pharmaceutically acceptable salt or solvate thereof, wherein
$L^1$ is NH;
$R^3$ is indazolyl, benzimidazolyl, benzoxazolyl, or benzothiazolyl; each of which is optionally substituted; and
$R^5$ is hydrogen.

17. The compound according to claim 13 having formula (I-i), or a pharmaceutically acceptable salt or solvate thereof, wherein
$L^1$ is NH;
$R^3$ is indazolyl, benzimidazolyl, benzoxazolyl, or benzothiazolyl; each of which is optionally substituted;
$R^5$ is hydrogen; and
$R^2$ is an optionally substituted monocyclic heterocycle.

18. The compound according to claim 17 having formula (I-i), or a pharmaceutically acceptable salt or solvate thereof, wherein
$R^2$ is optionally substituted with one or two substituents independently selected from the group consisting of alkyl, haloalkyl, $G^2$, and $N(R^8)(R^9)$.

19. The compound according to claim 17 having formula (I-i), or a pharmaceutically acceptable salt or solvate thereof, wherein
$R^2$ is substituted with one $G^2$ group.

20. The compound according to claim 13 having formula (I-i), or a pharmaceutically acceptable salt or solvate thereof, wherein
$L^1$ is NH;
$R^2$ is a monocyclic heterocycle substituted with one $G^2$ group;

G² is an optionally substituted monocyclic heterocycle; and

R³ is indazolyl substituted with one or two substituents independently selected from the group consisting of alkyl and —S(O)₂R^{Z2}.

21. The compound according to claim 1 or a pharmaceutically acceptable salt or solvate thereof, selected from the group consisting of 5-bromo-N²-[4-(4-ethylpiperazin-1-yl)phenyl]-N⁴-[2-(trifluoromethyl)-1H-benzimidazol-5-yl]pyrimidine-2,4-diamine;

N⁴-(2-benzyl-1H-benzimidazol-5-yl)-5-bromo-N²-[4-(4-ethylpiperazin-1-yl)phenyl]pyrimidine-2,4-diamine;

5-bromo-N²-[4-(4-ethylpiperazin-1-yl)phenyl]-N⁴-[2-(2-phenylethyl)-1H-benzimidazol-5-yl]pyrimidine-2,4-diamine;

N⁴-(1-benzyl-1H-benzimidazol-5-yl)-5-bromo-N²-[4-(4-ethylpiperazin-1-yl)phenyl]pyrimidine-2,4-diamine;

N⁴-(1-benzyl-1H-benzimidazol-6-yl)-5-bromo-N²-[4-(4-ethylpiperazin-1-yl)phenyl]pyrimidine-2,4-diamine;

5-bromo-N²-[4-(4-ethylpiperazin-1-yl)phenyl]-N⁴-(2-methyl-1H-benzimidazol-4-yl)pyrimidine-2,4-diamine;

5-bromo-N²-[4-(4-ethylpiperazin-1-yl)phenyl]-N⁴-1H-indazol-5-ylpyrimidine-2,4-diamine;

5-chloro-N²-[4-(4-ethylpiperazin-1-yl)phenyl]-N⁴-1H-indazol-5-ylpyrimidine-2,4-diamine;

N²-[4-(4-ethylpiperazin-1-yl)phenyl]-N⁴-1H-indazol-5-yl-5-methylpyrimidine-2,4-diamine;

2-{[4-(4-ethylpiperazin-1-yl)phenyl]amino}-4-(1H-indazol-5-ylamino)pyrimidine-5-carbonitrile;

N²-[4-(4-ethylpiperazin-1-yl)phenyl]-N⁴-1H-indazol-5-yl-5-(trifluoromethyl)pyrimidine-2,4-diamine;

5-bromo-N²-{4-[4-(dimethylamino)piperidin-1-yl]-2-methoxyphenyl}-N⁴-1H-indazol-5-ylpyrimidine-2,4-diamine;

5-bromo-N⁴-1H-indazol-5-yl-N²-{2-methoxy-4-[4-(4-methylpiperazin-1-yl)piperidin-1-yl]phenyl}pyrimidine-2,4-diamine;

N⁴-1,3-benzothiazol-5-yl-5-bromo-N²-[4-(4-ethylpiperazin-1-yl)phenyl]pyrimidine-2,4-diamine;

5-bromo-N²-[4-(4-ethylpiperazin-1-yl)phenyl]-N⁴-(2-methyl-1,3-benzoxazol-4-yl)pyrimidine-2,4-diamine;

5-bromo-N²-{4-[4-(dimethylamino)piperidin-1-yl]-2-methoxyphenyl}-N⁴-(2-methyl-1H-benzimidazol-4-yl)pyrimidine-2,4-diamine;

5-chloro-N²-{4-[4-(dimethylamino)piperidin-1-yl]-2-methoxyphenyl}-N⁴-(2-methyl-1H-benzimidazol-4-yl)pyrimidine-2,4-diamine;

5-chloro-N²-{4-[4-(dimethylamino)piperidin-1-yl]-2-methoxyphenyl}-N⁴-(1-methyl-1H-indazol-5-yl)pyrimidine-2,4-diamine;

5-bromo-N²-{4-[4-(dimethylamino)piperidin-1-yl]-2-methoxyphenyl}-N⁴-(1-methyl-1H-indazol-5-yl)pyrimidine-2,4-diamine;

5-bromo-N⁴-(6-chloro-1H-indazol-5-yl)-N²-{4-[4-(dimethylamino)piperidin-1-yl]-2-methoxyphenyl}pyrimidine-2,4-diamine;

5-bromo-N²-{4-[4-(dimethylamino)piperidin-1-yl]-2-methoxyphenyl}-N⁴-(6-methyl-1H-indazol-5-yl)pyrimidine-2,4-diamine;

5-bromo-N²-{4-[4-(dimethylamino)piperidin-1-yl]-2-methoxyphenyl}-N⁴-(2-methyl-1,3-benzothiazol-5-yl)pyrimidine-2,4-diamine;

5-bromo-N²-{4-[4-(dimethylamino)piperidin-1-yl]-2-methoxyphenyl}-N⁴-[6-(isopropylsulfonyl)-1H-indazol-5-yl]pyrimidine-2,4-diamine;

5-bromo-N²-{4-[4-(dimethylamino)piperidin-1-yl]-2-methoxyphenyl}-N⁴-[6-(isopropylthio)-1H-indazol-5-yl]pyrimidine-2,4-diamine;

5-chloro-N²-{4-[4-(dimethylamino)piperidin-1-yl]-2-methoxyphenyl}-N⁴-(2-methyl-1,3-benzoxazol-5-yl)pyrimidine-2,4-diamine;

5-chloro-N²-{4-[4-(dimethylamino)piperidin-1-yl]-2-methoxyphenyl}-N⁴-[6-(isopropylsulfonyl)-1H-indazol-5-yl]pyrimidine-2,4-diamine;

5-bromo-N²-{4-[4-(dimethylamino)piperidin-1-yl]-2-methoxyphenyl}-N⁴-[6-(isopropylsulfonyl)-1-methyl-1H-indazol-5-yl]pyrimidine-2,4-diamine;

5-bromo-N⁴-[6-(isopropylsulfonyl)-1-methyl-1H-indazol-5-yl]-N²-{2-methoxy-4-[4-(4-methylpiperazin-1-yl)piperidin-1-yl]phenyl}pyrimidine-2,4-diamine;

5-bromo-N²-{4-[4-(dimethylamino)piperidin-1-yl]-2-methoxyphenyl}-N⁴-[6-(isopropylsulfonyl)-2-methyl-2H-indazol-5-yl]pyrimidine-2,4-diamine;

5-bromo-N²-{4-[4-(dimethylamino)piperidin-1-yl]-2-methoxyphenyl}-N⁴-[6-(ethylsulfonyl)-1H-indazol-5-yl]pyrimidine-2,4-diamine;

5-bromo-N²-{4-[4-(dimethylamino)piperidin-1-yl]phenyl}-N⁴-[6-(ethylsulfonyl)-1H-indazol-5-yl]pyrimidine-2,4-diamine;

5-bromo-N⁴-[6-(ethylsulfonyl)-1H-indazol-5-yl]-N²-(2-methoxy-4-morpholin-4-ylphenyl)pyrimidine-2,4-diamine;

5-bromo-N²-{4-[4-(dimethylamino)piperidin-1-yl]-2-methoxyphenyl}-N⁴-[6-(ethylsulfonyl)-1-methyl-1H-indazol-5-yl]pyrimidine-2,4-diamine;

5-bromo-N²-{4-[4-(dimethylamino)piperidin-1-yl]-2-methoxyphenyl}-N⁴-[1-methyl-6-(methylsulfonyl)-1H-indazol-5-yl]pyrimidine-2,4-diamine;

5-{[5-bromo-2-({4-[4-(dimethylamino)piperidin-1-yl]-2-methoxyphenyl}amino)pyrimidin-4-yl]amino}-N,1-dimethyl-1H-indazole-6-carboxamide;

5-bromo-N²-{4-[4-(dimethylamino)piperidin-1-yl]phenyl}-N⁴-[6-(ethylsulfonyl)-1-methyl-1H-indazol-5-yl]pyrimidine-2,4-diamine;

5-bromo-N²-{4-[4-(dimethylamino)piperidin-1-yl]phenyl}-N⁴-[1-methyl-6-(methylsulfonyl)-1H-indazol-5-yl]pyrimidine-2,4-diamine;

5-{[5-bromo-2-({4-[4-(dimethylamino)piperidin-1-yl]phenyl}amino)pyrimidin-4-yl]amino}-N,1-dimethyl-1H-indazole-6-carboxamide;

5-bromo-N⁴-[6-(ethylsulfonyl)-1-methyl-1H-indazol-5-yl]-N²-(2-methoxy-4-morpholin-4-ylphenyl)pyrimidine-2,4-diamine;

5-bromo-N²-(2-methoxy-4-morpholin-4-ylphenyl)-N⁴-[1-methyl-6-(methylsulfonyl)-1H-indazol-5-yl]pyrimidine-2,4-diamine;

5-({5-bromo-2-[(2-methoxy-4-morpholin-4-ylphenyl)amino]pyrimidin-4-yl}amino)-N,1-dimethyl-1H-indazole-6-carboxamide;

5-bromo-N⁴-[6-(ethylsulfonyl)-1-methyl-1H-indazol-5-yl]-N²-[4-(4-isopropylpiperazin-1-yl)-2-methoxyphenyl]pyrimidine-2,4-diamine;

5-bromo-N²-[4-(4-isopropylpiperazin-1-yl)-2-methoxyphenyl]-N⁴-[1-methyl-6-(methylsulfonyl)-1H-indazol-5-yl]pyrimidine-2,4-diamine;

5-[(5-bromo-2-{[4-(4-isopropylpiperazin-1-yl)-2-methoxyphenyl]amino}pyrimidin-4-yl)amino]-N,1-dimethyl-1H-indazole-6-carboxamide;

5-bromo-N²-[4-(1,1-dioxidothiomorpholin-4-yl)phenyl]-N⁴-[6-(ethylsulfonyl)-1-methyl-1H-indazol-5-yl]pyrimidine-2,4-diamine;

5-bromo-N⁴-[6-(ethylsulfonyl)-1-methyl-1H-indazol-5-yl]-N²-{2-methoxy-4-[4-(4-methylpiperazin-1-yl)piperidin-1-yl]phenyl}pyrimidine-2,4-diamine;

5-bromo-N²-{2-methoxy-4-[4-(4-methylpiperazin-1-yl)piperidin-1-yl]phenyl}-N⁴-(2-phenylquinolin-6-yl)pyrimidine-2,4-diamine;

5-bromo-N²-{2-methoxy-4-[4-(4-methylpiperazin-1-yl)piperidin-1-yl]phenyl}-N⁴-(2-phenylquinolin-7-yl)pyrimidine-2,4-diamine;

5-bromo-$N^2$-{2-methoxy-4-[4-(4-methylpiperazin-1-yl)piperidin-1-yl]phenyl}-$N^4$-quinolin-6-ylpyrimidine-2,4-diamine;

5-bromo-$N^2$-{2-methoxy-4-[4-(4-methylpiperazin-1-yl)piperidin-1-yl]phenyl}-$N^4$-quinolin-7-ylpyrimidine-2,4-diamine; and 5-bromo-N-{2-methoxy-4-[4-(4-methylpiperazin-1-yl)piperidin-1-yl]phenyl}-4-(quinolin-7-yloxy)pyrimidin-2-amine.

22. A pharmaceutical composition comprising a compound of claim 1 or pharmaceutically acceptable salt or solvate thereof, and one or more pharmaceutically acceptable carrier.

\* \* \* \* \*